US009878001B2

(12) United States Patent
Goldberg et al.

(10) Patent No.: US 9,878,001 B2
(45) Date of Patent: Jan. 30, 2018

(54) IMMUNOSUPPRESSIVE TAT DERIVATIVE POLYPEPTIDES

(71) Applicant: PIN Pharma, Inc., New York, NY (US)

(72) Inventors: Joshua Goldberg, New York, NY (US); Colin Bier, Toronto (CA); Christoph Hotz-Behofsits, New York, NY (US); Sophie Hanscom, New York, NY (US)

(73) Assignee: PIN Pharma, Inc., New York, NY (US)

( * ) Notice: Subject to any disclaimer, the term of this patent is extended or adjusted under 35 U.S.C. 154(b) by 0 days.

(21) Appl. No.: 14/099,475

(22) Filed: Dec. 6, 2013

(65) Prior Publication Data
US 2014/0178420 A1 Jun. 26, 2014

Related U.S. Application Data

(60) Provisional application No. 61/881,266, filed on Sep. 23, 2013, provisional application No. 61/734,135, filed on Dec. 6, 2012.

(51) Int. Cl.
*A61K 39/21* (2006.01)
*A61K 38/16* (2006.01)
*C07K 14/16* (2006.01)

(52) U.S. Cl.
CPC ............ *A61K 38/162* (2013.01); *A61K 39/21* (2013.01); *C07K 14/163* (2013.01); *C12N 2740/16311* (2013.01)

(58) Field of Classification Search
CPC .................. A61K 39/21; C07K 14/163; C12N 2740/16311
See application file for complete search history.

(56) References Cited

U.S. PATENT DOCUMENTS

| | | | |
|---|---|---|---|
| 6,193,981 B1 | 2/2001 | Goldstein | |
| 6,667,151 B1 | 12/2003 | Cohen | |
| 7,087,377 B2 | 8/2006 | Loret | |
| 7,927,580 B2 | 4/2011 | Cohen | |
| 8,530,431 B2 * | 9/2013 | Cohen | A61K 31/675 514/19.4 |
| 2006/0160183 A1 | 7/2006 | Cohen | |
| 2007/0248618 A1 | 10/2007 | Cohen | |
| 2008/0044435 A1 | 2/2008 | Cohen | |
| 2011/0009336 A1 | 1/2011 | Cohen | |
| 2011/0195078 A1 | 8/2011 | Cohen | |

FOREIGN PATENT DOCUMENTS

| | | |
|---|---|---|
| WO | 02-090558 A1 | 11/2002 |
| WO | WO 2010/111292 A1 * | 9/2010 |
| WO | 2015-051245 A1 | 4/2015 |

OTHER PUBLICATIONS

Wong, J. K., et al., Jun. 2010, Differential induction of interleukin-10 in monocytes by HIV-1 Clade B and Clade C Tat proteins, J. Biol. Chem. 285(24):18319-18325.*

Mayol, K., et al., 2007, Design and characterization of an HIV-1 Tat mutant: Inactivation of viral and cellular functions but not antigenicity, Vaccine 25:6047-6060.*

Ruben, S., et al., Jan. 1989, Structural and functional characterization of human immunodeficiency virus tat protein, J. Virol. 63(1):1-8.*

Fleming, B. D., and D. M. Mosser, 2011, Regulatory macrophages: Setting the Threshold for Therapy, Eur. J. Immunol. 41:2470-2525.*

Broadstock, M. , et al., 2014, Latest treatment options for Alzheimer's disease, Parkinson's disease dementia and dementia with Lewy bodies, Exp. Opin. Pharmacother. 15(13):1797-1810.*

Frisardi, V., et al., 2010, Towards disease-modifying treatment of Alzheimer's disease: drugs targeting B-amyloid, Cur. Alzheimer Res. 7(1):40-55.*

Altfelds, M., and M. Gale, Jr., 2015, Innate immunity against HIV-1 infection, Nat. Immunol. 16(6):554-562.*

NCBI GenBank accession No. ACN6334.1, Mar. 15, 2009.

Kuppuswamy M et al. "Multiple functional domains of Tat, the trans-activator of HIV-1, defined by mutational analysis," Nucl Acids Res 17:3551-61, 1989.

Ranga U et al. "Tat protein of human immunodeficiency virus type I subtype C strains is a defective chemokine," J Virol 78:2586-90, 2004.

PCT/US2013/073658 International Search Report and Written Opinion.

Arbuckle Mi et al. "The SH3 domain of postsynaptic density 95 mediates inflammatory pain through phosphatidyinositol-3-kinase recruitment," EMBO Reports 11:473-78, 2010.

Kamata T et a. "Src homology2 domain-containing tyrosine phosphatase SHP-1 controls the development of allergic airway inflammation," J Clin Invest 111:109-19, 2003.

Mayer BJ "SH3 domains: complexity in moderation," J Cell Sci 114:1253-63, 2001.

Reebye V et al. "A perspective on non-catalytic Src homology (SH) adaptor signalling proteins," Cellular Signalling 24:388-92, 2012.

Richardson et al. "Cellular mechanisms of neurogenic inflammation," J Pharmacol Exp Ther 302:839-45, 2002.

Fultz et al. "SIVsmm Infection of Macaque and Mangabey Monkeys: Correlation between in vivo and in vitro properties of different isolates." Develop. biol. Standard., vol. 72, pp. 253-258, 1990.

Reske-Kunz et al. "Disproportion in T-Cell Subpopulations in Immunodeficient Mutant hr/hr Mice." J. Exp. Med. vol. 149, 1979, 228-233.

Seipel et al. "Tara, a novel F-actin binding protein, associates with the Trio guanine nucleotide exchange factor and regulates actin cytoskeletal organization." Research Article, Journal of Cell Science 114, 389-399, 2000.

Wadia et al. "Transmembrane delivery of protein and peptide drugs by TAT—mediated transduction in the treatment of cancer." Advanced Drug Devliery Reviews 57, 2005, 579-596.

Prive GG et al. "Specific peptides for the therapeutic targeting of oncogenes," Curr Opin Genet Devel 16:71-77, 2006.

Bettelli E et al. "TH-17 cells in the circle of immunity and autoimmunity," Nat Immunol 8:345-50, 2007.

(Continued)

*Primary Examiner* — Jeffrey Parkin

(74) *Attorney, Agent, or Firm* — K&L Gates LLP; Louis C. Cullman; David Diamond

(57) ABSTRACT

The present specification provides immunosuppressive Tat derivative polypeptides, compositions, and methods of using such polypeptides and compositions to treat an autoimmune disease, an inflammation-associated disease and/or a neurodegenerative disease.

7 Claims, 19 Drawing Sheets

(56) References Cited

OTHER PUBLICATIONS

Hirano T "Revival of the autoantibody model of rheumatoid arthritis," Nat Immunol 3:342-44, 2002.
Martin R et al. "Immunotherapy of multiple sclerosis: Where are we? Where should we go?" Nat Immunol 2:785-88, 2001.
Wong JK et al. "Differential Induction of Interleukin-10 in Monocytes by HIV-1 Clade B and Clade C Tat Proteins." J Biol Chem 285:18319-18325, 2010.

* cited by examiner

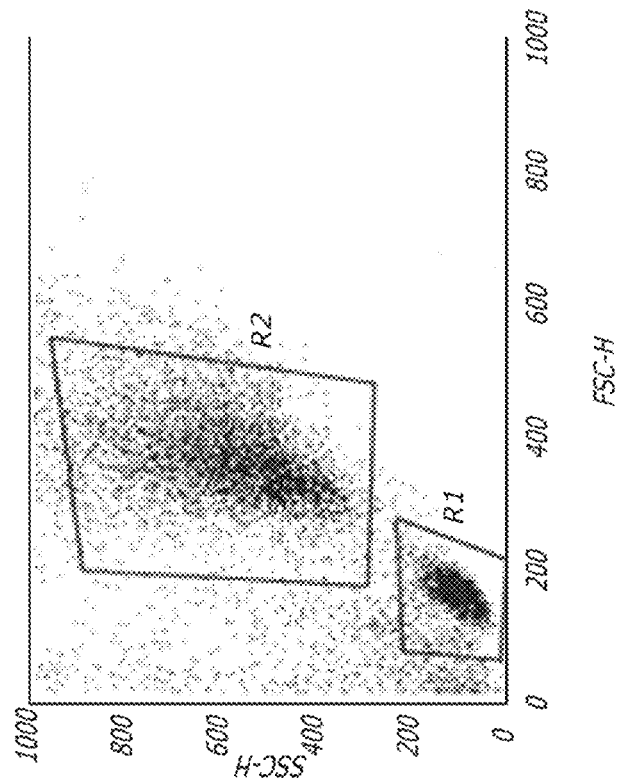
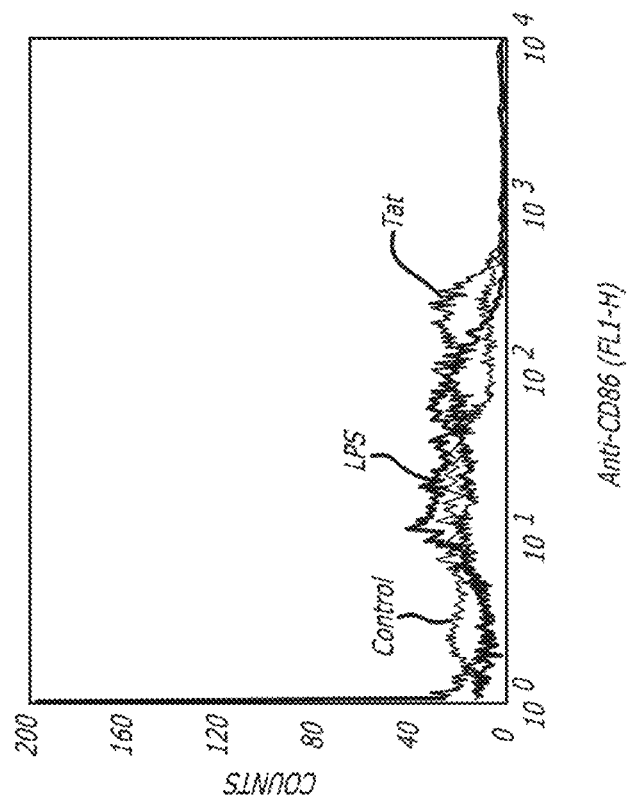
FIG. 1A
FIG. 1B

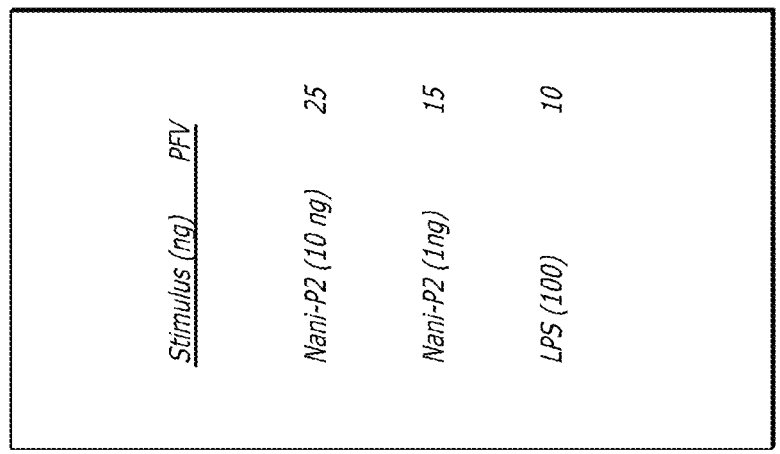
FIG. 11
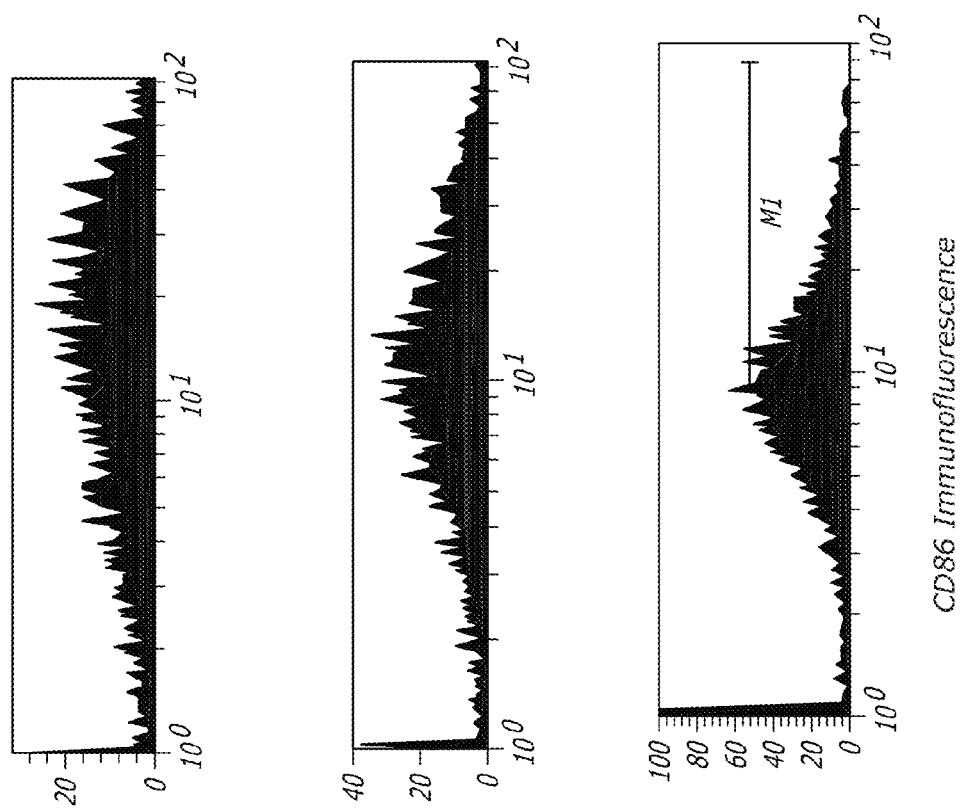

IMMUNOSUPPRESSIVE TAT DERIVATIVE POLYPEPTIDES

CROSS-REFERENCE TO RELATED APPLICATIONS

This application claims the benefit of U.S. provisional patent applications 61/734,135 filed Dec. 6, 2012 and 61/881,266 filed Sep. 23, 2013, the contents of both of which are incorporated by reference herein in their entirety.

FIELD

The present application is drawn to immunosuppressive Human Immunodeficiency Virus (HIV) transactivator of transcription (Tat) derivative polypeptides for the treatment of diseases characterized by aberrant immune responses such as neurodegenerative and autoimmune diseases and inflammation-associated diseases.

BACKGROUND

The Human Immunodeficiency Virus (HIV) transactivator of transcription (Tat) mediates at least two independent activities, a receptor-mediated triggering event at the cellular surface and an intracellular trans-activation activity that controls antigen-presenting cell (APC) differentiation. The receptor-mediated triggering event mediated by Tat is specific to APC, committing them for activation and differentiation into highly immunosuppressive antigen presenting cell regulatory macrophages (AReg) or into dendritic cells (DC) that stimulate specific cytotoxic T lymphocytes.

Antigen-presenting cells, macrophages and dendritic cells are critical in the pathogenesis or response to a variety of diseases, disorders and undesired immune responses. Tat triggers monocytes to differentiate into antigen-presenting macrophages expressing molecules that specifically suppress the immune response to the presented antigen(s). In autoimmune diseases, certain of the body's own endogenous molecules are incorrectly recognized as foreign, resulting in extensive inflammation and tissue damage. In one example, degradation of collagen type II into immunogenic peptides can trigger rheumatoid arthritis (RA) in animals and has been associated with human RA. Considerable research has centered on reducing the immune response to these proteins. The antigen-specific macrophage-induced suppression attributed to Tat can be applied to the reduction of the undesired immune response to foreign and endogenous molecules associated with inflammation and neurodegeneration.

Attempts to treat inflammation and autoimmune disorders have met with limited success. This is due, in part, to the fact that the etiology of inflammation and autoimmune disorders is a complex response based in part on the various inflammation-inducing molecules and the multitude of inflammation-mediating and -sensitizing molecules that appear to elicit inflammation via redundant mechanisms. Therefore, compounds, compositions, and methods that can treat inflammation, neurodegenerative disease, or an autoimmune disorder would be highly desirable.

SUMMARY

The present specification discloses compounds, compositions, and methods for treating an individual suffering from diseases associated with aberrant immune responses, such as neurodegenerative or autoimmune disorders or inflammation-associated diseases. This is accomplished by administering a therapeutically effective amount of an immunosuppressive Tat derivative polypeptide or composition comprising such polypeptides to an individual suffering from the disease. As disclosed herein, the disclosed immunosuppressive Tat derivative polypeptides have demonstrated immunosuppressive activity.

Disclosed herein are immunosuppressive trans-activator of transcription (Tat) derivative polypeptides comprising an amino acid sequence comprising the following domains in the indicated order; a transcription factor (TF) domain comprising a sequence from an immunosuppressive human immunodeficiency virus (HIV), SIV Tat protein, hairless or an artificial immunosuppressive sequence; a cysteine-rich region from lentiviral Tat or a defensin molecule; and a C-terminal region from a lentiviral Tat protein.

In another embodiment, the immunosuppressive Tat derivative polypeptide, further comprising an arginine-rich domain from a lentiviral Tat protein. In another embodiment, the TF domain further comprises a repeat sequence comprising $(PVDPRLEPWKHPGSQP)_n$ at the N-terminus, wherein n=2-10. In another embodiment, at least one of the amino acids in the TF domain is modified with a conservative amino acid substitution.

In another embodiment of the immunosuppressive Tat derivative polypeptide, HIV is HIV-1 or HIV-2. In another embodiment, the lentiviral Tat is from HIV-1, HIV-2, SIV, FIV, BIV, or EIAV.

In another embodiment of the immunosuppressive Tat derivative polypeptide, the TF domain comprises an amino acid sequence of one of SEQ ID NOs: 36, 39, 44, 48, 50, 54, 59, 60, or 61. In another embodiment, the cysteine-rich domain comprises an amino acid sequence of one of SEQ ID NOs:37, 40, 41, 43, 45, 47, 49, 51, 53, 55, 57, 58, 62, 63, 64, or 70. In another embodiment, the C-terminal domain comprises an amino acid sequence of one of SEQ ID NOs:38, 42, 46, 47, 49, 52, 53, 68, or 71. In yet another embodiment, both the cysteine-rich region and the C-terminal region are from the same source and the amino acid sequence of the combined cysteine-rich and C-terminal region is one of SEQ ID NOs:47, 49, or 53. In another embodiment, the immunosuppressive Tat derivative polypeptide has greater than 85% sequence identity, greater than 90% sequence identity, or greater than 95% sequence identity to one of SEQ ID NOs:9-11, 13-35, or 69.

Also disclosed herein is a pharmaceutical composition comprising one or more of an immunosuppressive Tat derivative polypeptides and a pharmaceutically acceptable excipient. In another embodiment, the immunosuppressive Tat derivative polypeptide has greater than 85% sequence identity to one or more of SEQ ID NOs:9-11, 13-35, or 69.

Further disclosed herein is a method of treating a disease characterized by aberrant immune responses, the method comprising: administering a therapeutically effective amount of one or more of the immunosuppressive Tat derivative polypeptides to a subject in need thereof; and thereby treating the disease by suppressing the immune system.

Further disclosed herein is a method of increasing the expression of Fas ligand (FasL) on antigen presenting cell regulatory macrophages (ARegs), the method comprising: administering a therapeutically effective amount of one or more of the immunosuppressive Tat derivative polypeptides to a subject; and thereby increasing the expression of FasL on the ARegs.

Further disclosed herein is a method of reducing inflammation, the method comprising: administering a therapeutically effective amount of one or more of the immunosuppressive Tat derivative polypeptides to a subject in need thereof; and thereby increasing reducing inflammation in the subject.

In one embodiment of the methods disclosed herein, the immunosuppressive Tat derivative polypeptide has greater than 85% sequence identity to one of SEQ ID NOs:9-11, 13-35, or 69.

In another embodiment of the methods, the treatment increases the expression of Fas ligand on antigen presenting cell regulatory macrophages (ARegs). In yet another embodiment, the ARegs are CD14+ macrophages.

In another embodiment of the methods, the disease is an autoimmune, neurodegenerative or inflammation-associated disorder. In one embodiment, the autoimmune disorder is an acute disseminated encephalomyelitis (ADEM), an Addison's disease, an allergy, allergic rhinitis, an Alzheimer's disease, an anti-phospholipid antibody syndrome (APS), an arthritis, an asthma, an autoimmune deficiency syndrome, an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an eczema, an endometriosis, a gastrointestinal disorder, a Goodpasture's syndrome, a Graves' disease, a Guillain-Barré syndrome (GBS), a Hashimoto's thyroiditis, a hidradenitis suppurativa, an idiopathic thrombocytopenic purpura, an inflammatory bowel disease, an inflammatory dermatologic disease, an interstitial cystitis, a lupus, a morphea, a multiple sclerosis (MS), a myasthenia gravis, a myopathy, a narcolepsy, a neuromyotonia, a pemphigus vulgaris, a pernicious anaemia, a primary biliary cirrhosis, a psoriasis, a recurrent disseminated encephalomyelitis, a rheumatic fever, a schizophrenia, a scleroderma, a Sjögren's syndrome, a skin disorder, a tenosynovitis, a uveitis, a vasculitis, or a vitiligo. In another embodiment, the disease associated with inflammation is an acne, an acid reflux/heartburn, an allergy, an allergic rhinitis, an Alzheimer's disease, an appendicitis, an arteritis, an arthritis, an asthma. an atherosclerosis, an autoimmune disorder, a balanitis, a blepharitis, a bronchiolitis, a bronchitis, a bursitis, a cancer, a carditis, a celiac disease, a cellulitis, a cervicitis, a cholangitis, a cholecystitis, a chorioamnionitis, a chronic obstructive pulmonary disease (COPD), a cirrhosis, a colitis, a conjunctivitis, a cystitis, a common cold, a dacryoadenitis, a dementia, a dermatitis, a dermatomyositis, an eczema, an emphysema, an encephalitis, an endocarditis, an endometritis, an enteritis, an enterocolitis, an epicondylitis, an epididymitis, a fasciitis, a fibrositis, a gastritis, a gastroenteritis, a gingivitis, a glomerulonephritis, a glossitis, a heart disease, a hepatitis, a hidradenitis suppurativa, a high blood pressure, an ileitis, an insulin resistance, an interstitial cystitis, an iritis, an ischemic heart disease, a keratitis, a keratoconjunctivitis, a laryngitis, a lupus, a mastitis, a mastoiditis, a meningitis, a metabolic syndrome (syndrome X), a migraine, a multiple sclerosis, a myelitis, a myocarditis, a myopathy, a myositis, a nephritis, a neuropathy, an obesity, an omphalitis, an oophoritis, an orchitis, an osteochondritis, an osteopenia, an osteoporosis, an osteitis, an otitis, a pancreatitis, a Parkinson's disease, a parotitis, a pelvic inflammatory disease, a pericarditis, a peritonitis, a pharyngitis, a phlebitis, a pleuritis, a pneumonitis, a proctitis, a prostatitis, a psoriasis, a pulpitis, a pyelonephritis, a pylephlebitis, a rheumatic fever, a rhinitis, a salpingitis, a sialadenitis, a sinusitis, a spastic colon, a stomatitis, a synovitis, a tendonitis, a tendinosis, a tenosynovitis, a thrombophlebitis, a tonsillitis, a trigonitis, a tumor, an urethritis, an uveitis, a vaginitis, a vasculitis, or a vulvitis. In yet another embodiment, the neurodegenerative disease is Alexander disease, Alper's disease, Alzheimer's disease, amyloidoses, amyotrophic lateral sclerosis, anxiety, ataxia telangiectasia, attention deficit disorders, Canavan disease, central nervous system injuries, Charcot Marie Tooth disease, Cockayne syndrome, corticobasal degeneration, Creutzfeldt-Jakob disease, depression, encephalitis (e.g., bacterial, parasitic, fungal, or viral), Friedreich's ataxia frontotemporal dementia, hereditary spastic paraparesis, Guillain-Barre syndrome (and its variants acute motor axonal neuropathy, acute inflammatory demyelinating polyneuropathy, and Fisher syndrome), HIV/AIDS dementia complex, Huntington's disease, ischemic damage to the nervous system, Kennedy's disease, Krabbe disease, Lewy body dementia, Machado-Joseph disease, meningitis (e.g., bacterial, parasitic, fungal, or viral) multiple sclerosis, multiple system atrophy, neural trauma, e.g., percussive brain damage, spinal cord injury and traumatic damage to the nervous system, a neuropathy such as e.g., chemotherapy-induced neuropathy, diabetes-associated neuropathy, and peripheral neuropathy, Parkinson's disease, Pelizaeus-Merzbacher disease, Pick's disease, primary lateral sclerosis, prion disorders, progressive supranuclear palsy, Refsum's disease, Sandhoff disease, schizophrenia, Schilder's disease, spinocerebellar atrophies, Steele-Richardson-Olszewski disease, stroke, tabes dorsalis, or vascular dementia.

In yet another embodiment of the methods, the administration further causes the reduction of at least one symptom associated with the autoimmune disease, neurodegenerative disease, or disease associated with inflammation and therein the symptom is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue.

In another embodiment of the methods, the subject is not immunocompromised. In another embodiment, the immune system of the subject is not compromised as a result of the administration. In yet another embodiment, as a result of the administration, secretion of cytokines by ARegs is decreased.

In another embodiment of the methods, the immunosuppressive Tat derivative polypeptide is administered in a plurality of doses. In another embodiment, the immunosuppressive Tat derivative polypeptide is administered daily, weekly, biweekly, monthly, or bimonthly. In yet another embodiment, the administering step comprises a repetitive administration cycle wherein each cycle comprises administering a plurality of doses of the immunosuppressive Tat derivative polypeptide in a defined time period followed by a rest period and wherein the cycle is repeated a plurality of times.

Also disclosed herein is the use of one or more immunosuppressive Tat derivative polypeptides in the manufacture of a medicament for treatment of a disease characterized by aberrant immune responses in a subject in need thereof; wherein the one or more immunosuppressive Tat derivative polypeptides are at least 85% identical to an immunosuppressive Tat derivative polypeptide of claim 1, and wherein administration of the immunosuppressive Tat derivative polypeptide treats the disease by suppressing the immune system in the subject.

Further disclosed herein is the use of one or more immunosuppressive Tat derivative polypeptides in the manufacture of a medicament for increasing the expression of Fas ligand (FasL) on antigen presenting cell regulatory macrophages (ARegs) in a subject wherein the one or more immunosuppressive Tat derivative polypeptides are at lest 85% identical to an immunosuppressive Tat derivative polypeptide of claim 1, wherein administration of the immunosuppressive Tat derivative polypeptides increases the expression of FasL on the ARegs.

Further disclosed herein is the use of one or more immunosuppressive Tat derivative peptides in the manufacture of a medicament for reducing inflammation in a subject, the one or more immunosuppressive Tat derivative polypeptides are at least 85% identical to an immunosuppressive Tat derivative polypeptide of claim 1, and wherein administration of the immunosuppressive Tat derivative polypeptides reduces inflammation in the subject.

In another embodiment of the use, the treatment increases the expression of Fas ligand on antigen presenting cell regulatory macrophages (ARegs). In another embodiment, the ARegs are CD14+ macrophages. In another embodiment, secretion of cytokines by ARegs is decreased. In yet another embodiment, the subject is not immunocompromised. In yet another embodiment, the immune system of the subject is not compromised as a result of the administration.

In yet another embodiment of the use, the immunosuppressive Tat derivative polypeptide has greater than 85% sequence identity to one of SEQ ID NOs:9-11, 13-35, or 69.

In another embodiment of the use, the disease is an autoimmune, neurodegenerative or inflammation-associated disorder. In another embodiment, the autoimmune disorder is an acute disseminated encephalomyelitis (ADEM), an Addison's disease, an allergy, allergic rhinitis, an Alzheimer's disease, an anti-phospholipid antibody syndrome (APS), an arthritis, an asthma, an autoimmune deficiency syndrome, an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an eczema, an endometriosis, a gastrointestinal disorder, a Goodpasture's syndrome, a Graves' disease, a Guillain-Barré syndrome (GBS), a Hashimoto's thyroiditis, a hidradenitis suppurativa, an idiopathic thrombocytopenic purpura, an inflammatory bowel disease, an inflammatory dermatologic disease, an interstitial cystitis, a lupus, a morphea, a multiple sclerosis (MS), a myasthenia gravis, a myopathy, a narcolepsy, a neuromyotonia, a pemphigus vulgaris, a pernicious anaemia, a primary biliary cirrhosis, a psoriasis, a recurrent disseminated encephalomyelitis, a rheumatic fever, a schizophrenia, a scleroderma, a Sjögren's syndrome, a skin disorder, a tenosynovitis, a uveitis, a vasculitis, or a vitiligo. In another embodiment, the disease associated with inflammation is an acne, an acid reflux/heartburn, an allergy, an allergic rhinitis, an Alzheimer's disease, an appendicitis, an arteritis, an arthritis, an asthma. an atherosclerosis, an autoimmune disorder, a balanitis, a blepharitis, a bronchiolitis, a bronchitis, a bursitis, a cancer, a carditis, a celiac disease, a cellulitis, a cervicitis, a cholangitis, a cholecystitis, a chorioamnionitis, a chronic obstructive pulmonary disease (COPD), a cirrhosis, a colitis, a conjunctivitis, a cystitis, a common cold, a dacryoadenitis, a dementia, a dermatitis, a dermatomyositis, an eczema, an emphysema, an encephalitis, an endocarditis, an endometritis, an enteritis, an enterocolitis, an epicondylitis, an epididymitis, a fasciitis, a fibrositis, a gastritis, a gastroenteritis, a gingivitis, a glomerulonephritis, a glossitis, a heart disease, a hepatitis, a hidradenitis suppurativa, a high blood pressure, an ileitis, an insulin resistance, an interstitial cystitis, an iritis, an ischemic heart disease, a keratitis, a keratoconjunctivitis, a laryngitis, a lupus, a mastitis, a mastoiditis, a meningitis, a metabolic syndrome (syndrome X), a migraine, a multiple sclerosis, a myelitis, a myocarditis, a myopathy, a myositis, a nephritis, a neuropathy, an obesity, an omphalitis, an oophoritis, an orchitis, an osteochondritis, an osteopenia, an osteoporosis, an osteitis, an otitis, a pancreatitis, a Parkinson's disease, a parotitis, a pelvic inflammatory disease, a pericarditis, a peritonitis, a pharyngitis, a phlebitis, a pleuritis, a pneumonitis, a proctitis, a prostatitis, a psoriasis, a pulpitis, a pyelonephritis, a pylephlebitis, a rheumatic fever, a rhinitis, a salpingitis, a sialadenitis, a sinusitis, a spastic colon, a stomatitis, a synovitis, a tendonitis, a tendinosis, a tenosynovitis, a thrombophlebitis, a tonsillitis, a trigonitis, a tumor, an urethritis, an uveitis, a vaginitis, a vasculitis, or a vulvitis. In yet another embodiment, the neurodegenerative disease is Alexander disease, Alper's disease, Alzheimer's disease, amyloidoses, amyotrophic lateral sclerosis, anxiety, ataxia telangiectasia, attention deficit disorders, Canavan disease, central nervous system injuries, Charcot Marie Tooth disease, Cockayne syndrome, corticobasal degeneration, Creutzfeldt-Jakob disease, depression, encephalitis (e.g., bacterial, parasitic, fungal, or viral), Friedreich's ataxia frontotemporal dementia, hereditary spastic paraparesis, Guillain-Barre syndrome (and its variants acute motor axonal neuropathy, acute inflammatory demyelinating polyneuropathy, and Fisher syndrome), HIV/AIDS dementia complex, Huntington's disease, ischemic damage to the nervous system, Kennedy's disease, Krabbe disease, Lewy body dementia, Machado-Joseph disease, meningitis (e.g., bacterial, parasitic, fungal, or viral), multiple sclerosis, multiple system atrophy, neural trauma, e.g., percussive brain damage, spinal cord injury and traumatic damage to the nervous system, a neuropathy such as e.g., chemotherapy-induced neuropathy, diabetes-associated neuropathy, and peripheral neuropathy, Parkinson's disease, Pelizaeus-Merzbacher disease, Pick's disease, primary lateral sclerosis, prion disorders, progressive supranuclear palsy, Refsum's disease, Sandhoff disease, schizophrenia, Schilder's disease, spinocerebellar atrophies, Steele-Richardson-Olszewski disease, stroke, tabes dorsalis, or vascular dementia.

In another embodiment of the use, the immunosuppressive Tat derivative polypeptide further causes the reduction of at least one symptom associated with the autoimmune disease, neurodegenerative disease, or disease associated with inflammation and therein the symptom is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue.

In another embodiment of the use, the immunosuppressive Tat derivative polypeptide is administered in a plurality of doses. In another embodiment, the immunosuppressive Tat derivative polypeptide is administered daily, weekly, biweekly, monthly, or bimonthly. In yet another embodiment, the administering step comprises a repetitive administration cycle wherein each cycle comprises administering a plurality of doses of the immunosuppressive Tat derivative polypeptide in a defined time period followed by a rest period and wherein the cycle is repeated a plurality of times.

BRIEF DESCRIPTION OF DRAWINGS

FIG. 1A-B depicts fluorescence activated cell sorter (FACS) analysis of the results of Tat activation of monocytes. Human peripheral blood monocytes were committed to differentiate into dendritic cells (DC) through five days of culture in GM-CSF and IL-4. Committed DCs were cultured overnight either in medium alone (control), lipopolysaccharide (LPS), or Tat, after which they were stained with an anti-CD86 antibody and analyzed by FACScan for CD86, a specific marker of DC activation, induction (FIG. 1A) or generalized activation (FIG. 1B, enlargement into box R2, shown for Tat-stimulated cells).

(FIG. 9A) Human peripheral blood mononuclear cells (PBMC) from one individual (PBMCs #3) cultured for five days in either medium with tetanus antigen (Ag), antigen with the further addition of Tat (Ag+Tat) or Ag with Tat and recombinant sFas protein (Ag+Tat+sFas). The results are graphed as stimulation index (mean cpm stimulated culture/mean cpm medium control). (FIG. 9B) Proliferation of PBMCs cultured 6 days with either tetanus or Candida antigen alone (Ag), compared with cultures in which Tat (Ag+Tat), or Tat and the antagonistic anti-Fas antibody, ZB4, were added (Ag+Tat+αFas).

FIG. 11 depicts a dose-response curve of stimulation of human monocytes with Tat derivatives.

FIG. 17E depicts the data from FIGS. 27A-D in graphical format.

DESCRIPTION

Figure 2:
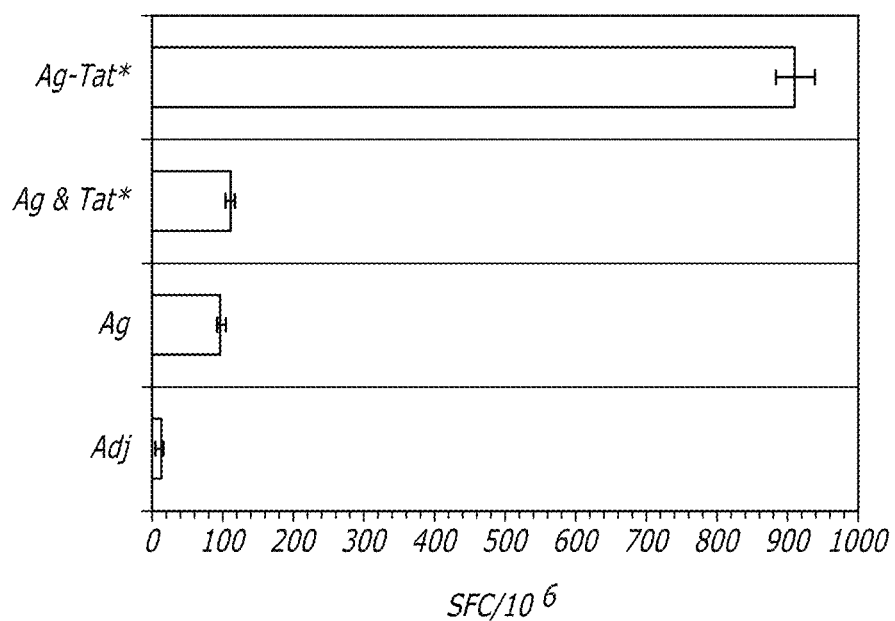
FIG. 2 depicts the enhancement of antigen-specific activation of cytotoxic T lymphocytes (CTL) by Tar-antigen (Ag) complexes. CTL activity was quantitated as the number of γ-interferon-secreting spot-forming colonies (SFC)/$10^6$ plated cells using ELISPOT assays.

The present specification relates to compounds, compositions, and methods for treating an individual suffering from diseases associated with aberrant immune responses, such as autoimmune disorders including neurodegenerative disorders, or inflammation-associated disorders. This is accomplished by administering a therapeutically effective amount of an immunosuppressive Tat derivative polypeptide or composition comprising such polypeptides to an individual suffering from the diseases. As disclosed herein, the disclosed immunosuppressive Tat derivative polypeptides have anti-inflammatory activities. The immunosuppressive derivative peptides within the scope of the present disclosure are immunosuppressive.

As used herein the term "aberrant immune responses" refers to increased, undesirable, excessive, or inappropriate immune responses in which the immune response to antigens, such as self antigens, is increased such that inflammation and/or autoimmune disease or neurodegenerative disease is seen. Aberrant immune responses, as used herein, are characterized by an immune cascade resulting in destruction of the body's tissue. Typically, an aberrant immune result is not seen in a normal response to infection but can be triggered by infection.

The HIV Tat protein is a variable RNA binding peptide of 86-110 amino acids in length that is encoded on two separate exons of the HIV genome. Based on molecular analysis, the Tat protein (SEQ ID NO:2) encodes distinct and linked peptide activities. This present disclosure describes polypeptide compositions that are derivatized from the canonical HIV-1 Tat structure in at least at the first or amino terminal portion, in a manner to enhance the immunotherapeutic potential of the polypeptide. The amino terminal portion of Tat includes a short peptide region from a nuclear transcription factor (TF) typically flanked by proline residues. This region determines, at least in part, how stimulatory or how suppressive the Tat polypeptide is for cells of the immune system, particularly innate immune cells such as dendritic cells (DC) and macrophages (antigen-presenting cells or APCs). Consequently, it is predicted that modifications to the TF region can render the polypeptides more active in the therapy of disease.

Previous studies determined that HIV Tat is immunosuppressive in the majority of human HIV strains. However, in long-term non-progressors (LTNP), a subset of HIV-infected individuals with high viral loads who do not have a significant reduction in T4 cells and do not progress to Acquired Immunodeficiency Syndrome (AIDS), the HIV Tat protein is immunostimulatory. The Tat protein found in LTNP is capable of trans-activating viral RNA; however, LTNP Tat (designated herein after as "IS-Tat" for immunostimulatory Tat) does not induce apoptosis in T4 cells or macrophages and is not immunosuppressive. Moreover, T4 cells infected ex vivo with HIV isolated from LTNP (such cell lines are designated "Tat TcL") overexpress IS-Tat proteins, often to the virtual exclusion of other viral proteins, that are strongly growth promoting rather than pro-apoptotic. The tat genes cloned from these Tat TcLs reveal sequence variations in two tat regions, at the amino terminus and within the first part of the second exon.

Based on molecular analysis, the HIV Tat protein (SEQ ID NO:2) contains three distinct regions of interest. The first region of interest is the transduction domain at the amino terminus of Tat (amino acids 3-19). A second region of interest is a cysteine-rich ligand binding domain (amino acids 22-37) which contains seven conserved cysteines. A third region of interest is the membrane translocation sequence (MTS) which encompasses amino acids 47-57.

The proline rich stretch near the amino terminus (amino acids 3-19) of HIV-1 and HIV-2 Tat within the transduction domain is an SH3 binding domain having significant homology to the SH3-binding domain of the mouse hairless (hr) gene. The SH3 binding domain presents an important target for pharmaceutical development with the potential for the diagnosis, prophylaxis and treatment of undesirable cellular processes such as autoimmunity.

Unexpectedly, mice expressing the hr gene mutation develop an AIDS-like syndrome characterized by poor CTL function, a shift in helper T lymphocytes from those regulating cell-mediated immunity (TH1) to those regulating antibody-mediated immunity (TH2), and increased susceptibility to chemical and ultraviolet light-induced skin cancers. Additionally, variants of Tat are found in retrovirus-infected monkeys which do not develop immunodeficiency and that do not have epidemic infection. However, these variant Tat do not have the SH3 binding domain and instead substitute a different sequence, also set off by prolines at either end of the sequence, into the transduction domain. Therefore, the SH3 binding domain is central to the immunosuppressive activity of Tat. Genetic data indicates the SH3 binding domain regulates monocyte differentiation into antigen-presenting cell regulatory macrophages (ARegs). In Tat proteins which do not contain this SH3 domain, or this domain is mutated, monocyte differentiation is directed into DCs which stimulate CTL responses The MTS region permits Tat to freely traffic across the endosomal membrane into the cytoplasm following receptor binding, where it transactivates gene expression, including but not restricted to, genes of HIV-1. The MTS has been wrongly assumed to facilitate Tat entrance into the cell, which it can only accomplish at high concentrations that have been impossible to attain in vivo.

Unlike the current immunosuppressive therapies, the disclosed Tat-based compositions, the immunosuppressive Tat derivative polypeptides, have the potential to suppress antigen-specific immune responses without immunocompromising the patient. They preserve the immunosuppressive activity of conventional HIV Tat in the absence of the virus and therefore the immunosuppressive Tat derivatives modulate the specificity of the immune response, a key component to the bodies natural defense This is particularly important when chronic immunosuppressive therapy is needed, such as in autoimmune, neurodegenerative, or inflammation-associated diseases.

Figure 3:
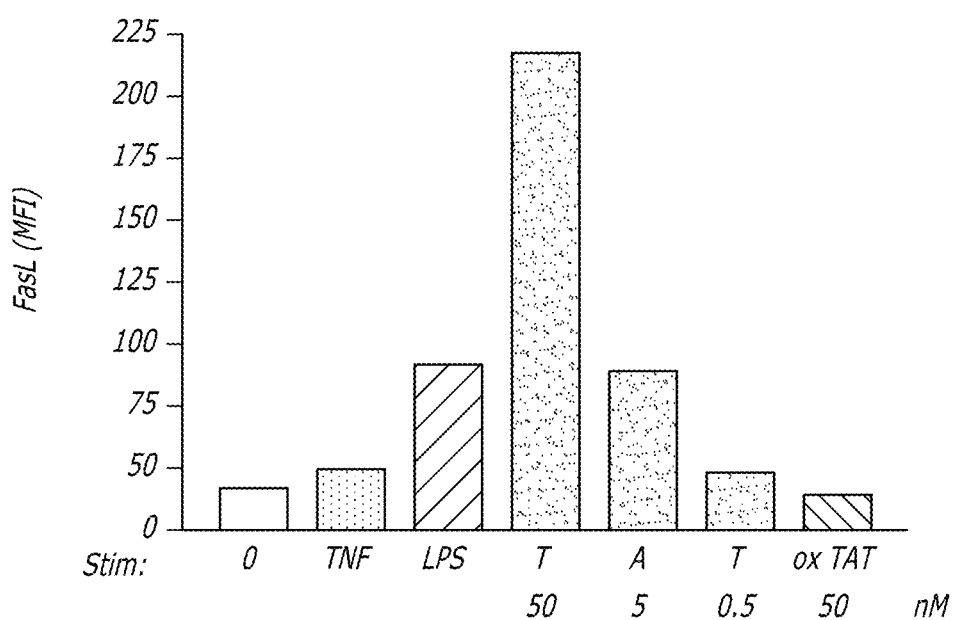
FIG. 3 depicts median fluorescence of monocytes, cultured for six days either with no stimulus (0), tumor necrosis factor-alpha (TNF-α), LPS, decreasing concentrations of C-Tat (conventional native immunosuppressive Tat from HIV), or oxidized C-Tat (ox-C-Tat) and stained with an anti-Fas ligand (FasL) monoclonal antibody (Mab) followed by a fluoresceinated goat anti-mouse polyclonal antibody.

The immunosuppressive effects of Tat are mediated by macrophages. When stimulated by Tat, either by natural HIV-1 infection or by Tat uptake, macrophages induce the Fas ligand (FasL), which in turn induces the programmed cell death (apoptosis) of antigen-reacting, Fas-expressing helper T cells (FIG. 3). Tat enhances the viability of cultured murine macrophages as long as the macrophages were first activated in vivo compared with no prior activation and stimulated with relatively high concentrations of Tat. By comparison, LPS promotes the viability of murine macrophages independently from in vivo stimulation, and at the same concentration effective for human macrophages. Certain of the Tat-based compositions disclosed herein produce a stable suppression of mouse lymphocyte proliferation and may also serve to suppress an antigen-specific immune response to a variety of antigens.

The macrophages responsible for these responses have been identified as antigen presenting cell regulatory macrophages (ARegs). ARegs are also known as "alternatively activated" macrophages. ARegs are stable macrophages expressing FasL and secreting the cytokines IL-10 and IL-6. AReg are stable and respond in an autocrine and paracrine manner to these two cytokines, as well as in a paracrine manner to IL-4. These cytokines accumulate and switch the immune response from TH1 (based on helper T lymphocytes) to TH2 (based on suppressive T lymphocytes). As these cytokines build up, they overwhelm and suppress the immune response and explain why immune responses are normally self-limiting in an antigen-specific manner.

An unexpected observation is that 1,000 fold lower concentrations of Tat (500 pM) trigger this effect on the macrophages, as compared with the concentration required to initiate direct apoptosis of CD4+ T cells (approximately 500 nM). Therefore, at concentrations of Tat achievable as a systemically administered immunomodulator, the macrophage effect will preferentially occur over the T cell effect.

The Tat-mediated antigen-specific suppression is mediated through trans-(intracellular) activation of a CD14+ FasL+ macrophage. Tat-activated macrophages are immunosuppressive ARegs. At low concentrations of Tat (50 nM), Tat-induced immunosuppression was not only fully reversed by the addition of soluble Fas, but under these conditions, Tat actually became slightly stimulatory (relative to antigen treatment alone). Antibodies to FasL reversed Tat immunosuppression of tetanus responses and enhanced the *Candida* response relative to Tat treatment alone. Suppression could be fully reversed (>95% of control) with the further addition of anti-IL-10 and anti-IL-6 antibodies to the cultures, both cytokines deriving from macrophages under these culture conditions. A portion of Tat-induced immunosuppression is contributed by induction of FasL, although other Tat-induced factors can participate in suppressing T cell proliferative responses, especially at higher concentrations of Tat.

The complete amino acid sequence of HIV-1 Tat encoded by exons 1 and 2 of the Tat gene is listed below:

```
ATG GAG CCC GTG GAC CCT CGC CTG GAG CCC TGG AAG CAC CCG GGC AGC

Met Glu Pro Val Asp Pro Arg Leu Glu Pro Trp Lys His Pro Gly Ser
1           5                   10/30            15

CAG CCC AAG ACC GCC TGC ACC ACA TGT TACT GC AAG AAG TGC TGC TTC

Gln Pro Lys Thr Ala Cys Thr Thr Cys Tyr Cys Lys Lys Cys Cys Phe
            20/60               25              30/90

CAC TGC CAG GTG TGC TTC ACC AAG AAG GCC TTG GGC ATC AGC TAC GGC

His Cys Gln Val Cys Phe Thr Lys Lys Ala Leu Gly Ile Ser Tyr Gly
        35                  40/120              45

CGC AAG AAG CGC CGG CAG CGC CGC CGG GCC CCT GAG GAC AGC CAG ACC

Arg Lys Lys Arg Arg Gln Arg Arg Arg Ala Pro Glu Asp Ser Gln Thr
       50/150           55                  60/180

CAC CAG GTG AGC CCT CCC AAG CAG CCC GCT CCA CAG TTC CGC GGC GAC

His Gln Val Ser Pro Pro Lys Gln Pro Ala Pro Gln Phe Arg Gly Asp
65              70/210           75                  80/240

CCT ACC GGT CCC AAG GAG AGC AAG AAG AAG GTG GAG CGC GAG ACC GAG

Pro Thr Gly Pro Lys Glu Ser Lys Lys Lys Val Glu Arg Glu Thr Glu
                85              90/270           95

SEQ ID NO: 1
ACC CAT CCC GTC GAC

SEQ ID NO: 2
Thr His Pro Val Asp
            100/300
```

Tat has a proline (P) rich segment near the amino terminus (amino acids 3-19, underlined above). This highly conserved region of HIV-1 Tat is a canonical SH3 binding domain also referred to herein as a nuclear transcription factor (TF) domain. The mouse hairless (hr) gene also has an SH3 binding motif (TF, amino acids 176-196 of hr [SEQ ID NO:72]). Homology exists between the human Tat SH3 binding domain (SEQ ID NO:4) and the SH3 binding domain of the mouse hr gene:

```
Human 3
Pro Val Arg Pro Asn Leu Glu Pro Trp Lys His Pro Gly Ser Gln Pro 18

Mouse 180
Pro Leu Thr Pro Asn ------- Pro Trp Val Tyr Ser Gly Ser Gln Pro 193
```

Variants of Tat found in simian retroviruses, which do not cause immunodeficiency, do not have an SH3 binding domain but instead have the following proline-flanked sequence:

```
                                                    (SEQ ID NO: 3)
Pro Leu Arg Glu Gln Glu Asn Ser Leu Glu Ser Ser

Asn Glu Arg Ser Ser Cys Ile Leu Glu Ala Asp Ala

Thr Thr Pro
```

The human equivalent of the simian sequence (SEQ ID NO:3) above is:

```
                                                    (SEQ ID NO. 4)
Ser Asn Glu Arg Ser Ser Cys Glu Leu Glu Val
```

Another region of interest is a cysteine-rich proposed ligand binding domain (amino acids 22-37) which contains seven cysteines.

```
                                                    (SEQ ID NO: 5)
Cys Thr Thr Cys Tyr Cys Lys Lys Cys Cys Phe His

Cys Gln Val Cys
```

Derivatives of Tat, generated through modulating the signal transduction motif defined by the SH3 binding domain, drive differentiation predominantly to dendritic cells or immunosuppressive AReg. AReg are also critical contributors to invasion of gastric, pancreas, and ductal infiltrating breast tumors, as well as components of tolerance in organ transplantation. The two external prolines at positions 3 and 18 flanking the SH3 domain are maintained in order to facilitate the proper structure for SH3 binding. In addition, the transduction domain from a non-immunosuppressive human variant Tat, or the domain from the hr mutation, can replace amino acids 3-19 of Tat, although the hr sequence is predicted to increase suppression. In addition, the stimulatory simian form of Tat (SEQ ID NO:3), or its human equivalent sequence (SEQ ID NO:4), can be substituted at this domain. Additional chemical modifications, such as ox-Tat (chemically oxidized Tat as disclosed in US 2006/0160183, incorporated by reference for all it contains regarding Tat derivatives), can be used for stimulation of dendritic/CTL responses.

In one embodiment disclosed herein, the immunosuppressive Tat derivative comprises a Tat peptide in which amino acids 3-19 are altered. These alterations include replacement of individual amino acids with alternate amino acids or replacement of all of amino acids 3-19 with another sequence. Tat peptides suitable for use in constructing the disclosed immunosuppressive Tat derivatives include Tat from HIV-1 variants, HIV-2 variants, and SIV variants. SIV variants can be from any species of primate that is infected with SIV as listed in Table 4. Also useful are immunosuppressive lentiviral Tat sequences from non-primate species including, but not limited to, feline (Tat from feline immunodeficiency virus, FIV), bovine, (Tat from bovine immunodeficiency virus, BIV), or equine (Tat from equine infectious anemia virus, EIAV). For the purposes of the instant disclosure, the term "variants" refers to peptides corresponding to the sequence of different strains, naturally occurring or mutated, of the indicated viruses.

SH3 binding proteins contain a series of internal prolines required for nuclear transcription factor (TF) function. In certain embodiments, the internal prolines are each substituted by alanine, rendering the SH3-binding site inactive.

Exemplary immunosuppressive Tat derivatives within the scope of the present disclosure are presented in Table 1. In general, an immunosuppressive Tat derivative polypeptide for the treatment of inflammation, autoimmune disorders, and neurodegeneration comprises three regions. The first region is a derivatized TF, the second region is a cysteine-rich region, and the third region is a C-terminal Tat region.

The TF region, cysteine-rich region, and a C-terminal region are arranged in the Tat derivative polypeptide in that order. The TF region may be derived from a source including, but not limited to, HIV-1 Tat, HIV-2 Tat, SIV Tat, the hairless gene, or an artificial immunosuppressive sequences. The cysteine-rich region may be from a lentivirus Tat, or cysteine rich defensin molecule. The C-terminal region may be derived from lentivirus Tat. Additionally, the Tat derivative C-terminal regions may contain therein an arginine-rich region from HIV-1 Tat, HIV-2 Tat, or SIV Tat (also referred to as the membrane translocation sequence).

As used herein, the term "defensin molecule" refers to small cysteine-rich cationic proteins found in both vertebrates and invertebrates. Defensins comprise 18-45 amino acids including six to eight conserved cysteine residues. Defensins are classified in three groups, α-defensins, β-defensins and θ-defensins.

In another embodiment, the TF region further contains a repeat sequence including, but not limited to, (PVDPRLEPWKHPGSQP)$_n$ (SEQ ID NO:12) wherein n=2-10 at the N-terminus. Furthermore, the repeat sequence can be separated from the N-terminus of an immunosuppressive Tat derivative polypeptide by one or more amino acids acting as a spacer.

In another embodiment, the amino acid sequence of the TF region is one of SEQ ID NOs:36, 39, 44, 48, 50, 54, 59, 60, or 61. In another embodiment, the amino acid sequence of the cysteine-rich region is one of SEQ ID NOs:37, 40, 41, 43, 45, 47, 49, 51, 53, 55, 57, 58, 62, 63, 64 or 70. In another embodiment, the amino acid sequence of the C-terminal region is one of SEQ ID NOs:38, 42, 46, 47, 49, 52, 53, 68 or 71. In yet another embodiment, both the cysteine-rich region and the C-terminal region are from the same source and the amino acid sequence of the cysteine-rich/C-terminal region is one of SEQ ID NO:47, 49, or 53.

In additional embodiments, one or more amino acids, including but not limited to proline, in the TF domain is deleted or substituted with a conservative amino acid substitution.

In additional embodiments the use of conservatively modified variants of the immunosuppressive Tat derivatives is provided. The variants described herein maintain the biological activity of the parent or source molecule.

TABLE 1

| SEQ ID NO. | Amino Acid Sequence | Source† (SEQ ID NO:) | | |
|---|---|---|---|---|
| | | TF region | cysteine-rich region | C-terminal region |
| 6 (Nani-P1) | MEPVDANLEAWKHAGSQPRKTACTTCYCKKCCFHCQVCFTRKGL GISYGRKKRRQRRRAPQDSQTHQASLSKQPASQSRGDPTGPTES KKKVERETETDPFD | HIV-1 SEQ ID NO: 59 | HIV-1 SEQ ID NO: 62 | HIV-1 SEQ ID NO: 42 |
| 7 (Nani-P2) | MDPKGEEDQDVSHQDLIKQYRKPRTACNNCYCKKCCFHCYACFL RKGLGITYHAFRTRRKKIASADRIPVPQQSISIRGRDSQTTQESQK KVEEQAKANLRISRKNLGDETRGPVGAGN | SIVagm$^a$ SEQ ID NO: 60 | HIV-1 SEQ ID NO: 63 | SIVagm SEQ ID NO: 68 |
| 8 (Nani-P3) | METPLKEQENSLESCREHSSSISEVDVPTPVSCLRKGGRCWNRCI GNTRQIGSCGVPFLKCCKRKPFTRKGLGISYGRKKRRQRRRAPQ DSQTHQASLSKQPASQSRGDPTGPTESKKKVERETETDPFD | SIVsmm$^b$ SEQ ID NO: 61 | Murine β-defensin-3 SEQ ID NO: 64 | HIV-1 SEQ ID NO: 42 |
| 9 | MDPIDPDLEPWKHPGSQPETACNNCFCKKCSYHCLVCFQKKGLG ISHGRKKRRQRRSAPPSSEDHQNLISKQPIPRTQGDQTGSEESKK KVESKTETDPFD | SIVcpz$^c$ SEQ ID NO: 39 | HIV-1 SEQ ID NO: 65 | HIV-1 SEQ ID NO: 42 |
| 10 | MEPLTPHPWVYSGGQPKVPTTACSKCYCKICCWHCQLCLKKGLG ISYGRKKRRQRRRAPQDSQTHQASLSKQPASQSRGDPTGPTESK KKVERETETDPFD | Human hr gene SEQ ID NO: 48 | HIV-1 SEQ ID NO: 66 | HIV-1 SEQ ID NO: 42 |
| 11 | MAGPHPVIVITGPHEEPRKTACTTCYCKKCCFHCQVCFTRKGLGIS YGRKKRRQRRRAPQDSQTHQASLSKQPASQSRGDPTGPTESKK KVERETETDPFD | VIVIT$^d$ SEQ ID NO: 50 | HIV-1 SEQ ID NO: 67 | HIV-1 SEQ ID NO: 42 |

TABLE 1-continued

| SEQ ID NO. | Amino Acid Sequence | Source† (SEQ ID NO:) | | |
|---|---|---|---|---|
| | | TF region | cysteine-rich region | C-terminal region |
| 13 | MDPTDPELPPWQQPGSQPPTPRKTACTTCYCKKCCFHCQVCFL QKGLGITYARPRKRAARSISEDDSAPTEPYPGPEGPRQTRRRRRR QWRQRRTQRLYLQQRIFEAIFGSRTAALEDSLQQLQISD | SIVgor[e] SEQ ID NO: 36 | HIV-1 SEQ ID NO: 37 | SIVsyk[f] SEQ ID NO: 38 |
| 14 | MDPIDPDLEPWKHPGSQPETACNNCFCKKCSYHCLVCFLQKGLGI TYARPRKRAARSISEDDSAPTEPYPGPEGPRQTRRRRRRQWRQ RRTQRLYLQQRIFEAIFGSRTAALEDSLQQLQISD | SIVcpz SEQ ID NO: 39 | HIV-1 SEQ ID NO: 40 | SIVsyk SEQ ID NO: 38 |
| 15 | MDPIDPDLEPWKHPGSQPACYCRIPACIAGERRYGTCIYQGRLWA FCCFHCQVCFTRKGLGISYGRKKRRQRRRAPQDSQTHQASLSKQ PASQSRGDPTGPTESKKKVERETETDPFD | SIVcpz SEQ ID NO: 39 | Human α-defensin-1 SEQ ID NO: 41 | HIV-1 SEQ ID NO: 42 |
| 16 | MDPIDPDLEPWKHPGSQPGIGDPVTCLKSGAICHPVFCPRRYKQI GTCGLPGTKCCKKPFHCQVCFTRKGLGISYGRKKRRQRRRAPQD SQTHQASLSKQPASQSRGDPTGPTESKKKVERETETDPFD | SIVcpz SEQ ID NO: 39 | Human β-defensin-2 SEQ ID NO: 43 | HIV-1 SEQ ID NO: 42 |
| 17 | MEPVDPRLEPWKHPGSQPKTACNNCHCKVCCYHCVYCFTKKGL GISYGRKKRRRPARTADKDQDNQDPVSKQSLAGTRSQQE | HIV-1 SEQ ID NO: 44 | SIVcpz SEQ ID NO: 45 | SIVgor SEQ ID NO: 46 |
| 18 | MDPIDPDLEPWKHPGSQPTTACSKCYCKICCWHCQLCLKKGLGIS YGRKKRKHRRGTPQSSKDHQNPIPEQPLPIIRGNPTDPKESKKEV ASKAETDPFD | SIVcpz SEQ ID NO: 39 | HIV-1 SEQ ID NO: 47 | |
| 19 | MEPLTPHPWVYSGGQPKVPETACNNCFCKKCSYHCLVCFQKKGL GISHGRKKRRQRRSAPPSSEDHQNLISKQPIPRTQGDQTGSEESK KKVESKTETDPFD | Human hr gene SEQ ID NO: 48 | HIV-1 SEQ ID NO: 49 | |
| 20 | MAGPHPVIVITGPHEEPTTACSKCYCKICCWHCQLCLKKGLGISYG RKKRKHRRGTPQSSKDHQNPIPEQPLPIIRGNPTDPKESKKEVAS KAETDPFD | VIVIT SEQ ID NO: 50 | HIV-1 SEQ ID NO: 47 | |
| 21 | MAGPHPVIVITGPHEEPETACNNCFCKKCSYHCLVCFQKKGLGIS HGRKKRRQRRSAPPSSEDHQNLISKQPIPRTQGDQTGSEESKKK VESKTETDPFD | VIVIT SEQ ID NO: 50 | HIV-1 SEQ ID NO: 49 | |
| 22 | MEPLTPHPWVYSGGQPKVPRTCHCRSRCLRRESNSGSCNINGRI SSLCCFLKKGLGISYEKSHRRRRTPKKAKANTSSASNEPIPNRIRL CQPKKAKKETVEAAVATAPGLGR | Human hr gene SEQ ID NO: 48 | Myeloid α-defensin-9[g] SEQ ID NO: 51 | SIVmac[h] SEQ ID NO: 52 |
| 23 | MAGPHPVIVITGPHEEPRTCHCRSRCLRRESNSGSCNINGRISSLC CFLKKGLGISYEKSHRRRRTPKKAKANTSSASNEPIPNRIRLCQPK KAKKETVEAAVATAPGLGR | VIVIT SEQ ID NO: 50 | Myeloid α-defensin-9 SEQ ID NO: 51 | SIVmac SEQ ID NO: 52 |
| 24 | MDPIDPDLEPWKHPGSQPRTCHCRSRCLRRESNSGSCNINGRIS SLCCFLKKGLGISYEKSHRRRRTPKKAKANTSSASNEPIPNRIRLC QPKKAKKETVEAAVATAPGLGR | SIVcpz SEQ ID NO: 39 | Myeloid α-defensin-9 SEQ ID NO: 51 | SIVmac SEQ ID NO: 52 |
| 25 | MEPLTPHPWVYSGGQPKVPLEACYNKCYCKRCCYHCQHCFLKK GLGICYEQQRRTPKKTKANTSSASDKSLSRRARNCQPKKEKKET VEAEVATDLGLGR | Human hr gene SEQ ID NO: 48 | SIVsmm SEQ ID NO: 53 | |
| 26 | MAGPHPVIVITGPHEEPLEACYNKCYCKRCCYHCQHCFLKKGLGI CYEQQRRTPKKTKANTSSASDKSLSRRARNCQPKKEKKETVEA EVATDLGLGR | VIVIT SEQ ID NO: 50 | SIVsmm SEQ ID NO: 53 | |
| 27 | MDPIDPDLEPWKHPGSQPLEACYNKCYCKRCCYHCQHCFLKKGL GICYEQQRRTPKKTKANTSSASDKSLSRRARNCQPKKEKKETVE AEVATDLGLGR | SIVcpz SEQ ID NO: 39 | SIVsmm SEQ ID NO: 53 | |
| 28 | MMEPVDPDLPKEQHPPATPRCESCKLGRGRCRKECLENEKPDG RCRLNFLCCFHCQVCFTRKGLGISYGRKKRRQRRRAPQDSQTHQ ASLSKQPASQSRGDPTGPTESKKKVERETETDPFD | SIVmon[i] SEQ ID NO: 54 | β-defensin-105[j] SEQ ID NO: 55 | HIV-1 SEQ ID NO: 42 |
| 29 | MEPLTPHPWVYSGGQPKVPCESCKLGRGRCRKECLENEKPDGR CRLNFLCCFHCQVCFTRKGLGISYGRKKRRQRRRAPQDSQTHQA SLSKQPASQSRGDPTGPTESKKKVERETETDPFD | Human hr gene SEQ ID NO: 48 | β-defensin-105 SEQ ID NO: 55 | HIV-1 SEQ ID NO: 42 |
| 30 | MDPIDPDLEPWKHPGSQPCESCKLGRGRCRKECLENEKPDGRC RLNFLCCFHCQVCFTRKGLGISYGRKKRRQRRRAPQDSQTHQAS LSKQPASQSRGDPTGPTESKKKVERETETDPFD | SIVcpz SEQ ID NO: | β-defensin-105 SEQ ID NO: 55 | HIV-1 SEQ ID NO: 42 |
| 31 | MAGPHPVIVITGPHEEPCESCKLGRGRCRKECLENEKPDGRCRLN FLCCFHCQVCFTRKGLGISYGRKKRRQRRRAPQDSQTHQASLSK QPASQSRGDPTGPTESKKKVERET ETDPFD | VIVIT SEQ ID NO: 50 | β-defensin-105 SEQ ID NO: 55 | HIV-1 SEQ ID NO: 42 |

TABLE 1-continued

| SEQ ID NO. | Amino Acid Sequence | Source† (SEQ ID NO:) | | |
|---|---|---|---|---|
| | | TF region | cysteine-rich region | C-terminal region |
| 32 | MEPVDPRLEPWKHPGSQPPEPVDPRLEPWKHPGSQPKTACNNC HCKVCCYHCVYCFFHCQVCFTRKGLGISYGRKKRRQRRRAPQDS QTHQASLSKQPASQSRGDPTGPTESKKKVERETETDPFD | HIV-1 SEQ ID NO: 56 | SIVcpz SEQ ID NO: 57 | HIV-1 SEQ ID NO: 42 |
| 33 | MEPLTPHPWVYSGGQPKVPLRCICRRGICRLLQRRYGSCAFPGR LYRICCFLKKGLGICYEQQRRRTPKKTKANTSSASDKSLSRRARN CQPKKEKKETVEAEVATDLGLGR | Human hr gene SEQ ID NO: 48 | Θ-defensin[k] SEQ ID NO: 58 | SIVsmm SEQ ID NO: 52 |
| 34 | MAGPHPVIVITGPHEEPLRCICRRGICRLLQRRYGSCAFPGRLYRI CCFLKKGLGICYEQQRRRTPKKTKANTSSASDKSLSRRARNCQPK KEKKETVEAEVATDLGLGR | VIVIT SEQ ID NO: 50 | Θ-defensin SEQ ID NO: 58 | SIVsmm SEQ ID NO: 52 |
| 35 | MDPIDPDLEPWKHPGSQPLRCICRRGICRLLQRRYGSCAFPGRLY RICCFLKKGLGICYEQQRRRTPKKTKANTSSASDKSLSRRARNCQ PKKEKKETVEAEVATDLGLGR | SIVcpz SEQ ID NO: 39 | Θ-defensin SEQ ID NO: 58 | SIVsmm SEQ ID NO: 52 |
| 69 | MEPLTPHPWVYSGGQPKVPLEACYNKCYCKRCCYHCQHCFSKK GLGISYERKGRRRRTPRKTKTPSPSAPDKSISTRTGDSQPTKEQK KTSEATVVTTCGLGQ | Human hr gene SEQ ID NO: 48 | SIVsmm SEQ ID NO: 70 | HIV-2 SEQ ID NO: 71 |

[a]agm = African Green Monkey;
[b]smm = sooty mangabey monkey;
[c]cpz = chimpanzee;
[d]VIVIT = artificial TF sequence;
[e]gor = gorilla;
[f]syk = Sykes monkey;
[g]from Macaca mulatta;
[h]mac = macaque;
[i]mon = Mona monkey;
[j]from Chlorocebus aethiops;
[k]from Pongo abelli.

As used herein the term "conservatively modified variants" refers to variant peptides which have the same or similar biological activity of the original peptides. For example, conservative amino acid changes may be made, which although they alter the primary sequence of the protein or peptide, do not alter its function. A conservative variant has at least one amino acid substituted by another amino acid or an amino acid analog that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 2) or how the original amino acid would tolerate a substitution (Table 3). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 2

Amino Acid Properties

| Property | Amino Acids |
|---|---|
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 3

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |

TABLE 3-continued

Amino Acid Substitutions

| Amino Acid | Favored Substitution | Neutral Substitutions | Disfavored substitution |
|---|---|---|---|
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

TABLE 4

SIV strain abbreviations useful in Tat derivative peptides

| SIV host designation | SIV Host Species | Latin designation |
|---|---|---|
| SIVagmVer | (African Green Monkey) Vervet | *Chlorocebus pygerythrus* |
| SIVagmGri | (African Green Monkey) Grivet | *Chlorocebus aethiops* |
| SIVagmTan | (African Green Monkey) Tantalus | *Chlorocebus tantalus* |
| SIVagmSab | (African Green Monkey) Sabeus | *Chlorocebus sabaeus* |
| SIVrcm | Red-capped Mangabey | *Cercocebus torquatus torquatus* |
| SIVsyk | Sykes Monkey | *Cercopithecus albogularis* |
| SIVagi | Agile Mangabey | *Cercocebus agilis* |
| SIVsun | Sun-tailed Monkey | *Cercopithecus solatus* |
| SIVlho | L'Hoests Monkey | *Cercopithecus lhoesti* |
| SIVstm | Stump-tail Macaque | *Macaca arctoides* |
| SIVmac | Macaque | *Macaca mulatta* |
| SIVsmm | Sooty mangabey monkey | *Cercocebus atys atys* |
| SIVmnd | Mandrill | *Mandrillus sphinx* |
| SIVdrl | Drill Monkey | *Mandrillus leucophaeus* |
| SIVtal | Talapoin Monkey | *Miopithecus talapoin* |
| SIVmus | Mustached Monkey | *Cercopithecus cephus* |
| SIVdeb | De Brazza's Monkey | *Cercopithecus neglectus* |
| SIVden | Dent's Monkey | *Cercopithecus denti* |
| SIVmon | Mona Monkey | *Cercopithecus mona* |
| SIVgor | Gorilla | *Gorilla gorilla* |
| SIVwrc | Western Red Colobus | *Procolobus verus* |
| SIVcpzPtt | Pan Troglodytes Troglodytes | *Pan troglodytes troglodytes* |
| SIVcpzPts | Pan Troglodytes Schweinfurthi | *Pan troglodytes schweinfurthii* |
| SIVmne | Pig-tail Macaque | *Macaca nemestrina* |
| SIVasc | Red-tailed Guenon | *Cercopithecus ascanius schmidti* |
| SIVbab | Yellow Baboon | *Papio* spp. |
| SIVblc | Bioko Black Colobus Monkey | *Cercopithecus satanas satanas* |
| SIVbkm | Black Mangabey | *Lophocebus aterrimus* |
| SIVblu | Blue Monkey | *Cercopithecus mitis* |
| SIVcol | Colobus Monkey | *Colobus guereza* |
| SIVolc | Oilve Colobus Monkey | *procolobus verus* |
| SIVgsn | Greater Spot-nosed Monkey | *Cercopithecus nictitans* |
| SIVkrc | Kibale Red Colobus Moneky | *Procolobus* [*Piliocolobus*] *rufomitratus tephrosceles* |
| SIVpat | Patas Monkey | *Erythrocebus patas* |
| SIVpre | Preussis Monkey | *Cercopithecus preussi* |
| SIVreg | Red-eared Guenon | *Cercopithecus erythrotis erythrotis* |

TABLE 4-continued

SIV strain abbreviations useful in Tat derivative peptides

| SIV host designation | SIV Host Species | Latin designation |
|---|---|---|
| SIVtrc | Tshuapa Red Colobus | *Piliocolobus tholloni* |
| SIVwcm | White-crowned Mangabey | *Cercocebus torquatus lunulatus* |
| SIVwol | Wolf's Monkey | *Cercopithecus wolfi* |

In one embodiment, an immunosuppressive Tat derivative polypeptide is a peptide disclosed in Table 1. An immunosuppressive Tat derivative polypeptide can also comprise conservative variants to a Tat derivative polypeptide. In an embodiment, a conservative variant of an immunosuppressive Tat derivative polypeptide is a conservative variant of an immunosuppressive Tat derivative polypeptide disclosed herein. In aspects of this embodiment, a conservative variant of an immunosuppressive Tat derivative polypeptide can be, for example, an amino acid sequence having at least 50%, 55%, 60%, 65%, 70%, 75%, at least 80%, at least 85%, at least 90%, at least 95%, at least 97%, or at least 98%, or at least 99% amino acid sequence identity to an immunosuppressive Tat derivative polypeptide. In other aspects of this embodiment, a conservative variant of an immunosuppressive Tat derivative polypeptide can be, for example, an amino acid sequence having at most 50%, 55%, 60%, 65%, 70%, 75%, at most 80%, at most 85%, at most 90%, at most 95%, at most 97%, or at most 98%, or at most 99% amino acid sequence identity to an immunosuppressive Tat derivative polypeptide.

In other aspects of this embodiment, a conservative variant of an immunosuppressive Tat derivative polypeptide can be, for example, an immunosuppressive Tat derivative polypeptide having 1, 2, 3, 4, 5, 6, 7, 8, 9, 10, 11, 12, 13, 14, 15, 20, 25, 30 or more conservative substitutions, to the amino acid sequence of an immunosuppressive Tat derivative polypeptide. In other aspects of this embodiment, a conservative variant of an immunosuppressive Tat derivative polypeptide can be, for example, an amino acid sequence having at least 1, at least 2, at least 3, at least 4, at least 5, at least 6, at least 7, at least 8, at least 9, at least 10, at least 11, at least 12, at least 13, at least 14, at least 15, at least 20, or at least 25 conservative substitutions to the amino acid sequence of an immunosuppressive Tat derivative polypeptide. In yet other aspects of this embodiment, a conservative variant of an immunosuppressive Tat derivative polypeptide can be, for example, an amino acid sequence having at most 1, at most 2, at most 3, at most 4, at most 5, at most 6, at most 7, at most 8, at most 9, at most 10, at most 11, at most 12, at most 13, at most 14, at most 15, at most 20, at most 25, or at most 30 conservative substitutions to the amino acid sequence of an immunosuppressive Tat derivative polypeptide.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are immunosuppressive Tat derivative polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides disclosed herein are not limited to products of any of the specific exemplary processes listed herein.

In addition to substantially full length polypeptides, the present disclosure also provides for biologically active fragments of the immunosuppressive Tat derivative polypeptides.

As used herein, amino acid sequences which are substantially the same typically share more than 95% amino acid identity. It is recognized, however, that proteins (and DNA or mRNA encoding such proteins) containing less than the above-described level of identity arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad. Sci. USA 89:10915 (1992). Algorithms conveniently employed for this purpose are widely available (see, for example, Needleman and Wunsch in J. Mol. Bio. 48:443 (1970).

Therefore, disclosed herein are amino acid sequences 85%, 90%, 95%, 98%, 99% or 100% identical to the immunosuppressive Tat derivatives disclosed in Table 1.

An immunosuppressive Tat derivative comprises an altered Tat peptide. In an aspect of this embodiment, an immunosuppressive Tat derivative comprises a Tat peptide in which amino acids 3-19 are altered. In another aspect of this embodiment, an immunosuppressive Tat derivative comprises a Tat peptide in which amino acids 3-19 of SEQ ID NOs:6-11, 13-35, or 69 are altered.

In other aspects of this embodiment, an immunosuppressive Tat derivative has, e.g., at least 70%, at least 75%, at least 80%, at least 85%, at least 90%, at least 93%, at least 95%, at least 97%, or at least 99% amino acid identity with SEQ ID NOs: 6-11, 13-35, or 69. In yet other aspects of this embodiment, an immunosuppressive Tat derivative has, e.g., at most 70%, at most 75%, at most 80%, at most 85%, at most 90%, at most 93%, at most 95%, at most 97%, or at most 99% amino acid identity with SEQ ID NOs: 6-11, 13-35, or 69.

In other aspects of this embodiment, an immunosuppressive Tat derivative has, e.g., at least one, at least two, at least three, at least four, at least five, at least six, at least seven, at least eight, at least nine or at least ten contiguous amino acid substitutions, deletions, and/or additions relative to SEQ ID NOs:6-11, 13-35, or 69. In yet other aspects of this embodiment, an immunosuppressive Tat derivative has, e.g., at most one, at most two, at most three, at most four, at most five, at most six, at most seven, at most eight, at most nine or at most ten contiguous amino acid substitutions, deletions, and/or additions relative to SEQ ID NOs:6-11, 13-35, or 69.

In other aspects of this embodiment, an immunosuppressive Tat derivative has, e.g., at least one, at least two, at least three, at least four, at least five, at least six, at least seven, at least eight, at least nine or at least ten non-contiguous amino acid substitutions, deletions, and/or additions relative to SEQ ID NOs:6-11, 13-35, or 69. In yet other aspects of this embodiment, an immunosuppressive Tat derivative has, e.g., at most one, at most two, at most three, at most four, at most five, at most six, at most seven, at most eight, at most nine or at most ten non-contiguous amino acid substitutions, deletions, and/or additions relative to SEQ ID NOs:6-11, 13-35, or 69.

Furthermore, the peptides disclosed herein can self-associate into multimers, including but not limited to, dimers, trimers, and tetramers, in addition to existing in the monomer form. Multimerization of peptides can occur spontaneously or can be facilitated by subjecting the peptides to conditions conducive to multimerization. These conditions are known to persons of ordinary skill in peptide chemistry. The compositions disclosed herein can include monomers or multimers of the peptides, or a mixture of monomers and multimers.

The following expression systems are suitable for use in expressing the disclosed immunosuppressive Tat derivatives: mammalian cell expression systems such as, but not limited to, insect cell expression systems such as, but not limited to, Bac-to-Bac expression system, baculovirus expression system, and DES expression systems; and *E. coli* expression systems including, but not limited to, pET, pSUMO and GST expression systems. In another embodiment, the Tat derivatives are expressed with a histidine tag useful for isolation of the polypeptide. Histidine tag purification systems are known to persons of ordinary skill in the art. Furthermore, the immunosuppressive Tat derivatives can be synthesized by conventional chemical synthesis techniques known to persons of ordinary skill in the art.

As used herein, the terms "treating" or "treatment" when used in reference to a disorder include preventing at least one symptom of the condition, i.e., causing a clinical symptom to not significantly develop in a subject that may be exposed to, or predisposed to, the disease but does not yet experience or display symptoms of the disease, inhibiting the disease, i.e., arresting or reducing the development of the disease or its symptoms, or relieving the disease, i.e., causing regression of the disease or its clinical symptoms. Treatment, prevention, and ameliorating a condition, as used herein, can include, for example decreasing or eradicating a deleterious or harmful condition associated with inflammation, an autoimmune disorder, or a neurodegenerative disease.

"Therapeutically effective amount" is intended to qualify the amount required to achieve a therapeutic effect.

The present disclosure is also directed to pharmaceutical compositions comprising the above-described immunosuppressive Tat derivative polypeptides. Dosages and desired drug concentrations of the disclosed pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. In one embodiment, the disease is present. In another embodiment, the life of a cell or an individual is prolonged due to the methods described herein.

Accordingly, the compositions designed for oral, nasal, lingual, sublingual, buccal, intrabuccal, intravenous, subcutaneous, intramuscular and pulmonary administration can be made without undue experimentation by means well known in the art, for example with an inert diluent or with an pharmaceutically acceptable carrier. For the purpose of therapeutic administration, the pharmaceutical compositions may be incorporated with excipients and used in the form of tablets, troches, capsules, elixirs, suspensions, solutions, syrups, and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Compositions comprising such carriers are formulated by well known conventional methods.

The immunosuppressive Tat derivative polypeptide compositions can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The immunosuppressive Tat derivative polypeptide compositions of the present disclosure may be administered in a therapeutically effective amount, according to an appropriate dosing regimen. As understood by a skilled artisan, the exact amount required may vary from subject to subject, depending on the subject's species, age and general condition, the severity of the disease, the particular agent(s) and the mode of administration. In some embodiments, about 0.0001 mg/kg to about 50 mg/kg, of the composition based on the subject's body weight is administered, one or more times a day, to obtain the desired therapeutic effect. In other embodiments, about 0.001 mg/kg to about 50 mg/kg, about 0.01 mg/kg to about 50 mg/kg, about 0.1 mg/kg to about 50 mg/kg, about 1 mg/kg to about 50 mg/kg, about 10 mg/kg to about 50 mg/kg, about 0.0001 mg/kg to about 25 mg/kg, about 0.0001 mg/kg to about 10 mg/kg, about 0.0001 mg/kg to about 5 mg/kg, about 0.0001 mg/kg to about 1 mg/kg, about 1 mg/kg to about 45 mg/kg, about 1 mg/kg to about 40 mg/kg, about 1 mg/kg to about 35 mg/kg, about 1 mg/kg to about 30 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately. Suitable therapeutic agents include, but are not limited to, immunosuppressive agents, anti-inflammatory agents, chemotherapeutic agents, immunomodulatory agents, biologic agents, and small molecules.

In another embodiment, repetitive, or frequent, dosing of the disclosed immunosuppressive Tat derivatives is contemplated. Frequent dosing is one procedure used for example in allergy therapy that can support immunological tolerance to an agent.

The number of repeated doses of the immunosuppressive Tat derivatives can be established by the medical professional based on the response of the patient to the doses. In one embodiment, the immunosuppressive Tat derivative is administered once every three days for 3 doses in a ten day period. This administration scheme is then repeated for a plurality of cycles. The present disclosure envisions a variety of different administration schemes wherein the immunosuppressive Tat derivative is administered multiple times within a selected time frame and then the administration scheme is repeated for a plurality of cycles. In another embodiment, administration of the immunosuppressive Tat derivative can be alternated with administration of one or more other therapeutic agents.

Aspects of the present specification provide, in part, a composition comprising an immunosuppressive Tat derivative polypeptide. An immunosuppressive Tat derivative polypeptide includes the compounds disclosed herein. The compositions disclosed herein may, or may not, comprise any number and combination of compounds disclosed herein. For instance, a composition can comprise two or more compounds disclosed herein or three or more compounds disclosed herein.

A compound disclosed herein, or a composition comprising such a compound, is generally administered to an individual as a pharmaceutical composition. Pharmaceutical compositions may be prepared by combining a therapeutically effective amount of at least one compound as disclosed herein as an active ingredient, with conventional acceptable pharmaceutical excipients, and by preparation of unit dosage forms suitable for therapeutic use. As used herein, the term "pharmaceutical composition" and refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, powder, syrup, elixir, or any other dosage form suitable for administration.

Liquid dosage forms suitable for parenteral injection may comprise physiologically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. In liquid formulations, a therapeutically effective amount of a compound disclosed herein may be between about 0.0001% (w/v) to about 50% (w/v), about 0.001% (w/v) to about 10.0% (w/v), or about 0.01% (w/v) to about 1.0% (w/v).

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor.

A compound disclosed herein, or a composition comprising such a compound, may also be incorporated into a drug delivery platform in order to achieve a controlled compound release profile over time. Such a drug delivery platform comprises a compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., U.S. Pat. No. 4,756,911; U.S. Pat. No. 5,378,475; U.S. Pat. No. 7,048,946; U.S. Patent Publication 2005/0181017; U.S. Patent Publication 2005/0244464; U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present disclosure provide, in part, an autoimmune disorder. An autoimmune disorder arises from an overactive immune response of the body against substances and tissues normally present in the body resulting in a break in tolerance toward self-antigens. In other words, the body actually attacks its own cells because the immune system mistakes some part of the body as a pathogen and attacks it. Characterized by the development of pathogenic T cell populations infiltrating the target organ or tissue, autoimmune disorders may be restricted to certain organs or involve a particular tissue in different places.

Aspects of the present disclosure provide, in part, an inflammation. Inflammation refers to the actual tissue response (edema, erythema, etc) to a noxious stimulus. Neurogenic inflammation refers to the fact that this tissue response is initiated and/or maintained through the release of inflammatory mediators from peripheral sensory nerve terminals (i.e., an efferent function, in contrast to the normal afferent signaling to the spinal cord in these nerves). Neurogenic inflammation encompasses a series of vascular and non-vascular inflammatory responses mediated by a complex biological process that ultimately results in the local release of inflammatory mediators and sensitizing compounds from sensory neurons. Upon insult by a noxious stimulus, such as, e.g., a pathogen, damage to cells, or an irritant, inflammation mediating and sensitizing molecules, such as, e.g., histamine, prostaglandins, leukotrienes, serotonin, neutral proteases, cytokines, bradykinin and nitric oxide, are released from inflammation mediating cells, such as, e.g., mast cells, immune cells, vascular endothelial cells, and vascular smooth muscle cells. See Richardson and Vasko, J. Pharmacol. Exp. Ther. 302:839-845, (2002), which is hereby incorporated by reference in its entirety. These inflammation mediating and sensitizing molecules act on sensory neurons to stimulate the release of inflammation inducing molecules such as, e.g., neuropeptides like substance P(SP) and calcitonin gene-related peptide (CGRP), prostaglandins, and amino acids like glutamate, from the peripheral nerve endings. Upon release, these inflammation inducing molecules are responsible for eliciting an inflammatory response, typically characterized by edema (swelling secondary to plasma extravasation), hypersensitivity (secondary to alterations in the excitability of certain sensory neurons), and an erythema (redness and warmth secondary to vasodilation) which extends beyond the site of stimulation (the flare response). Id. Because the underlying inflammatory symptoms are triggered by the activation of primary sensory neurons and the subsequent release of inflammation inducing molecules, the response is termed neurogenic inflammation.

Inflammation includes both acute inflammation and chronic inflammation. As used herein, the term "acute inflammation" means an inflammatory response having pathophysiology effects where at least one of the underlying symptoms being treated is due to a noxious stimulus etiology, such as, e.g., an antimicrobial response. As used herein, the term "chronic inflammation" means an inflammatory response having pathophysiology effects where at least one of the underlying symptoms being treated is due to a nociceptive sensory nerve-based etiology, such as, e.g., the release of an inflammation inducing molecule. Chronic inflammation includes both primary neurogenic inflammation and secondary neurogenic inflammation. As used herein, the term "primary" neurogenic inflammation refers to tissue inflammation (inflammatory symptoms) that is initiated by, or results from, the release of substances from primary sensory nerve terminals (such as C and A-delta fibers). As used herein, the term "secondary" neurogenic inflammation" refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. These nerve-derived inflammatory mediators can, in turn, stimulate the sensory nerves as well as acting on non-neuronal targets (e.g., mast cells). The net effect of both forms (primary and secondary) of neurogenic inflammation is to have an inflammatory state that is maintained by the sensitization of the peripheral sensory nerve fibers. The physiological consequence of the resulting neurogenic inflammation depends on the tissue in question, producing, such as, e.g., cutaneous pain (allodynia, hyperalgesia), joint arthritis, visceral pain and dysfunction, pulmonary dysfunction (asthma, COPD), and bladder dysfunction (pain, overactive bladder).

Inflammation and/or autoimmune disorder symptoms include, without limitation, edema, hyperemia, erythema, bruising, tenderness, stiffness, swollenness, fever, a chill, congestion of the respiratory tract including nose, and bronchi, congestion of a sinus, a breathing problem, fluid retention, a blood clot, loss of appetite, increased heart rate, formation of granulomas, fibrinous, pus, or non-viscous serous fluid, formation of an ulcer, or pain. The actual symptoms associated with an inflammation and an autoimmune disorder disclosed herein are well known and can be determined by a person of ordinary skill in the art by taking into account factors, including, without limitation, the location of the inflammation or autoimmune disorder, the cause of the inflammation or autoimmune disorder, the severity of the inflammation or autoimmune disorder, the tissue or organ affected by inflammation or the autoimmune disorder, and the disorder associated with the inflammation.

Normally, inflammation serves as a protective mechanism by an organism to remove noxious stimuli as well as initiate the healing process for injured tissue. This acute neurogenic inflammation forms the first line of defense by maintaining tissue integrity and contributing to tissue repair. In fact, in the absence of acute neurogenic inflammation, wounds and infections would never heal and progressive destruction of the tissue would compromise the survival of the organism. However, severe or prolonged noxious stimulation results in a chronic inflammatory response provoking injury rather than mediating repair. This inflammation has been implicated in the pathophysiology of a wide range of unrelated disorders which underlie a wide variety of human diseases.

Chronic inflammation and its associated symptoms can be associated with a large, unrelated group of disorders which underlie a variety of human diseases. Non-limiting examples of disorders exhibiting inflammation as a symptom include, without limitation, acne, acid reflux/heartburn, Alzheimer's disease, appendicitis, arteritis, arthritis, asthma, allergy, allergic rhinitis, atherosclerosis, an autoimmune disorder, balanitis, blepharitis, bronchiolitis, bronchitis, bullous pemphigoid, ursitis, a cancer, carditis, celiac disease, cellulitis, cervicitis, cholangitis, cholecystitis, chorioamnionitis, chronic obstructive pulmonary disease (COPD), cirrhosis, colitis, conjunctivitis, cystitis, common cold, dacryoadenitis, dementia, dermatitis, dermatomyositis, eczema, emphysema, encephalitis, endocarditis, endometritis, enteritis, enterocolitis, epicondylitis, epididymitis, fasciitis, fibrositis, gastritis, gastroenteritis, gingivitis, glomerulonephritis, glossitis, a heart disease, hepatitis, hidradenitis suppurativa, high blood pressure, ileitis, an inflammatory dermatologic disease, an inflammatory neuropathy, insulin resistance, interstitial cystitis, iritis, ischemic heart disease, keratitis, keratoconjunctivitis, laryngitis, mastitis, mastoiditis, a meningitis, metabolic syndrome (syndrome X), migraine, myelitis, myocarditis, myositis, nephritis, obesity, omphalitis, oophoritis, orchitis, osteochondritis, osteopenia, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, proctitis, prostatitis, a psoriasis, pulpitis, pyelonephritis, pylephlebitis, rheumatic fever, rhinitis, salpingitis, sialadenitis, sinusitis, a spastic colon, stomatitis, synovitis, tendonitis, tendinosis, tenosynovitis, thrombophlebitis, tonsillitis, trigonitis, a tumor, urethritis, uveitis, vaginitis, vasculitis, and vulvitis.

One type of disorder exhibiting a symptom of inflammation is an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple's disease and Behcet's disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an autoimmune disease or a non-autoimmune disease.

Aspects of the present disclosure provide, in part, a autoimmune disorder. Autoimmune disorders also exhibit symptoms of inflammation. Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjögren's syndrome, scleroderma, rheumatoid arthritis and polymyositis. Local autoimmune diseases may be endocrinologic (diabetes mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy, allergic rhinitis, Alzheimer's disease, antiphospholipid antibody syndrome (APS), an arthritis, asthma, autoimmune hemolytic anemia, autoimmune hepatitis, autoimmune inner ear disease, bullous pemphigoid, cardiovascular disease, celiac disease, Chagas disease, chronic obstructive pulmonary disease (COPD), diabetes mellitus type 1 (IDDM), eczema, endometriosis, fibromyalgia, Goodpasture's syndrome, Graves' disease, Guillain-Barré syndrome (GBS), Hashimoto's thyroiditis, hidradenitis suppurativa, idiopathic thrombocytopenic purpura, an inflammatory bowel disease, an inflammatory dermatologic disease, interstitial cystitis, a lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, a psoriasis, primary biliary cirrhosis, recurrent disseminated encephalomyelitis (multiphasic disseminated encephalomyelitis), rheumatic fever, schizophrenia, scleroderma, Sjögren's syndrome, tenosynovitis, vasculitis, and vitiligo.

Another type of disorder exhibiting a symptom of inflammation is an inflammatory myopathy. Inflammatory myopathies are caused by problems with the immune system attacking components of the muscle, leading to signs of inflammation in the muscle. Inflammatory myopathies include, without limitation, dermatomyositis, inclusion body myositis, and polymyositis.

Another type of disorder exhibiting a symptom of inflammation is a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behçet's disease, or other connective tissue disorders, vasculitis secondary to viral infection.

Another type of disorder exhibiting a symptom of inflammation is a skin disorder. Skin disorders include, without limitation, a dermatitis, including chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, psoriasis including plaqure psoriasis, nail psoriasis, guttate psoriasis, scalp psoriasis, inverse psoriasis, pustular psoriasis, and erythrodermis psoriasis, rosacea and scleroderma including morphea.

Another type of disorder exhibiting a symptom of inflammation is a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

Aspects of the present disclosure provide, in part, a neurodegenerative disease. Neurodegenerative arises from the progressive loss of structure or function of neurons, including death of neurons. Non-limiting examples of a neurodegenerative diseases include, but are not limited to, Alexander disease, Alper's disease, Alzheimer's disease, amyloidoses, amyotrophic lateral sclerosis, anxiety, ataxia telangiectasia, attention deficit disorders, Canavan disease, central nervous system injuries, Charcot Marie Tooth disease, Cockayne syndrome, corticobasal degeneration, Creutzfeldt-Jakob disease, depression, encephalitis (e.g., bacterial, parasitic, fungal, or viral), Friedreich's ataxia frontotemporal dementia, hereditary spastic paraparesis, Guillain-Barre syndrome (and its variants acute motor axonal neuropathy, acute inflammatory demyelinating polyneuropathy, and Fisher syndrome), HIV/AIDS dementia complex, Huntington's disease, ischemic damage to the nervous system, Kennedy's disease, Krabbe disease, Lewy body dementia, Machado-Joseph disease, meningitis (e.g., bacterial, parasitic, fungal, or viral), multiple sclerosis, multiple system atrophy, neural trauma, e.g., percussive brain damage, spinal cord injury and traumatic damage to the nervous system, a neuropathy such as e.g., chemotherapy-induced neuropathy, diabetes-associated neuropathy, and peripheral neuropathy, Parkinson's disease, Pelizaeus-Merzbacher disease, Pick's disease, primary lateral sclerosis, prion disorders, progressive supranuclear palsy, Refsum's disease, Sandhoff disease, schizophrenia, Schilder's disease, spinocerebellar atrophies, Steele-Richardson-Olszewski disease, stroke, tabes dorsalis, and vascular dementia. The neurodegeneration may be associated with an auto-immune disease or a non-autoimmune disease, and the neurodegeneration may be a systemic disorder or an organ-specific disorder. Non-limiting examples of a symptom reduced by a method of treating a neurodegenerative disease disclosed herein include anxiety, aphasia, cognition, confusion, depression, pain, paralysis, spasticity, tics, and tremors.

Aspects of the present disclosure provide, in part, reducing a symptom associated with an autoimmune disorder or a neurodegenerative disease. In an aspect of this embodiment, the symptom reduced is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue or, the destruction of an organ or tissue.

In an embodiment, the immunosuppressive Tat derivative polypeptide has activity that results in increased Fas ligand (FasL) expression in antigen presenting cell regulatory macrophages (ARegs) exposed to the immunosuppressive Tat derivative polypeptide. In aspects of this embodiment, an immunosuppressive Tat derivative polypeptide increases FasL expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same immunosuppressive Tat derivative polypeptide. In other aspects of this embodiment, an immunosuppressive Tat derivative polypeptide increases FasL expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to cells not exposed to the same immunosupppressive Tat derivative. In certain embodiments, the ARegs are CD14+ macrophages.

The disclosed autoimmune, neurodegenerative, and inflammation-associated diseases are immune-mediated disorders characterized by an increase in T cell-mediated inflammation that is desired to be reduced. A therapeutic agent which increases, or induces expression of, FasL on ARegs, or dendritic cells, decreases T cell-mediated inflammation and thereby treats the autoimmune, neurodegenerative, or inflammation associated disease. Therefore, in one embodiment, the present disclosure provides a method for decreasing T cell-mediated inflammation in a subject with an autoimmune, neurodegenerative, or inflammation-associated disease by administration of one or more of the disclosed immunosuppressive Tat derivative polypeptides, thereby treating the autoimmune, neurodegenerative, or inflammation-associated disease. In another embodiment, the present disclosure provides a method of inducing the expression of FasL on ARegs in a subject with an autoimmune, neurodegenerative, or inflammation-associated disease by administration of one or more of the disclosed immunosuppressive Tat derivative polypeptides, thereby treating the autoimmune, neurodegenerative, or inflammation-associated disease.

Aspects of the present disclosure additionally provide, in part, reducing a symptom associated with inflammation. In an aspect of this embodiment, the symptom reduced is edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

Aspects of the present disclosure provide, in part, a mammal. A mammal includes a human, and a human can be a patient. Other aspects of the present disclosure provide, in part, an individual. An individual includes a mammal and a human, and a human can be a patient. In other embodiments, mammals include domesticated animals such as dogs, cats, horses, cattle, sheep, goats, and primates.

Aspects of the present disclosure provide, in part, administering a compound or a composition disclosed herein. As used herein, the term "administering" means any delivery mechanism that provides a compound or a composition disclosed herein to an individual that potentially results in a clinically, therapeutically, or experimentally beneficial result.

Administration of a compound or a composition disclosed herein include a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; perk and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A compound or a composition disclosed herein can be administered to a mammal using a variety of routes. Routes of administration suitable for treating inflammation, an autoimmune disorder, or a neurodegenerative disease as disclosed herein include both local and systemic administration. Local administration results in significantly more delivery of a composition to a specific location as compared to the entire body of the mammal, whereas, systemic administration results in delivery of a composition to essentially the entire body of the individual. Suitable routes of administration also include both central and peripheral administration. Central administration results in delivery of a compound or a composition to essentially the central nervous system of the individual and includes, e.g., intrathecal administration, epidural administration as well as a cranial injection or implant. Peripheral administration results in delivery of a compound or a composition to essentially any area of an individual outside of the central nervous system and encompasses any route of administration other than direct administration to the spine or brain. The actual route of administration of a compound or a composition disclosed herein used can be determined by a person of ordinary skill in the art by taking into account factors, including, without limitation, the type, location, cause and severity of inflammation or an autoimmune or neurodegenerative disorder, the duration of treatment desired, the degree of relief desired, the duration of relief desired, the particular compound or composition used, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of a compound or a composition disclosed herein can thus readily be determined by the person of ordinary skill in the art considering all criteria and utilizing his best judgment on the individual's behalf.

In an embodiment, a compound or a composition disclosed herein is administered systemically to a mammal. In another embodiment, a compound or a composition disclosed herein is administered locally to a mammal. In an aspect of this embodiment, a compound or a composition disclosed herein is administered to a site of inflammation, neurodegeneration, or autoimmune disorder of a mammal. In another aspect of this embodiment, a compound or a composition disclosed herein is administered to the area surrounding an inflammation, neurodegenerative disease, or autoimmune disorder of a mammal.

Aspects of the present specification provide, in part, administering a therapeutically effective amount of a compound or a composition disclosed herein. As used herein, the term "therapeutically effective amount" is synonymous with "therapeutically effective dose" and when used in reference to treating inflammation, neurodegeneration, or an autoimmune disorder means the minimum dose of a compound or composition disclosed herein necessary to achieve the desired therapeutic effect and includes a dose sufficient to reduce a symptom associated with inflammation, neurodegeneration, or an autoimmune disorder. In aspects of this embodiment, a therapeutically effective amount of a compound or a composition disclosed herein reduces a symptom associated with inflammation, neurodegeneration, or an autoimmune disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a compound or a composition disclosed herein reduces a symptom associated with inflammation, neurodegeneration, or an autoimmune disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a compound or a composition disclosed herein reduces a symptom associated with inflammation, neurodegeneration, or an autoimmune disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a compound or a composition disclosed herein is the dosage sufficient to reduces a symptom associated with inflammation, neurodegeneration, or an autoimmune disorder for, e.g., at least one week, at least one month, at least two months, at least three months, at least four months, at least five months, at least six months, at least seven months, at least eight months, at least nine months, at least ten months, at least eleven months, or at least twelve months.

The amount of active component in a compound or a composition disclosed herein for treating inflammation, neurodegeneration, or an autoimmune disorder can be varied so that a suitable dosage is obtained. The actual therapeutically effective amount of a compound or a composition disclosed herein to be administered to a mammal can be determined by a person of ordinary skill in the art by taking into account factors, including, without limitation, the type, location, cause or severity of inflammation, neurodegeneration, or an autoimmune disorder, the duration of treatment desired, the degree of relief desired, the duration of relief desired, the particular compound or composition used, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of a compound or a composition disclosed herein can thus readily be determined by the person of ordinary skill in the art considering all criteria and utilizing his best judgment on the individual's behalf.

Additionally, where repeated administration of a compound or a composition disclosed herein is used, the actual effect amount of a compound or a composition disclosed herein will further depend upon factors, including, without limitation, the frequency of administration, the half-life of the compound or composition disclosed herein, or any combination thereof. It is known by a person of ordinary skill in the art that an effective amount of a compound or a composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

Dosing can be single dosage or cumulative (serial dosing), and can be readily determined by one skilled in the art. For instance, treatment of inflammation, neurodegeneration, or an autoimmune disorder may comprise a one-time administration of an effective dose of a compound or a composition disclosed herein. As a non-limiting example, an effective dose of a compound or a composition disclosed herein can be administered once to a mammal, e.g., as a single injection or deposition at or near the site exhibiting a symptom of inflammation, neurodegeneration, or an autoimmune disorder or a single oral administration of the compound or a composition. Alternatively, treatment of inflammation, neurodegeneration, or an autoimmune disorder may comprise multiple administrations of an effective dose of a compound or a composition disclosed herein carried out over a range of time periods, such as, e.g., daily, once every few days, weekly, monthly or yearly. As a non-limiting example, a compound or a composition disclosed herein can be administered once or twice weekly to a mammal. The timing of administration can vary from mammal to mammal, depending upon such factors as the severity of a mammal's symptoms. For example, an effective dose of a compound or a composition disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a compound or a composition disclosed herein that is administered can be adjusted accordingly.

A compound or a composition disclosed herein as disclosed herein can also be administered to a mammal in combination with other therapeutic compounds to increase the overall therapeutic effect of the treatment. The use of multiple compounds to treat autoimmune, neurodegenerative, and inflammation-associated diseases is within the scope of the present disclosure. Additionally, the present disclosure includes the use of the disclosed peptides to treat autoimmune, neurodegenerative, and inflammation-associated diseases and the use of the disclosed peptides in the manufacture of a medicament to treat autoimmune, neurodegenerative, and inflammation-associated diseases.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating an autoimmune disorder, inflammation, or neurodegenerative diseases using the Tat derivatives disclosed herein.

Example 1

Effects of Tat on the Dendritic Cell Lineage

Tat induces monocytes committed to the dendritic cell (DC) lineage to enlarge into activated, CD86+ DC APCs (FIG. 1). Human monocytes enriched from PBMCs by Percoll density gradient separation and adherance to anti-CD14 coated magnetic beads (Dynabeads M-450, Dynal Biotech) were committed to differentiate into DCs through five days of culture in GM-CSF (100 ng/mL) and IL-4 (100 ng/mL). Committed DCs were cultured overnight either in medium alone (Control), LPS (100 ng/mL), or Tat (50 nM), after which they were stained with an anti-CD86 antibody (BD Pharmingen) and analyzed by FACScan for CD86 induction (left panel) or generalized activation (right panel, enlargement into box R2, shown for Tat-stimulated cells). The MFIs for CD86 expression are 9 (Control), 30 (LPS), and 187 (Tat), CD86 being a specific determinant of DC activation.

Derivitzed Tat reduces AReg differentiation and potently enhances antigen-specific activation of CTLs (FIG. 2). Tat is chemically derivatized by oxidation (Tat* or ox-Tat) so that it does not induce ARegs from monocyte APC precursors (FIG. 3). Ten micrograms of Tat/p24 Tat*-Ag conjugate (Ag-Tat*) was administered into the flanks of Balb/C mice in adjuvant on day 0 and day 7. Experimental groups were comparatively immunized in adjuvant with 5 µg of p24 in one flank and 5 µg derivatized Tat in the other flank (Ag & Tat*), or 10 µg of p24 in adjuvant (Ag). Control mice were given two injections of adjuvant. Four mice were treated in each group. At day 14, draining lymph node cells from each animal were harvested and re-stimulated overnight in cultures of irradiated Ap24 (H-2d cells stably transfected to express antigen p24) cells or control non-transfected cells. CTL activity was quantitated as the number of γ-interferon secreting spot forming colonies (SFC)/$10^6$ plated cells using ELISPOT assays. The background with non-transfected re-stimulators, which was in all cases <10 SFC/$10^6$, is subtracted from each point. The results are indicative of three similar experiments.

Example 2

Tat Activation of Macrophages and Suppression of the Immune Response

Recombinant Tat protein is prepared as previously described (Li, C. J. et al. (1995), Science 268:429-31) under mildly denaturing conditions and was renatured in the presence of 0.1 mM DTT.

Tat activation of monocytes is dose-dependent and saturable (FIG. 3). Human monocytes were cultured in increasing concentrations of recombinant Tat for six days at which time they were assayed for Fas ligand (FasL) induction as a measure of activation by using flow cytometry (FACScan, Becton Dickinson) to quantitate the intensity of staining (mean fluorescence index (MFI)) with an anti-Fas ligand monoclonal antibody (Nok 1, BD Pharmingen). Higher concentrations of Tat did not increase MFI (not shown), and T cells could not be activated with 50 nM Tat (not shown), the plateau stimulatory concentration for APCs.

Figure 4A:
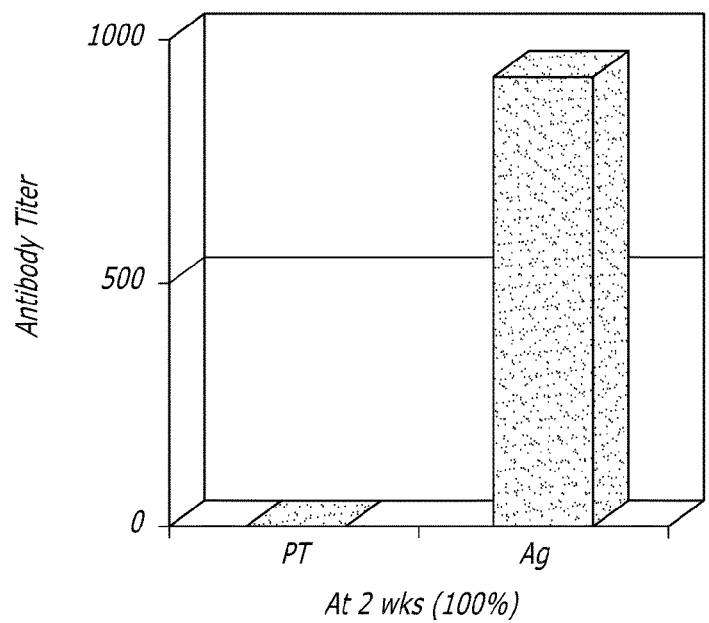
FIG. 4A-B depict antibody titer to an immunogenic antigen in the presence of the immunosuppressive Tat (PT) or with non-immunosuppressive ox-Tat* (Ag) after two weeks (FIG. 4A) or six weeks (FIG. 4B).
Figure 4B:
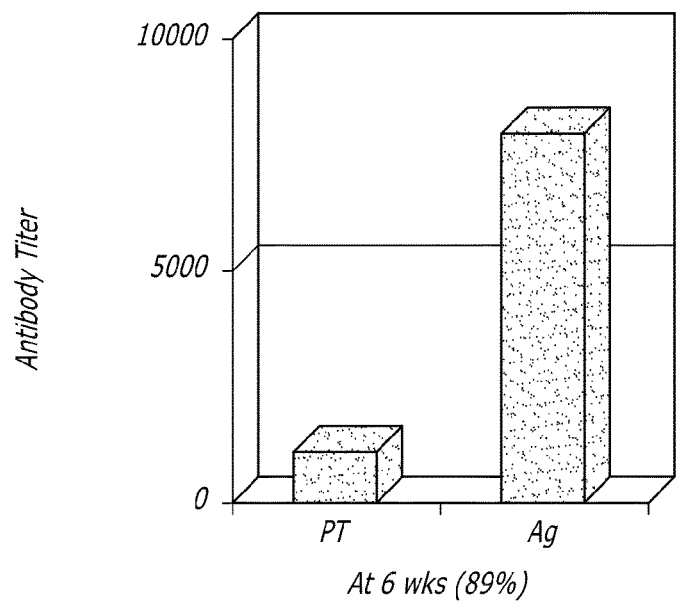

Tat suppresses the antigen-specific humoral immune response to HIV-1 p24 (FIG. 4). At week 0, mice (4 in each group) were immunized with 5 µg recombinant p24 protein (Chiron, Emeryville, Calif.) and either 5 µg recombinant Tat protein (PT) or 5 µg recombinant ox-Tat* protein (Ag) mixed in 100 µL complete Freund's adjuvant and administered subcutaneously in the flank. Following immunization, sera were collected every other week for 10 weeks and assayed for a specific antibody response to p24 by commercially available ELISA (Abbott Laboratories, Abbott Park, Ill.). The p24 antibody titer at 2 weeks (FIG. 4A) was completely suppressed by the Tat protein (PT) compared with the ox-Tat* control (Ag). This response was maintained for at least 6 weeks. The antibody titers at 6 weeks are approximately ten times greater than at week 2 due to maturation of the immune response.

Figure 5:
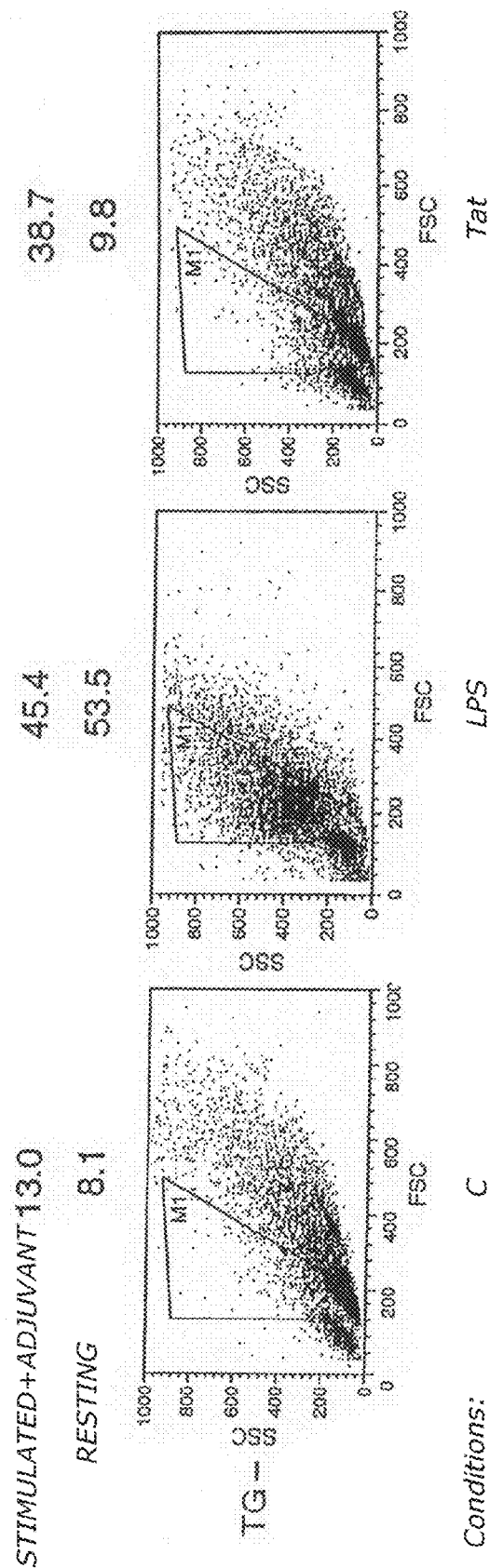
FIG. 5 depicts FACS analysis of mouse peritoneal macrophages that were isolated either after in vivo thioglycolate stimulation (stimulated+adjuvant) or without in vivo stimulation (resting). Mouse peritoneal macrophages were cultured for five days either in the absence of additional stimulation (C), with LPS or with Tat. Activation was determined as percent enlarged cells (M1 fraction).

Tat enhances the viability of cultured murine macrophages as long as the macrophages were first activated in vivo compared with no prior activation and stimulated with relatively high concentrations of Tat (FIG. 5). APCs were isolated by peritoneal lavage from mice intraperitoneally injected four days earlier with either 2.9% thioglycolate (as adjuvant) or 0.85% saline solution (resting). Harvested washout cells were cultured at $10^6$ cells/mL for five days in medium alone (Control, C), lipopolysaccharide (LPS, 100 ng/mL), or Tat produced as recombinant protein in *E. coli* (Tat, 500 ng/mL). Activation was determined as % enlarged cells (M1 fraction).

Figure 6:
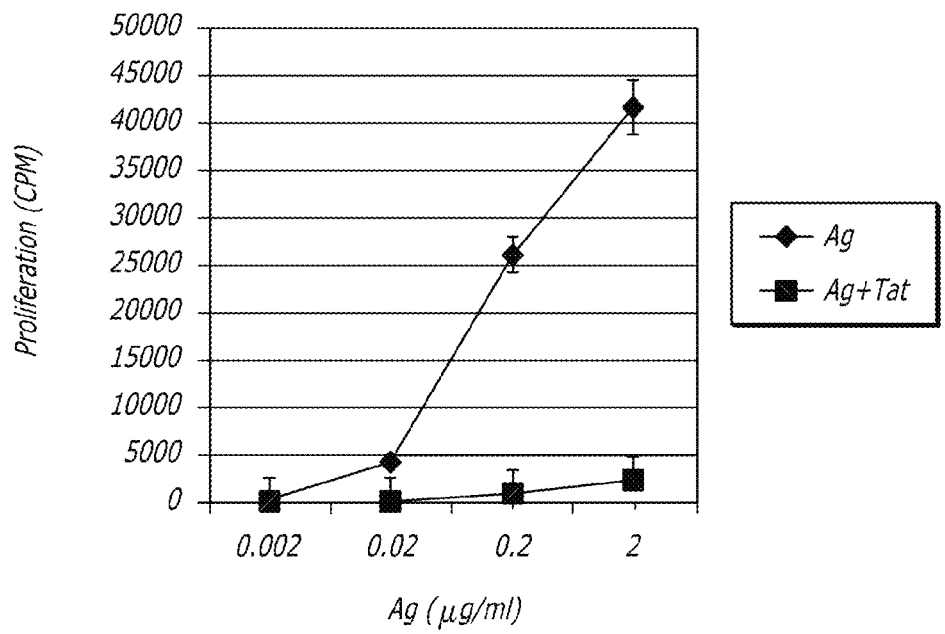
FIG. 6 depicts stable suppression of antigen-stimulated T lymphocytes by Tat-Ag complexes two weeks after immunization with immunosuppressive Tat.

The immunosuppressive Tat produces a stable suppression of mouse lymphocyte proliferation (FIG. 6). Mice were immunized in quadruplicate with a Freund's adjuvant emulsion containing either 5 µg Tat/p24 (recombinant HIV-1 gag protein p24) tolerogen (GRP 2) or with 5 µg avidin-p24 (GRP 1) as control. At two weeks residual draining lymph node cells were harvested, pooled within each group, and cultured at $10^5$ cells/microtiter well for four days in the presence of graded concentrations of recombinant p24 protein (p24, µg/mL). Proliferation was assayed as a determinant of recall T cell response by quantitating overnight $^3$H thymidine uptake (CPM) in a liquid scintillation counter. This response is maintained for up to six weeks.

Figure 7:
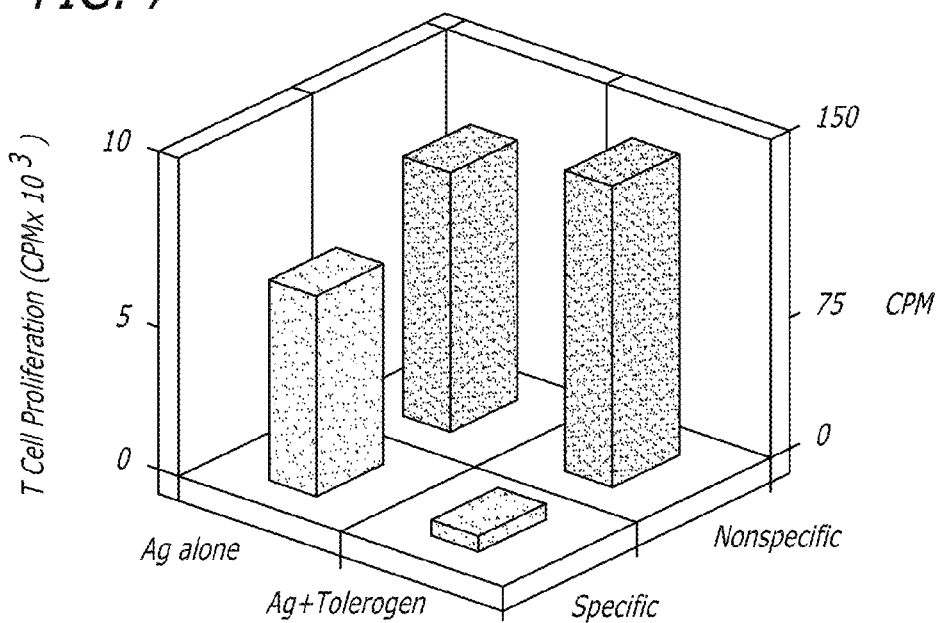
FIG. 7 depicts the antigen-specificity of Tat suppression. Mice were immunized at day 0 and boosted at day 7 with an adjuvant emulsion containing either Tat (Ag+Tat), or with Ag alone as control. At day 14, draining lymph node cells were harvested and stimulated with either specific or non-specific antigen and proliferation measured by $^3$H thymidine uptake (CPM) after four days of culture.

In addition, the immunosuppressive Tat generates an antigen-specific immune suppression (FIG. 7). Mice in quadruplicate were immunized at day 0 and boosted at day 7 with an adjuvant emulsion containing either 5 µg Tat/p24 tolerogen (Ag+Tol) or with 5 µg avidin-p24 (Ag Alone) as control. At day 14, draining lymph node cells were harvested and stimulated at $10^5$ cells/microtiter culture well either with added antigen (Specific, recombinant p24, 1 µg/mL) or with added anti-T cell receptor monoclonal antibody (NonSpecific, 2C11, 10 µg/mL). Tritiated thymidine uptake (CPM) was determined by liquid scintillation at day 4 of culture. The specific Ag+Tol response is suppressed 98% relative to Ag alone, and is not distinguishable from cells cultured in the absence of stimulants.

Example 3

Tat Suppression is Mediated by ARegs

Figure 8:
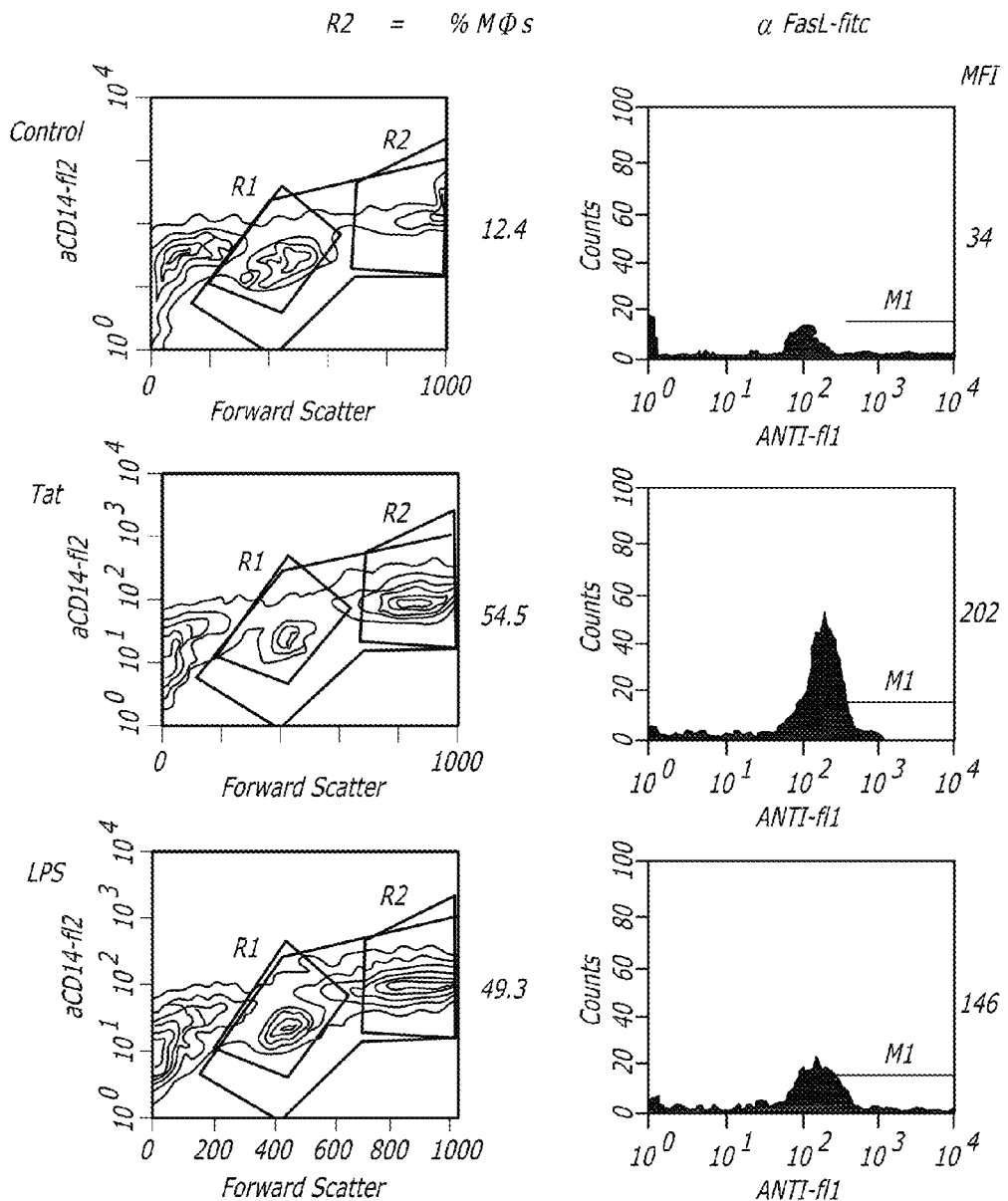
FIG. 8 depicts FACS analysis of human peripheral blood monocytes cultured for four days in control medium (control), or medium containing Tat or LPS. Harvested cells were doubly stained with a fluoresceinated anti-FasL Mab (αFasL-FITC) and with an anti-CD14 rhodamine labeled Mab. Cells were analyzed by FACScan for activation (forward scatter), CD14 expression (% macrophages, R2), and for induction of FasL (MFI). The T cell population is labeled R1.

Tat mediated antigen-specific suppression is mediated through trans- (intracellular) activation of a CD14+ FasL+ macrophage (FIG. 8). In mice, Tat tolerizes at the T cell level and is maintained for at least six weeks after the initial treatment under the conditions demonstrated in FIG. 6. A human peripheral blood mononuclear cell (PBMC) population enriched for monocytes by Percoll centrifugation was cultured for four days either in medium containing 5% fetal calf serum (FCS, Control), Tat (50 nM), or LPS (100 ng/mL). Harvested cells were doubly stained with a fluoresceinated (anti-fl1) anti-FasL monoclonal antibody (Mab), (αFasL-FITC, Nok 1, BD Pharmingen) and with an anti-CD14 rhodamine labeled Mab (αCD14fl2, BD Biosciences, CD14 being a determinant specific to macrophages (Mφ). Cells were analyzed by FACScan (Becton Dickinson) for activation (Forward Scatter), CD14 expression (R2, percent Mφs), and for induction of FasL (MFI). The T cell population (R1) was CD14− and did not express FasL. Similar results were obtained from cells harvested after 2, 3, 5, or 6 days of culture as for PBMCs harvested at day four.

Figure 9A:
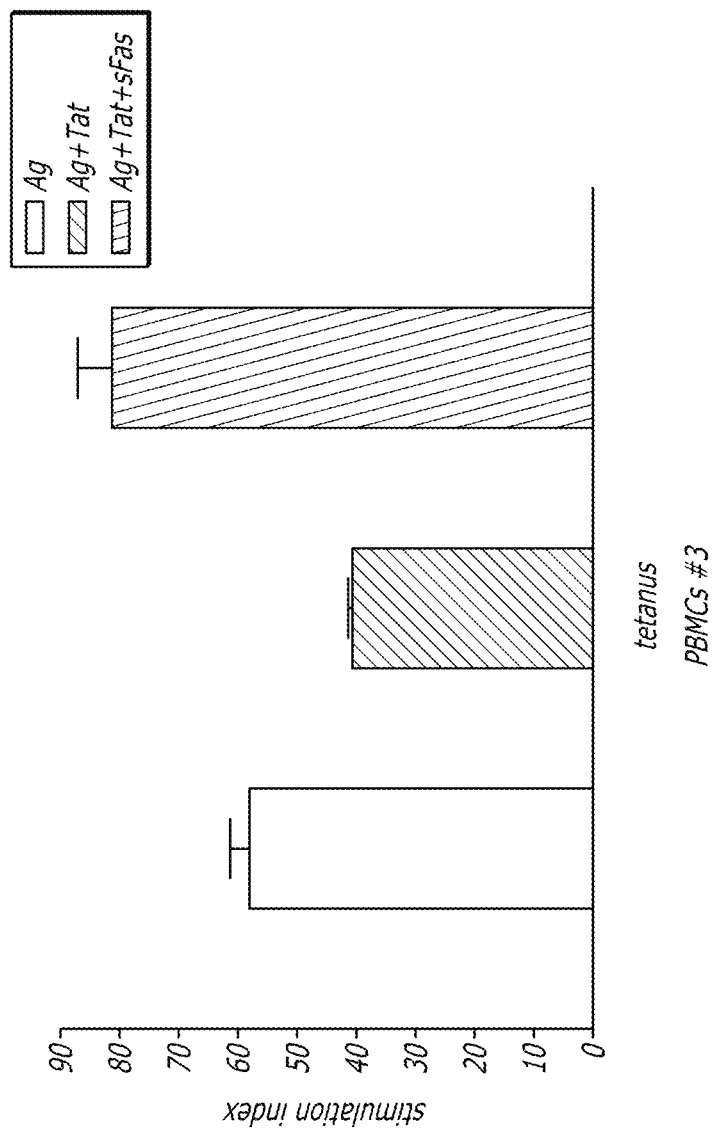
FIG. 9A-B depicts the regulatory and immunosuppressive characteristics of Tat-activated macrophages.
Figure 9B:
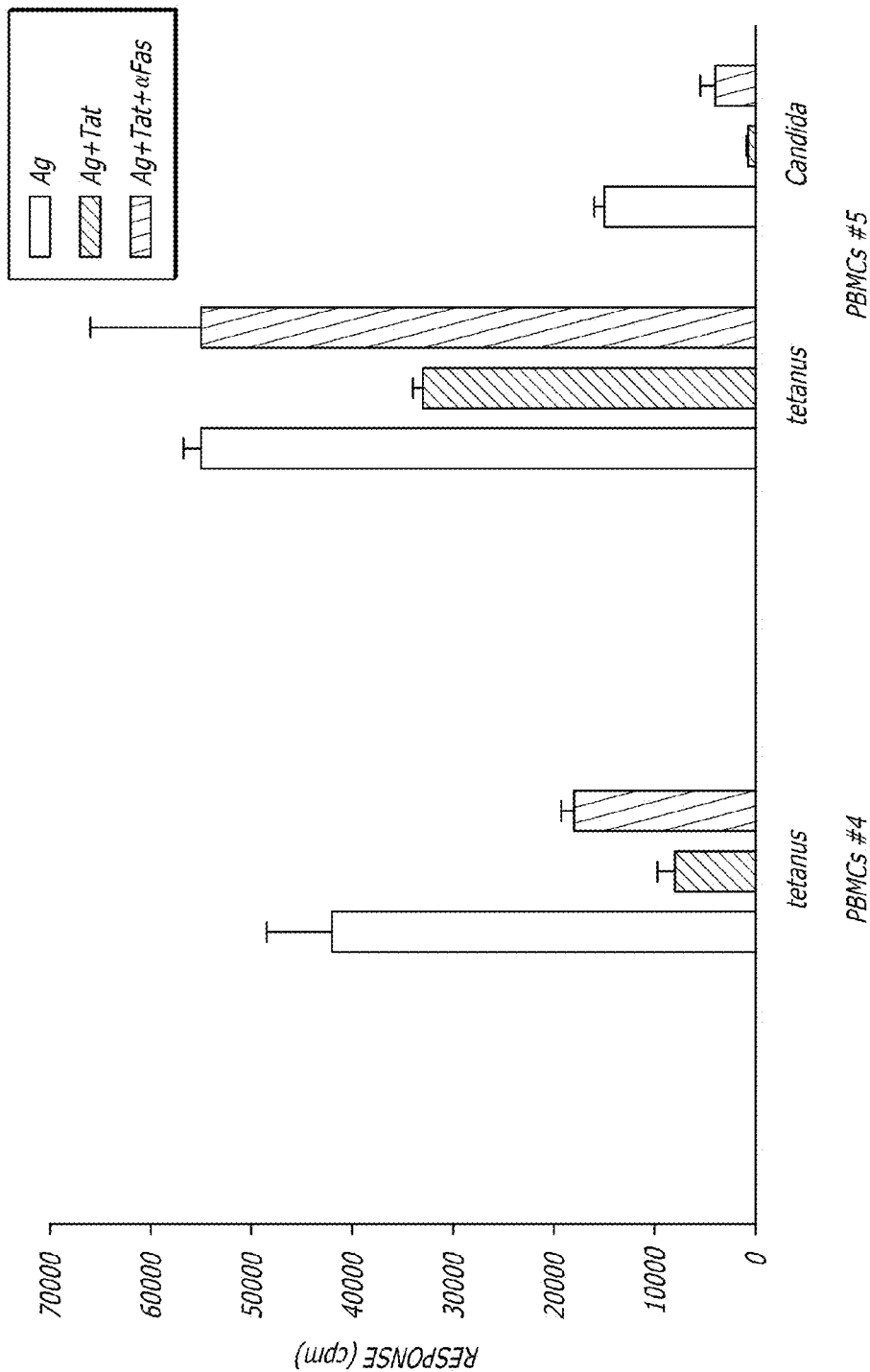

In human cells, Tat-activated macrophages are regulatory and immunosuppressive APC macrophage regulators (ARegs) (FIG. 9). To define the pathway of Tat immunosuppression, through FasL induction on the macrophage, resulting in loss of helper T cell recall responses, T cell proliferation assays were used with recall antigens, tat and FasL antagonists. In FIG. 9A, human PBMCs from one individual were cultured in triplicate for 5 days in either medium (not shown), tetanus antigen (Ag, 0.3 Lf/mL), antigen with the further addition of 50 nM Tat (Ag+Tat) or Ag with 50 nM Tat and recombinant sFas protein (25 µg/mL) to block surface Fas L expressed on macrophages (Ag+Tat+sFas). Tritiated thymidine was added over the last 18 hours, and results are graphed as stimulation index (mean cpm stimulated culture/mean cpm medium control). Results are representative of three similar experiments. At low concentrations of Tat (50 nM), Tat-induced immunosuppression was not only fully reversed by the addition of soluble Fas, but under these conditions, Tat actually became stimulatory (141% relative to antigen treatment alone). FIG. 9B: Proliferation of PBMCs cultured 6 days with either tetanus or *Candida* antigen alone (Ag), compared with cultures in which Tat (Ag+Tat, 125 nM), or Tat (125 nM) and the antagonistic anti-Fas antibody, ZB4 (250 µg/mL, Upstate Biotechnology) also were added (Ag+Tat+αFas). Results are representative of three similar experiments.

Example 4

In Vitro Bioassay for Monocyte Differentiation

The in vitro ultra-sensitive monocyte Tat bioassay is used to assess the immunosuppressant or immunostimulatory activity of the Tat proteins disclosed herein. This assay utilizes fresh monocyte cells substantially purified from human peripheral blood using standard density gradient enrichment procedures or other cell isolation protocols known in the art. The substantially purified monocytes are washed and then cultured in RPMI-1640 supplemented with 10% FBS at 37° C.

The in vitro ultra-sensitive monocyte Tat bioassay is performed using a positive control (FasL, inducing compound) and a negative control (no active compound is added to the culture). Additional suitable positive controls include, but are not limited to, lipopolysaccharide (LPS) and or tumor necrosis factor (TNF-α) at a final concentration of 100 ng/mL and 50 ng/mL, respectively. Test samples (Tat preparations) are run at final concentrations from 50 pM to 50 nM and include Tat, ox-Tat, and other Tat derivatives and mutants.

The test samples and controls are individually mixed with the substantially pure monocytes seeded at a density of $10^6$ cells/mL in round bottom tubes containing RPMI-1640 with 10% FBS (herein referred to collectively as assay cultures). The assay cultures are then incubated for a suitable period of time, preferably from five to six days, at 37° C., in a 5% $CO_2$ environment.

At the end of the incubation period, cells are removed from each assay culture and the presence of any induced FasL expression (for measurement of differentiation into ARegs) or CD86 expression (for differentiation in dendritic cells) is detected by staining with anti-FasL or anti-CD86 antibodies and appropriate fluorescent detection agents. After the cultures have been stained, the fluorescence is detected using a fluorescence activated cell sorter (FACS) system. Control staining is performed using the fluorescent detection system alone and subtracted from the specific anti-FasL or anti-CD86 staining seen in the assay cultures. The greater the percentage of FasL positive cells in a given assay culture, the more immunosuppressant the test sample in the assay culture is. Conversely, if the assay culture contains a predominance of CD86 positive cells, the test sample is identified to be immunostimulatory. Negative controls should always remain non-reactive with the antibodies and the positive control should fall within predetermined ranges.

Example 5

Synthesis of Tat Derivatives

Synthetic peptides were assembled by standard Fmoc chemistry using a CS336X automated synthesizer (C S Bio Co., Menlo Park, Calif.). The peptides were cleaved from the resin using trifluoroacetic acid cleavage/deprotection cocktail compatible with the presence of seven cysteines. Purification was done using reverse phase HPLC. The final product was lyophilized from $H_2O$/acetonitrile. A portion of each synthesis was labeled with Alexa-488. All synthetic Tat derivatives achieved a purity of >95%. Synthetic peptides were reconstituted in phosphate buffer in the presence of 0.1 mM dithiothreitol before use.

Example 6

In Vitro Activity of Tat Derivatives

Figure 10:
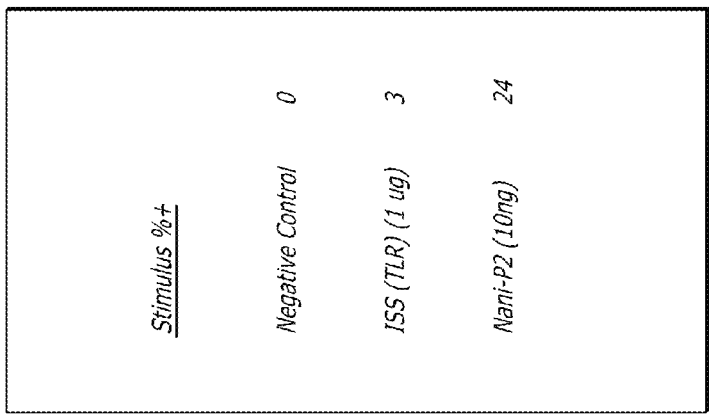
FIG. 10 depicts stimulation of human monocytes with Tat derivatives.
Figure 10:
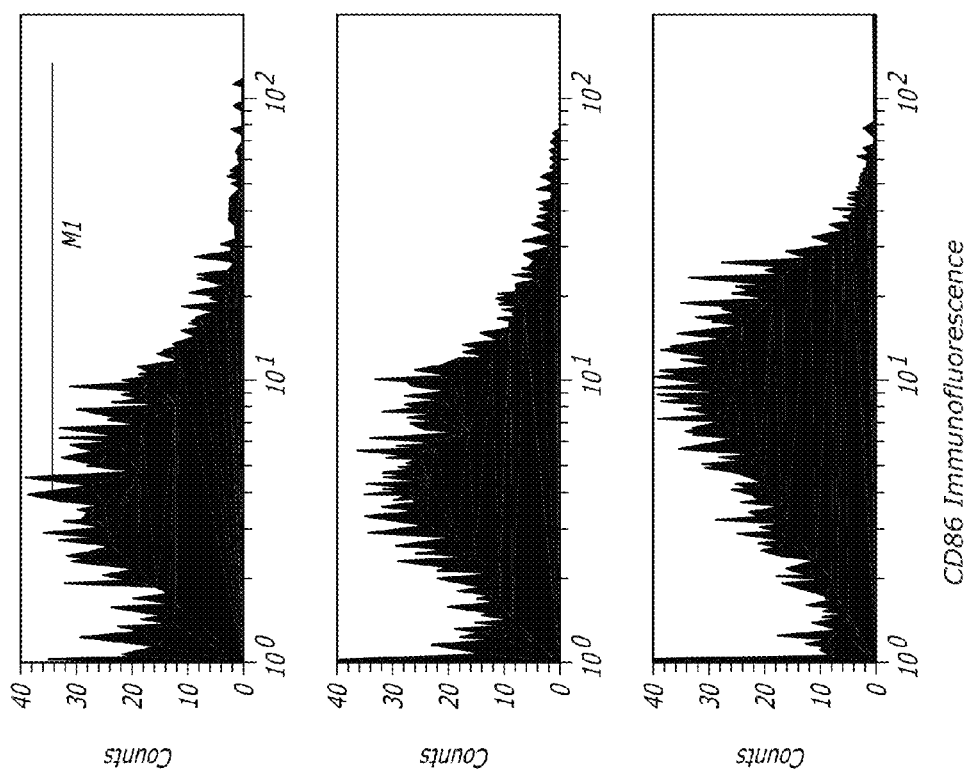

Human monocytes were cultured for 24-28 hours with a Tat derivative (SEQ ID NO:7, Nani-P2), (FIG. 10) or lipopolysaccharide (LPS) (FIG. 11) and the cells were then washed and stained with fluorescent-labeled CD86. The Tat derivative stimulated higher expression of CD86 than either ISS (TLR) or LPS.

Example 7

Live Cell Imaging of Tat Derivatives in T-Lymphocyte and Monocyte Cell Lines

A Jurkat cell line (Clone E6-1, American Type Culture Collection) was maintained in RPMI-1640 (GIBCO), 10% heat-inactivated FBS (GIBCO), 50 U penicillin/50 μg/ml streptomycin (GIBCO), and 2 mM L-Glutamine (GIBCO) at 37° C. in 5% $CO_2$. U937 Cells (American Type Culture Collection) were maintained in RPMI-1640 (GIBCO), 10% heat-inactivated FBS, 50 U penicillin, 50 μg/ml streptomycin, and 2 mM L-Glutamine (GIBCO), 10 mM HEPES (GIBCO), and 0.005% β-mercaptoethanol (Sigma-Aldrich) at 37° C. in 5% $CO_2$.

One million live Jurkat or U937 cells were incubated in complete culture medium for 60-120 minutes at 37° C. in 5% $CO_2$, with or without addition of 5 μM Alexa-488-labeled synthetic Tat derivative. Cells were washed in PBS containing 0.1% heat-inactivated FBS, 1 mM EDTA, and stained with a HOECHST-NucBlue Live Cell Stain (Molecular Probes) by adding 2 drops/mL to the cell suspension. Cells were kept on ice until live cell imaging was performed.

Cells were placed in glass-bottom dishes (MatTek Corp.) and imaged on a Zeiss Axio Observer.Z1 microscope (Carl Zeiss) using a Plan-Neofluor 100x/1.3 objective lens. LEDs (Colibri; Carl Zeiss) at 365 nm and 470 nm were used to excite HOESCHT-stained DNA and Alexa488-labeled protein. Emission was collected with standard DAPI and FITC fluorescence filters. Fluorescence and phase-contrast images were collected with an Orca ER cooled CCD camera (Hamamatsu Photonics).

Figures 12A, 12B, 12C:
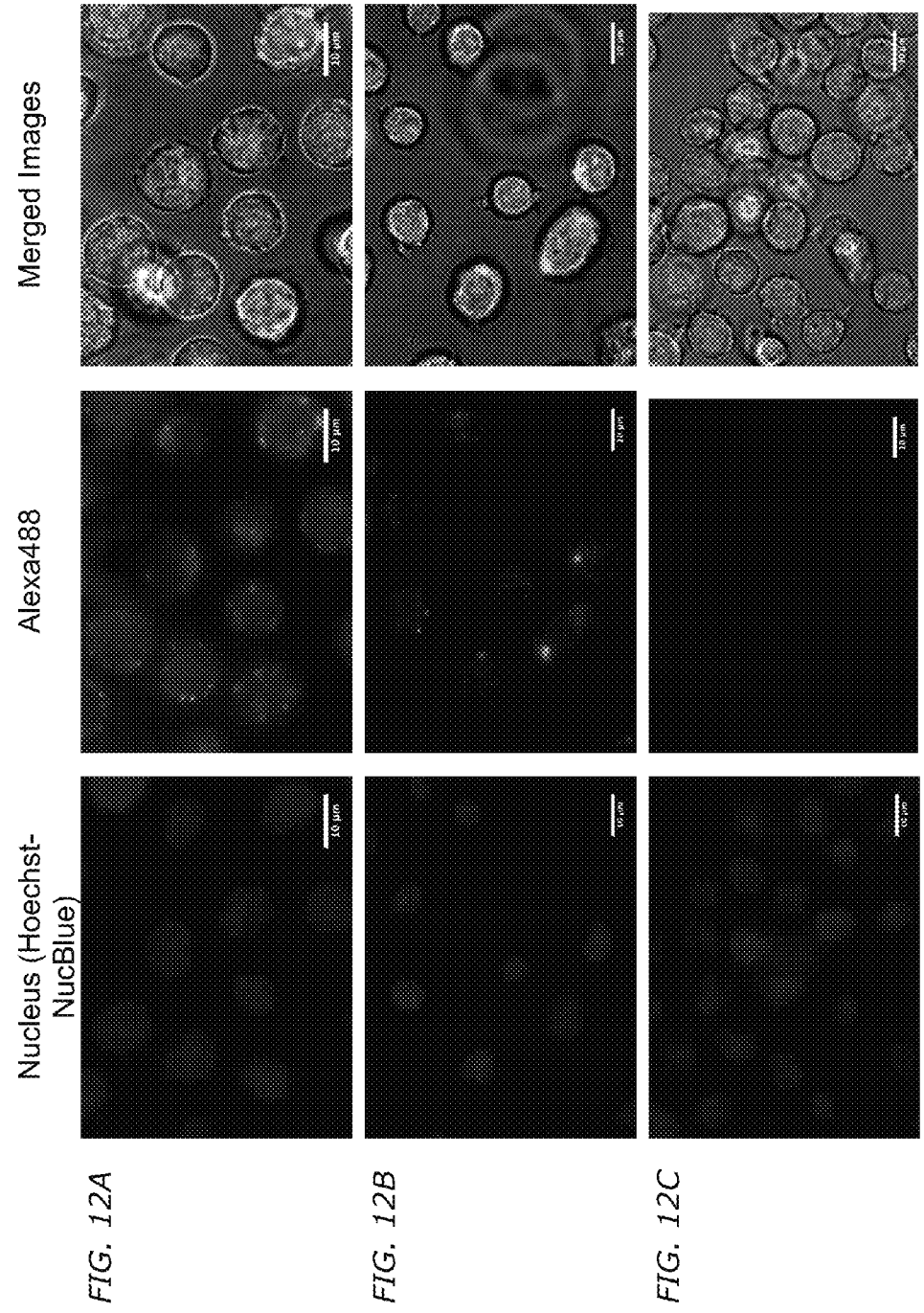
FIG. 12A-C depicts staining of Jurkat cells with Hoechst-NucBlue and Alexa488-labeled Tat derivative SEQ ID NO:9 (FIG. 12A), Alexa488-labeled Tat derivative SEQ ID NO:11 (FIG. 12B), or control (no Tat derivative, FIG. 12C). Left column represents nuclear staining with Hoechst-NucBlue, center column represents Alexa488 staining, and the right column depicts a merge of the left and center images.
Figures 13A, 13B, 13C:
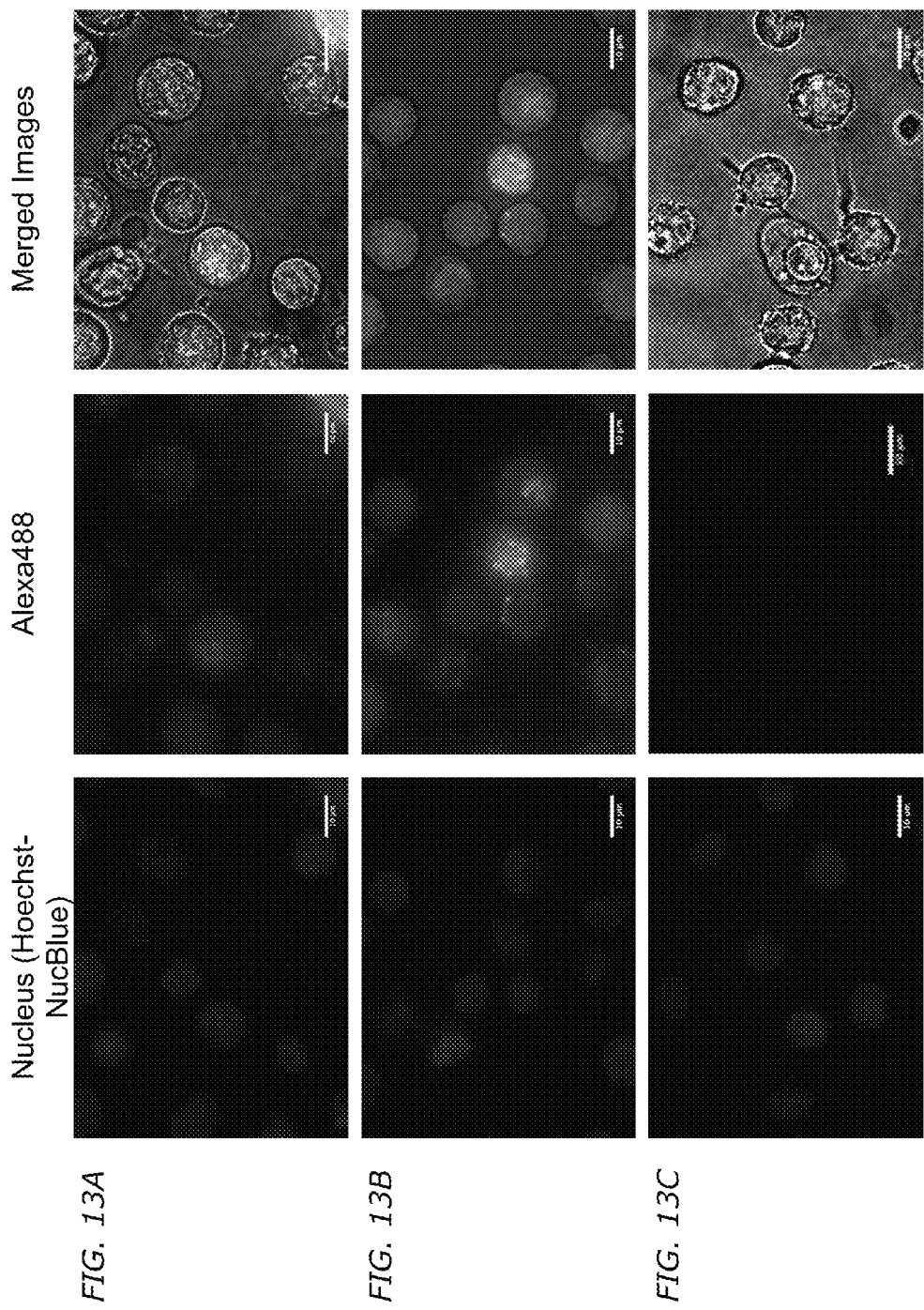
FIG. 13A-C depicts staining of U937 cells with Hoechst-NucBlue and Alexa488-labeled Tat derivative SEQ ID NO:9 (FIG. 13A), Alexa488-labeled Tat derivative SEQ ID NO:11 (FIG. 13B), or control (no Tat derivative, FIG. 13C). Left column represents nuclear staining with Hoechst-NucBlue, center column represents Alexa488 staining, and the right column depicts a merge of the left and center images.
Figure 14B:
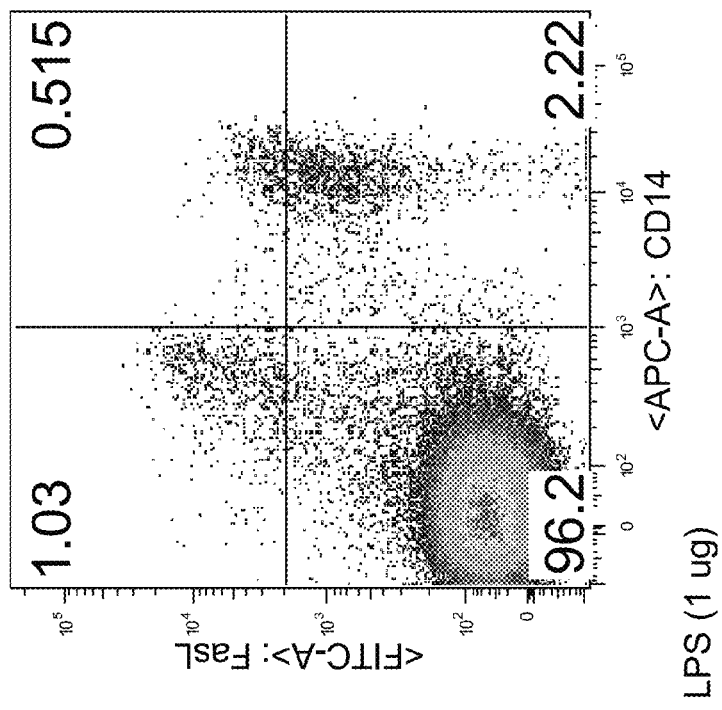
FIG. 14A-C depicts activation of human peripheral blood mononuclear cells (PBMC), as measured by FasL expression, with no stimulus (FIG. 14A), LPS (FIG. 14B), or Tat derivative SEQ ID NO:9 (FIG. 14C).
Figure 14A:
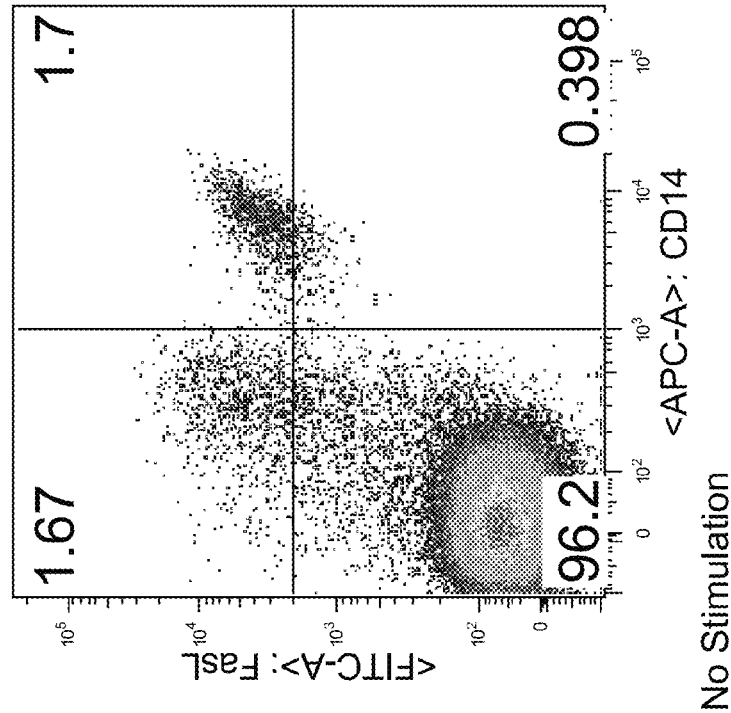
Figure 14C:
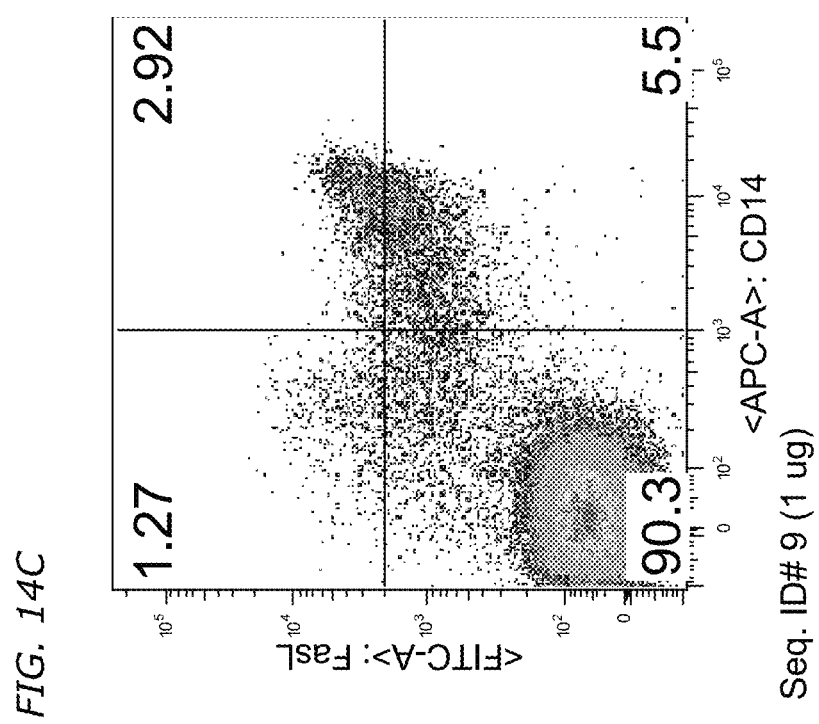
Figure 15:
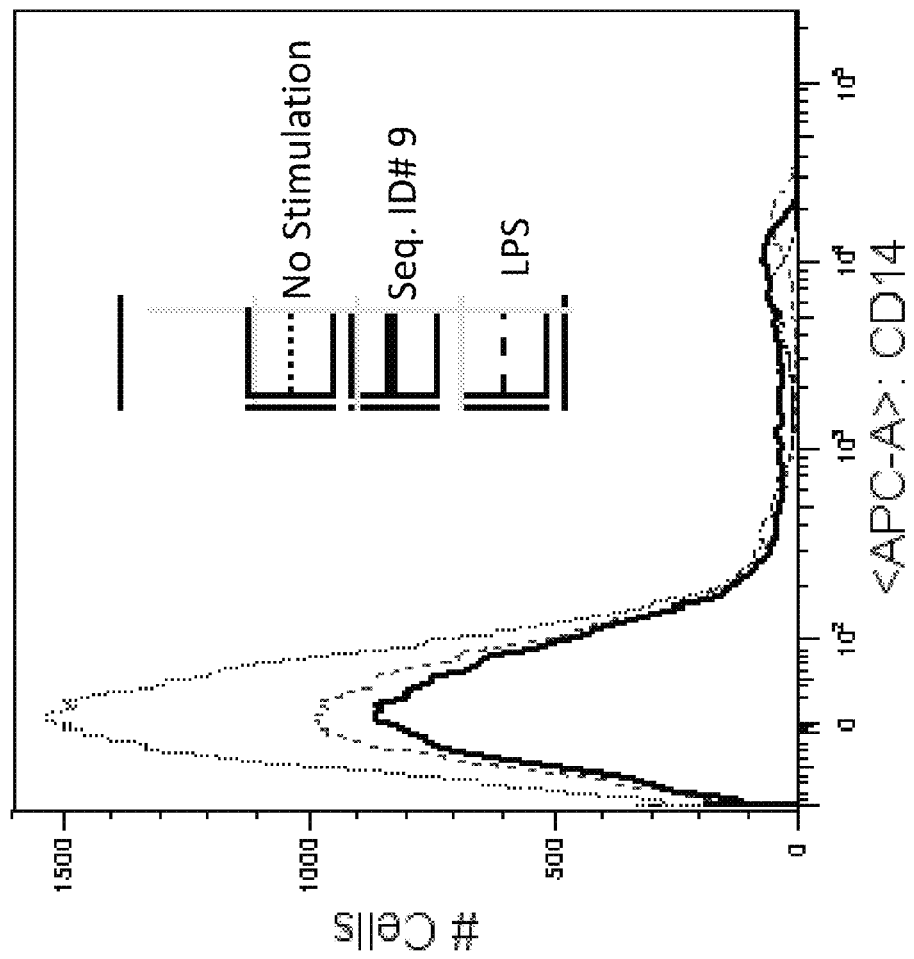
FIG. 15 depicts proliferation of human CD14+ PBMCs, as measured by cell surface CD14 expression, with no stimulus, LPS, or Tat derivative SEQ ID NO:9.
Figure 16:
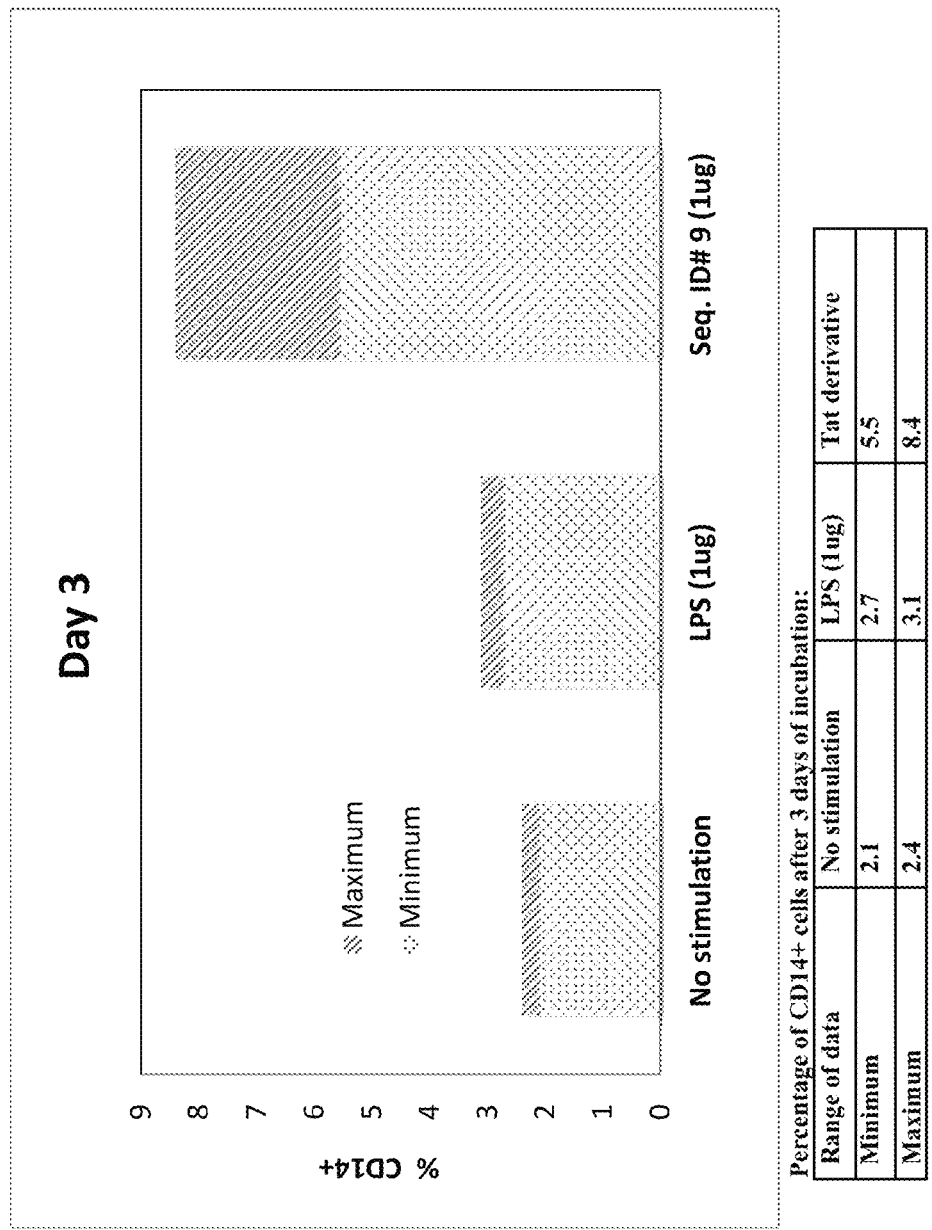
FIG. 16 depicts the percent CD14+ cells in three day cultures of PBMCs treated with LPS, Tat derivative SEQ ID NO:9, or with no stimulus.
Figure 17A:
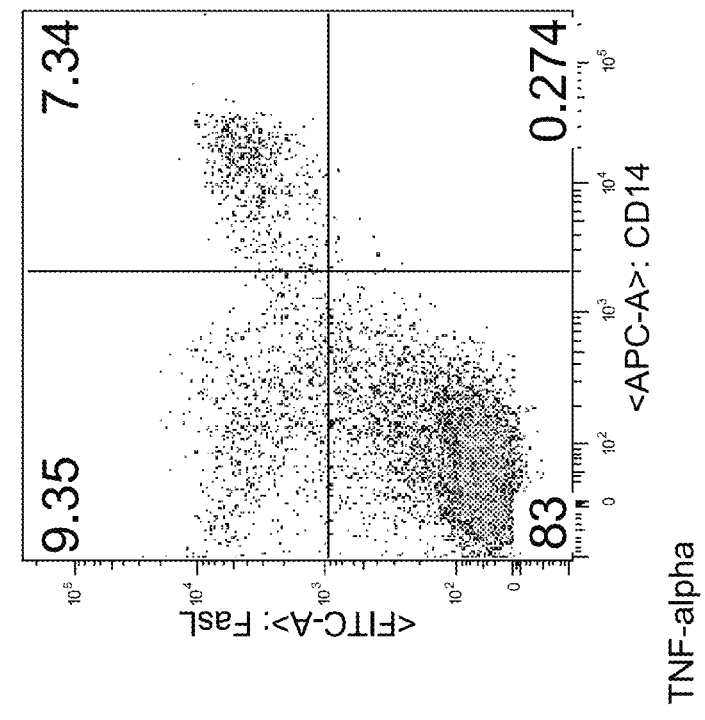
FIG. 17A-E depicts PBMCs expressing both FasL and CD14 after treatment with TNF-alpha (FIG. 17B), LPS (FIG. 17C), Tat derivative SEQ ID NO:9 (FIG. 17D), or with no stimulation (FIG. 17A) after five days in culture.
Figure 17B:
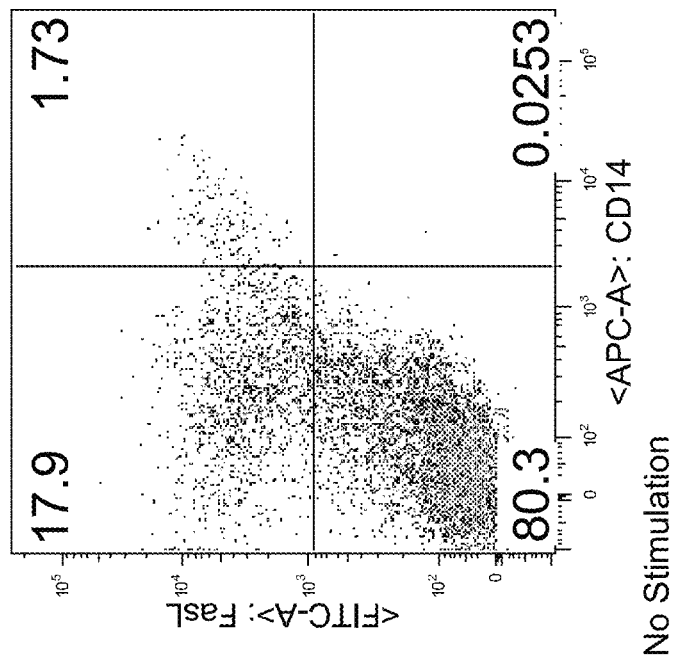
Figure 17D:
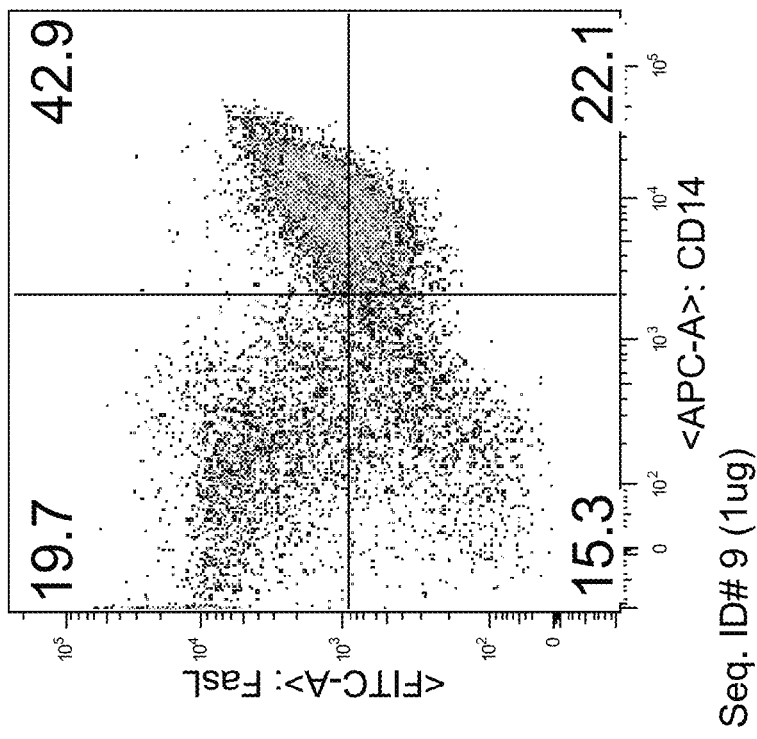
Figure 17C:
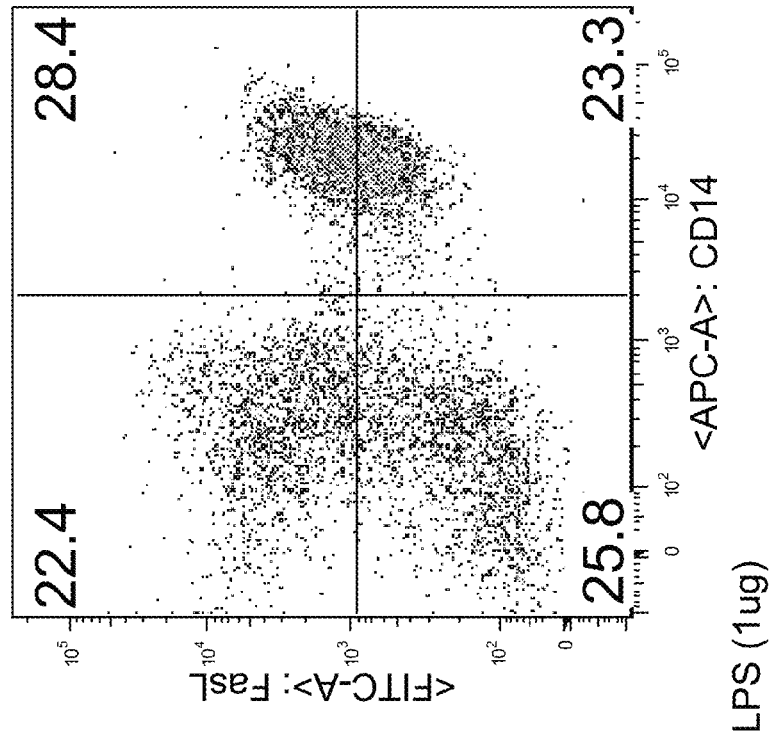
Figure 17E:
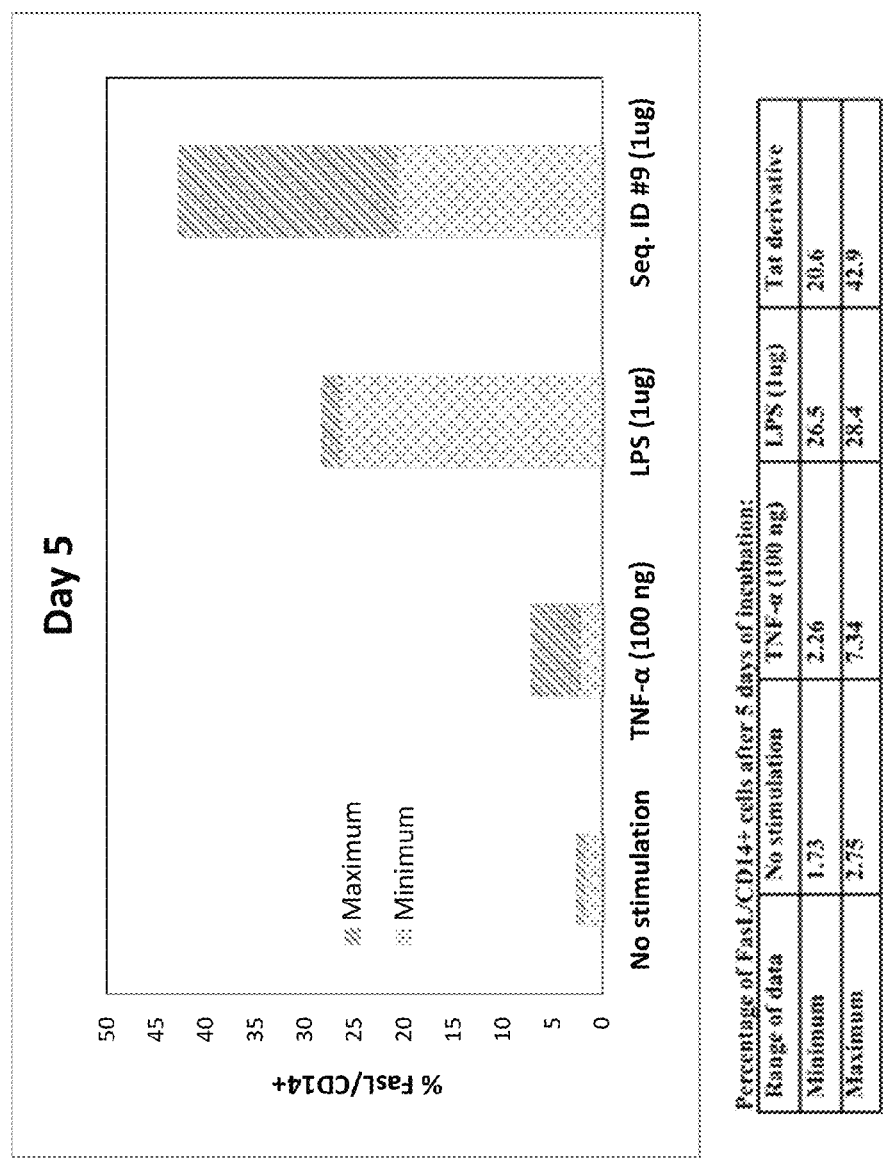

The results, depicted in FIGS. 12 and 13 demonstrate the ability of synthetic Tat derivatives to enter T-lymphocyte and monocytic cell lines in vitro. Jurkat T-cells (FIG. 12) and U937 monocytes (FIG. 13) treated with Alexa488-labeled Tat derivatives show cellular uptake and nuclear localization of fluorescently labeled proteins, highlighting the application of these molecules as cell penetrating peptides endowed with the ability to localize within and around the nucleus.

Example 8

Fluorescence Activated Cell Sorting of Tat Derivative Treated Cells

Human peripheral blood mononuclear cells (PBMC) were isolated from whole blood by density gradient centrifugation with Histopaque separation medium using an ACCUSPIN™ centrifuge tube (Sigma-Aldrich). PBMC cultures were established in RPMI-1640, 10% heat-inactivated fetal bovine serum, 50 U penicillin/50 μg/mL streptomycin, and 2 mM L-Glutamine at a cell density of $1\times10^6$ cells/mL in a 12 well tissue culture plate. PBMC's were incubated in the presence of either no stimulus, 1 μg/ml LPS (Sigma-Aldrich), 100 ng/ml TNF-α (Peprotech), or 1 μg/ml synthetic Tat derivative (SEQ ID NO:9) at 37° C. in 5% $CO_2$. After 3-5 days, cells were harvested, washed, and stained with a mouse anti-human CD14-allophycocyanin (APC) conjugated monoclonal antibody (clone M5E2, BD Biosciences,) or a mouse anti-human Fas Ligand fluorescein (FITC) conjugated monoclonal antibody (clone SB93a, Southern Biotech). Propidium iodide was added to assess viability before fluorescence activated cell sorting (FACS) was performed on a BD LSR II Flow Cytometer (BD Biosciences).

The results, depicted in FIG. 14-17 demonstrate the ability of Tat derivatives to stimulate and increase cell surface CD14 and FasL on human PBMC's in vitro relative to non-stimulated controls by FACS indicating the presence AReg cells capable of suppressing a T-cell immune response.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An immunosuppressive trans-activator of transcription (Tat) derivative polypeptide comprising an amino acid sequence comprising the following domains in the indicated order:

a transcription factor (TF) domain comprising a sequence from an immunosuppressive human immunodeficiency virus (HIV), simian immunodeficiency virus (SIV) Tat protein, hairless or an artificial immunosuppressive sequence, wherein the TF domain comprises the amino acid sequence of one of SEQ ID NOs: 36, 39, 44, 48, 50, 54, 59, 60, or 61;

a cysteine-rich region from lentiviral Tat or a defensin molecule, wherein the cysteine-rich region comprises the amino acid sequence of one of SEQ ID NOs: 37, 40, 41, 43, 45, 47, 49, 51, 53, 55, 57, 58, 62, 63, 64, or 70; and a C-terminal region from a lentiviral Tat protein comprising the amino acid sequence of one of SEQ ID NOs: 38, 42, 46, 47, 49, 52, 53, 68, or 71, wherein the immunosuppressive Tat derivative polypeptide is not SEQ ID NO:6, 7, or 8.

2. The immunosuppressive Tat derivative polypeptide of claim 1, further comprising an arginine-rich domain from a lentiviral Tat protein.

3. The immunosuppressive Tat derivative polypeptide of claim 1, wherein the lentiviral Tat is from HIV-1, HIV-2, SIV, feline immunodeficiency virus (FIV), or equine infectious anemia virus (EIAV).

4. The immunosuppressive Tat derivative polypeptide of claim 1, wherein the TF domain further comprises a repeat sequence comprising $(PVDPRLEPWKHPGSQP)_n$ (SEQ ID NO: 12) at the N-terminus, wherein n=2-10.

5. The immunosuppressive Tat derivative peptide of claim 1, wherein both the cysteine-rich region and the C-terminal region are from the same source and the amino acid sequence of the combined cysteine-rich and C-terminal region is one of SEQ ID NOs: 47, 49, or 53.

6. The immunosuppressive Tat derivative polypeptide of claim 1, wherein the immunosuppressive Tat derivative polypeptide comprises the amino acid sequence of any of SEQ ID NOs: 9-11, 13-35, or 69.

7. A pharmaceutical composition comprising one or more of an immunosuppressive Tat derivative polypeptide according to claim 1 and a pharmaceutically acceptable excipient.

* * * * *

SEQUENCE LISTING

```
<160> NUMBER OF SEQ ID NOS: 72

<210> SEQ ID NO 1
<211> LENGTH: 303
<212> TYPE: DNA
<213> ORGANISM: human immunodeficiency virus

<400> SEQUENCE: 1
```

```
atggagcccg tggaccctcg cctggagccc tggaagcacc cgggcagcca gcccaagacc      60
gcctgcacca catgttactg caagaagtgc tgcttccact gccaggtgtg cttcaccaag     120
aaggccttgg gcatcagcta cggccgcaag aagcgccggc agcgccgccg ggcccctgag     180
gacagccaga cccaccaggt gagccctccc aagcagcccg ctccacagtt ccgcggcgac     240
cctaccggtc ccaaggagag caagaagaag gtggagcgcg agaccgagac ccatcccgtc     300
gac                                                                   303
```

```
<210> SEQ ID NO 2
<211> LENGTH: 101
<212> TYPE: PRT
<213> ORGANISM: human immunodeficiency virus

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala Pro Glu Asp Ser Gln Thr
    50                  55                  60

His Gln Val Ser Pro Pro Lys Gln Pro Ala Pro Gln Phe Arg Gly Asp
65                  70                  75                  80

Pro Thr Gly Pro Lys Glu Ser Lys Lys Lys Val Glu Arg Glu Thr Glu
                85                  90                  95

Thr His Pro Val Asp
            100
```

```
<210> SEQ ID NO 3
<211> LENGTH: 27
<212> TYPE: PRT
<213> ORGANISM: simian immunodeficiency virus

<400> SEQUENCE: 3

Pro Leu Arg Glu Gln Glu Asn Ser Leu Glu Ser Ser Asn Glu Arg Ser
1               5                   10                  15

Ser Cys Ile Leu Glu Ala Asp Ala Thr Thr Pro
            20                  25
```

```
<210> SEQ ID NO 4
<211> LENGTH: 11
<212> TYPE: PRT
<213> ORGANISM: homo sapiens

<400> SEQUENCE: 4

Ser Asn Glu Arg Ser Ser Cys Glu Leu Glu Val
1               5                   10
```

```
<210> SEQ ID NO 5
<211> LENGTH: 16
<212> TYPE: PRT
<213> ORGANISM: human immunodeficiency virus

<400> SEQUENCE: 5

Cys Thr Thr Cys Tyr Cys Lys Lys Cys Cys Phe His Cys Gln Val Cys
1               5                   10                  15
```

```
<210> SEQ ID NO 6
<211> LENGTH: 102
<212> TYPE: PRT
<213> ORGANISM: artificial sequence
<220> FEATURE:
<223> OTHER INFORMATION: Tat derivative polypeptide Nani-P1

<400> SEQUENCE: 6

Met Glu Pro Val Asp Ala Asn Leu Glu Ala Trp Lys His Ala Gly Ser
1               5                   10                  15

Gln Pro Arg Lys Thr Ala Cys Thr Thr Cys Tyr Cys Lys Cys Cys
            20                  25                  30

Phe His Cys Gln Val Cys Phe Thr Arg Lys Gly Leu Gly Ile Ser Tyr
        35                  40                  45

Gly Arg Lys Lys Arg Arg Gln Arg Arg Ala Pro Gln Asp Ser Gln
    50                  55                  60

Thr His Gln Ala Ser Leu Ser Lys Gln Pro Ala Ser Gln Ser Arg Gly
65                  70                  75                  80

Asp Pro Thr Gly Pro Thr Glu Ser Lys Lys Val Glu Arg Glu Thr
                85                  90                  95

Glu Thr Asp Pro Phe Asp
            100

<210> SEQ ID NO 7
<211> LENGTH: 119
<212> TYPE: PRT
<213> ORGANISM: artificial sequence
<220> FEATURE:
<223> OTHER INFORMATION: Tat derivative polypeptide Nani-P2

<400> SEQUENCE: 7

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Leu Arg Lys Gly Leu
        35                  40                  45

Gly Ile Thr Tyr His Ala Phe Arg Thr Arg Lys Lys Ile Ala Ser
    50                  55                  60

Ala Asp Arg Ile Pro Val Pro Gln Gln Ser Ile Ser Ile Arg Gly Arg
65                  70                  75                  80

Asp Ser Gln Thr Thr Gln Glu Ser Gln Lys Lys Val Glu Gln Ala
                85                  90                  95

Lys Ala Asn Leu Arg Ile Ser Arg Lys Asn Leu Gly Asp Glu Thr Arg
            100                 105                 110

Gly Pro Val Gly Ala Gly Asn
        115

<210> SEQ ID NO 8
<211> LENGTH: 130
<212> TYPE: PRT
<213> ORGANISM: artificial sequence
<220> FEATURE:
<223> OTHER INFORMATION: Tat derivative polypeptide Nani-P3

<400> SEQUENCE: 8

Met Glu Thr Pro Leu Lys Glu Gln Glu Asn Ser Leu Glu Ser Cys Arg
1               5                   10                  15

Glu His Ser Ser Ser Ile Ser Glu Val Asp Val Pro Thr Pro Val Ser
            20                  25                  30
```

```
Cys Leu Arg Lys Gly Gly Arg Cys Trp Asn Arg Cys Ile Gly Asn Thr
        35                  40                  45

Arg Gln Ile Gly Ser Cys Gly Val Pro Phe Leu Lys Cys Cys Lys Arg
    50                  55                  60

Lys Pro Phe Thr Arg Lys Gly Leu Gly Ile Ser Tyr Gly Arg Lys Lys
65                  70                  75                  80

Arg Arg Gln Arg Arg Ala Pro Gln Asp Ser Gln Thr His Gln Ala
                85                  90                  95

Ser Leu Ser Lys Gln Pro Ala Ser Gln Ser Arg Gly Asp Pro Thr Gly
                100                 105                 110

Pro Thr Glu Ser Lys Lys Val Glu Arg Glu Thr Glu Thr Asp Pro
            115                 120                 125

Phe Asp
    130
```

<210> SEQ ID NO 9
<211> LENGTH: 101
<212> TYPE: PRT
<213> ORGANISM: artificial sequence
<220> FEATURE:
<223> OTHER INFORMATION: Immunosuppressive Tat derivative polypeptide

<400> SEQUENCE: 9

```
Met Asp Pro Ile Asp Pro Asp Leu Glu Pro Trp Lys His Pro Gly Ser
1               5                   10                  15

Gln Pro Glu Thr Ala Cys Asn Asn Cys Phe Cys Lys Lys Cys Ser Tyr
            20                  25                  30

His Cys Leu Val Cys Phe Gln Lys Lys Gly Leu Gly Ile Ser His Gly
        35                  40                  45

Arg Lys Lys Arg Arg Gln Arg Arg Ser Ala Pro Pro Ser Ser Glu Asp
    50                  55                  60

His Gln Asn Leu Ile Ser Lys Gln Pro Ile Pro Arg Thr Gln Gly Asp
65                  70                  75                  80

Gln Thr Gly Ser Glu Glu Ser Lys Lys Lys Val Glu Ser Lys Thr Glu
                85                  90                  95

Thr Asp Pro Phe Asp
            100
```

<210> SEQ ID NO 10
<211> LENGTH: 101
<212> TYPE: PRT
<213> ORGANISM: artificial sequence
<220> FEATURE:
<223> OTHER INFORMATION: Immunosuppressive Tat derivative polypeptide

<400> SEQUENCE: 10

```
Met Glu Pro Leu Thr Pro His Pro Trp Val Tyr Ser Gly Gly Gln Pro
1               5                   10                  15

```
                              85                  90                  95

Thr Asp Pro Phe Asp
                100

<210> SEQ ID NO 11
<211> LENGTH: 109
<212> TYPE: PRT
<213> ORGANISM: artificial sequence
<220> FEATURE:
<223> OTHER INFORMATION: Immunosuppressive Tat derivative polypeptide

<400> SEQUENCE: 11

Met Ala Gly Pro His Pro Val Ile Val Ile Thr Gly Pro His Glu Glu
1               5                  10                  15

Pro Arg Lys Thr Ala Cys Thr Thr Cys Tyr Cys Lys Lys Cys Cys Phe
                20                  25                  30

His Cys Gln Val Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
        50                  55                  60

His Gln Ala Ser Leu Ser Lys Gln Pro Ala Ser Gln Ser Arg Gly Asp
65                  70                  75                  80

Pro Thr Gly Pro Thr Glu Ser Lys Lys Val Glu Arg Glu Thr Glu
                85                  90                  95

Thr Asp Pro Phe Asp Asp Glu Cys Glu Met Asx Glu Arg
                100                 105

<210> SEQ ID NO 12
<211> LENGTH: 16
<212> TYPE: PRT
<213> ORGANISM: Artificial Sequence
<220> FEATURE:
<223> OTHER INFORMATION: Repeat sequence for Tat derivative peptide TF
      region

<400> SEQUENCE: 12

Pro Val Asp Pro Arg Leu Glu Pro Trp Lys His Pro Gly Ser Gln Pro
1               5                  10                  15

<210> SEQ ID NO 13
<211> LENGTH: 127
<212> TYPE: PRT
<213> ORGANISM: Artificial Sequence
<220> FEATURE:
<223> OTHER INFORMATION: Immunosuppressive Tat derivative polypeptide

<400> SEQUENCE: 13

Met Asp Pro Thr Asp Pro Glu Leu Pro Pro Trp Gln Gln Pro Gly Ser
1               5                  10                  15

Gln Pro Pro Thr Pro Arg Lys Thr Ala Cys Thr Thr Cys Tyr Cys Lys
                20                  25                  30

Lys Cys Cys Phe His Cys Gln Val Cys Phe Leu Gln Lys Gly Leu Gly
            35                  40                  45

Ile Thr Tyr Ala Arg Pro Arg Lys Arg Ala Ala Arg Ser Ile Ser Glu
        50                  55                  60

Asp Asp Ser Ala Pro Thr Glu Pro Tyr Pro Gly Pro Glu Gly Pro Arg
65                  70                  75                  80

Gln Thr Arg Arg Arg Arg Arg Gln Trp Arg Gln Arg Thr Gln
                85                  90                  95

Arg Leu Tyr Leu Gln Gln Arg Ile Phe Glu Ala Ile Phe Gly Ser Arg
```

```
                    100                 105                 110

Thr Ala Ala Leu Glu Asp Ser Leu Gln Gln Leu Gln Ile Ser Asp
        115                 120                 125

<210> SEQ ID NO 14
<211> LENGTH: 123
<212> TYPE: PRT
<213> ORGANISM: Artificial Sequence
<220> FEATURE:
<223> OTHER INFORMATION: Immunosuppressive Tat derivative polypeptide

<400> SEQUENCE: 14

Met Asp Pro Ile Asp Pro Asp Leu Glu Pro Trp Lys His Pro Gly Ser
1               5                   10                  15

Gln Pro Glu Thr Ala Cys Asn Asn Cys Phe Cys Lys Lys Cys Ser Tyr
            20                  25                  30

His Cys Leu Val Cys Phe Leu Gln Lys Gly Leu Gly Ile Thr Tyr Ala
        35                  40                  45

Arg Pro Arg Lys Arg Ala Ala Arg Ser Ile Ser Glu Asp Asp Ser Ala
    50                  55                  60

Pro Thr Glu Pro Tyr Pro Gly Pro Glu Gly Pro Arg Gln Thr Arg Arg
65                  70                  75                  80

Arg Arg Arg Arg Gln Trp Arg Gln Arg Thr Gln Arg Leu Tyr Leu
                85                  90                  95

Gln Gln Arg Ile Phe Glu Ala Ile Phe Gly Ser Arg Thr Ala Ala Leu
            100                 105                 110

Glu Asp Ser Leu Gln Gln Leu Gln Ile Ser Asp
        115                 120

<210> SEQ ID NO 15
<211> LENGTH: 118
<212> TYPE: PRT
<213> ORGANISM: Artificial Sequence
<220> FEATURE:
<223> OTHER INFORMATION: Immunosuppressive Tat derivative polypeptide

<400> SEQUENCE: 15

Met Asp Pro Ile Asp Pro Asp Leu Glu Pro Trp Lys His Pro Gly Ser
1               5                   10                  15

Gln Pro Ala Cys Tyr Cys Arg Ile Pro Ala Cys Ile Ala Gly Glu Arg
            20                  25                  30

Arg Tyr Gly Thr Cys Ile Tyr Gln Gly Arg Leu Trp Ala Phe Cys Cys
        35                  40                  45

Phe His Cys Gln Val Cys Phe Thr Arg Lys Gly Leu Gly Ile Ser Tyr
    50                  55                  60

Gly Arg Lys Lys Arg Arg Gln Arg Arg Arg Ala Pro Gln Asp Ser Gln
65                  70                  75                  80

Thr His Gln Ala Ser Leu Ser Lys Gln Pro Ala Ser Gln Ser Arg Gly
                85                  90                  95

Asp Pro Thr Gly Pro Thr Glu Ser Lys Lys Val Glu Arg Glu Thr
            100                 105                 110

Glu Thr Asp Pro Phe Asp
        115

<210> SEQ ID NO 16
<211> LENGTH: 129
<212> TYPE: PRT
<213> ORGANISM: Artificial Sequence
<220> FEATURE:
```

<223> OTHER INFORMATION: Immunosuppressive Tat derivative polypeptide

<400> SEQUENCE: 16

```
Met Asp Pro Ile Asp Pro Asp Leu Glu Pro Trp Lys His Pro Gly Ser
1               5                   10                  15
Gln Pro Gly Ile Gly Asp Pro Val Thr Cys Leu Lys Ser Gly Ala Ile
            20                  25                  30
Cys His Pro Val Phe Cys Pro Arg Arg Tyr Lys Gln Ile Gly Thr Cys
        35                  40                  45
Gly Leu Pro Gly Thr Lys Cys Cys Lys Lys Pro Phe His Cys Gln Val
    50                  55                  60
Cys Phe Thr Arg Lys Gly Leu Gly Ile Ser Tyr Gly Arg Lys Lys Arg
65                  70                  75                  80
Arg Gln Arg Arg Arg Ala Pro Gln Asp Ser Gln Thr His Gln Ala Ser
                85                  90                  95
Leu Ser Lys Gln Pro Ala Ser Gln Ser Arg Gly Asp Pro Thr Gly Pro
            100                 105                 110
Thr Glu Ser Lys Lys Lys Val Glu Arg Glu Thr Glu Thr Asp Pro Phe
        115                 120                 125
Asp
```

<210> SEQ ID NO 17
<211> LENGTH: 82
<212> TYPE: PRT
<213> ORGANISM: Artificial Sequence
<220> FEATURE:
<223> OTHER INFORMATION: Immunosuppressive Tat derivative polypeptide

<400> SEQUENCE: 17

```
Met Glu Pro Val Asp Pro Arg Leu Glu Pro Trp Lys His Pro Gly Ser
1               5                   10                  15
Gln Pro Lys Thr Ala Cys Asn Asn Cys His Cys Lys Val Cys Cys Tyr
            20                  25                  30
His Cys Val Tyr Cys Phe Thr Lys Lys Gly Leu Gly Ile Ser Tyr Gly
        35                  40                  45
Arg Lys Lys Arg Arg Arg Pro Ala Arg Thr Ala Asp Lys Asp Gln Asp
    50                  55                  60
Asn Gln Asp Pro Val Ser Lys Gln Ser Leu Ala Gly Thr Arg Ser Gln
65                  70                  75                  80
Gln Glu
```

<210> SEQ ID NO 18
<211> LENGTH: 100
<212> TYPE: PRT
<213> ORGANISM: Artificial Sequence
<220> FEATURE:
<223> OTHER INFORMATION: Immunosuppressive Tat derivative polypeptide

<400> SEQUENCE: 18

```
Met Asp Pro Ile Asp Pro Asp Leu Glu Pro Trp Lys His Pro Gly Ser
1               5                   10                  15
Gln Pro Thr Thr Ala Cys Ser Lys Cys Tyr Cys Lys Ile Cys Cys Trp
            20                  25                  30
His Cys Gln Leu Cys Leu Lys Lys Gly Leu Gly Ile Ser Tyr Gly Arg
        35                  40                  45
Lys Lys Arg Lys His Arg Arg Gly Thr Pro Gln Ser Ser Lys Asp His
    50                  55                  60
```

```
Gln Asn Pro Ile Pro Glu Gln Pro Leu Pro Ile Arg Gly Asn Pro
 65                  70                  75                  80

Thr Asp Pro Lys Glu Ser Lys Lys Glu Val Ala Ser Lys Ala Glu Thr
                 85                  90                  95

Asp Pro Phe Asp
            100

<210> SEQ ID NO 19
<211> LENGTH: 102
<212> TYPE: PRT
<213> ORGANISM: Artificial Sequence
<220> FEATURE:
<223> OTHER INFORMATION: Immunosuppressive Tat derivative polypeptide

<400> SEQUENCE: 19

Met Glu Pro Leu Thr Pro His Pro Trp Val Tyr Ser Gly Gly Gln Pro
  1               5                  10                  15

Lys Val Pro Glu Thr Ala Cys Asn Asn Cys Phe Cys Lys Lys Cys Ser
                 20                  25                  30

Tyr His Cys Leu Val Cys Phe Gln Lys Lys Gly Leu Gly Ile Ser His
                 35                  40                  45

Gly Arg Lys Lys Arg Arg Gln Arg Arg Ser Ala Pro Pro Ser Ser Glu
 50                  55                  60

Asp His Gln Asn Leu Ile Ser Lys Gln Pro Ile Pro Arg Thr Gln Gly
 65                  70                  75                  80

Asp Gln Thr Gly Ser Glu Glu Ser Lys Lys Lys Val Glu Ser Lys Thr
                 85                  90                  95

Glu Thr Asp Pro Phe Asp
            100

<210> SEQ ID NO 20
<211> LENGTH: 99
<212> TYPE: PRT
<213> ORGANISM: Artificial Sequence
<220> FEATURE:
<223> OTHER INFORMATION: Immunosuppressive Tat derivative polypeptide

<400> SEQUENCE: 20

Met Ala Gly Pro His Pro Val Ile Val Ile Thr Gly Pro His Glu Glu
  1               5                  10                  15

Pro Thr Thr Ala Cys Ser Lys Cys Tyr Cys Lys Ile Cys Cys Trp His
                 20                  25                  30

Cys Gln Leu Cys Leu Lys Lys Gly Leu Gly Ile Ser Tyr Gly Arg Lys
                 35                  40                  45

Lys Arg Lys His Arg Arg Gly Thr Pro Gln Ser Ser Lys Asp His Gln
 50                  55                  60

Asn Pro Ile Pro Glu Gln Pro Leu Pro Ile Arg Gly Asn Pro Thr
 65                  70                  75                  80

Asp Pro Lys Glu Ser Lys Lys Glu Val Ala Ser Lys Ala Glu Thr Asp
                 85                  90                  95

Pro Phe Asp

<210> SEQ ID NO 21
<211> LENGTH: 100
<212> TYPE: PRT
<213> ORGANISM: Artificial Sequence
<220> FEATURE:
<223> OTHER INFORMATION: Immunosuppressive Tat derivative polypeptide

<400> SEQUENCE: 21
```

```
Met Ala Gly Pro His Pro Val Ile Val Ile Thr Gly Pro His Glu Glu
1               5                   10                  15

Pro Glu Thr Ala Cys Asn Asn Cys Phe Cys Lys Lys Cys Ser Tyr His
            20                  25                  30

Cys Leu Val Cys Phe Gln Lys Lys Gly Leu Gly Ile Ser His Gly Arg
        35                  40                  45

Lys Lys Arg Arg Gln Arg Arg Ser Ala Pro Pro Ser Ser Glu Asp His
    50                  55                  60

Gln Asn Leu Ile Ser Lys Gln Pro Ile Pro Arg Thr Gln Gly Asp Gln
65                  70                  75                  80

Thr Gly Ser Glu Glu Ser Lys Lys Lys Val Glu Ser Lys Thr Glu Thr
                85                  90                  95

Asp Pro Phe Asp
            100
```

```
<210> SEQ ID NO 22
<211> LENGTH: 113
<212> TYPE: PRT
<213> ORGANISM: Artificial Sequence
<220> FEATURE:
<223> OTHER INFORMATION: Immunosuppressive Tat derivative polypeptide

<400> SEQUENCE: 22
```

```
Met Glu Pro Leu Thr Pro His Pro Trp Val Tyr Ser Gly Gly Gln Pro
1               5                   10                  15

Lys Val Pro Arg Thr Cys His Cys Arg Ser Arg Cys Leu Arg Arg Glu
            20                  25                  30

Ser Asn Ser Gly Ser Cys Asn Ile Asn Gly Arg Ile Ser Ser Leu Cys
        35                  40                  45

Cys Phe Leu Lys Lys Gly Leu Gly Ile Ser Tyr Glu Lys Ser His Arg
    50                  55                  60

Arg Arg Arg Thr Pro Lys Lys Ala Lys Ala Asn Thr Ser Ser Ala Ser
65                  70                  75                  80

Asn Glu Pro Ile Pro Asn Arg Ile Arg Leu Cys Gln Pro Lys Lys Ala
                85                  90                  95

Lys Lys Glu Thr Val Glu Ala Ala Val Ala Thr Ala Pro Gly Leu Gly
            100                 105                 110

Arg
```

```
<210> SEQ ID NO 23
<211> LENGTH: 111
<212> TYPE: PRT
<213> ORGANISM: Artificial Sequence
<220> FEATURE:
<223> OTHER INFORMATION: Immunosuppressive Tat derivative polypeptide

<400> SEQUENCE: 23
```

```
Met Ala Gly Pro His Pro Val Ile Val Ile Thr Gly Pro His Glu Glu
1               5                   10                  15

Pro Arg Thr Cys His Cys Arg Ser Arg Cys Leu Arg Arg Glu Ser Asn
            20                  25                  30

Ser Gly Ser Cys Asn Ile Asn Gly Arg Ile Ser Ser Leu Cys Cys Phe
        35                  40                  45

Leu Lys Lys Gly Leu Gly Ile Ser Tyr Glu Lys Ser His Arg Arg Arg
    50                  55                  60

Arg Thr Pro Lys Lys Ala Lys Ala Asn Thr Ser Ser Ala Ser Asn Glu
65                  70                  75                  80
```

Pro Ile Pro Asn Arg Ile Arg Leu Cys Gln Pro Lys Lys Ala Lys Lys
             85                  90                  95

Glu Thr Val Glu Ala Ala Val Ala Thr Ala Pro Gly Leu Gly Arg
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: Immunosuppressive Tat derivative polypeptide

<400> SEQUENCE: 24

Met Asp Pro Ile Asp Pro Asp Leu Glu Pro Trp Lys His Pro Gly Ser
1               5                   10                  15

Gln Pro Arg Thr Cys His Cys Arg Ser Arg Cys Leu Arg Glu Ser
            20                  25                  30

Asn Ser Gly Ser Cys Asn Ile Asn Gly Arg Ile Ser Ser Leu Cys Cys
            35                  40                  45

Phe Leu Lys Lys Gly Leu Gly Ile Ser Tyr Glu Lys Ser His Arg Arg
    50                  55                  60

Arg Arg Thr Pro Lys Lys Ala Lys Ala Asn Thr Ser Ser Ala Ser Asn
65                  70                  75                  80

Glu Pro Ile Pro Asn Arg Ile Arg Leu Cys Gln Pro Lys Lys Ala Lys
                85                  90                  95

Lys Glu Thr Val Glu Ala Ala Val Ala Thr Ala Pro Gly Leu Gly Arg
            100                 105                 110

<210> SEQ ID NO 25
<211> LENGTH: 101
<212> TYPE: PRT
<213> ORGANISM: Artificial Sequence
<220> FEATURE:
<223> OTHER INFORMATION: Immunosuppressive Tat derivative polypeptide

<400> SEQUENCE: 25

Met Glu Pro Leu Thr Pro His Pro Trp Val Tyr Ser Gly Gly Gln Pro
1               5                   10                  15

Lys Val Pro Leu Glu Ala Cys Tyr Asn Lys Cys Tyr Cys Lys Arg Cys
            20                  25                  30

Cys Tyr His Cys Gln His Cys Phe Leu Lys Lys Gly Leu Gly Ile Cys
            35                  40                  45

Tyr Glu Gln Gln Arg Arg Arg Thr Pro Lys Lys Thr Lys Ala Asn Thr
    50                  55                  60

Ser Ser Ala Ser Asp Lys Ser Leu Ser Arg Arg Ala Arg Asn Cys Gln
65                  70                  75                  80

Pro Lys Lys Glu Lys Lys Glu Thr Val Glu Ala Glu Val Ala Thr Asp
                85                  90                  95

Leu Gly Leu Gly Arg
            100

<210> SEQ ID NO 26
<211> LENGTH: 99
<212> TYPE: PRT
<213> ORGANISM: Artificial Sequence
<220> FEATURE:
<223> OTHER INFORMATION: Immunosuppressive Tat derivative polypeptide

<400> SEQUENCE: 26

Met Ala Gly Pro His Pro Val Ile Val Ile Thr Gly Pro His Glu Glu
1               5                   10                  15

Pro Leu Glu Ala Cys Tyr Asn Lys Cys Tyr Cys Lys Arg Cys Cys Tyr
            20                  25                  30

His Cys Gln His Cys Phe Leu Lys Lys Gly Leu Gly Ile Cys Tyr Glu
        35                  40                  45

Gln Gln Arg Arg Arg Thr Pro Lys Lys Thr Lys Ala Asn Thr Ser Ser
    50                  55                  60

Ala Ser Asp Lys Ser Leu Ser Arg Arg Ala Arg Asn Cys Gln Pro Lys
65                  70                  75                  80

Lys Glu Lys Lys Glu Thr Val Glu Ala Glu Val Ala Thr Asp Leu Gly
                85                  90                  95

Leu Gly Arg

<210> SEQ ID NO 27
<211> LENGTH: 100
<212> TYPE: PRT
<213> ORGANISM: Artificial Sequence
<220> FEATURE:
<223> OTHER INFORMATION: Immunosuppressive Tat derivative polypeptide

<400> SEQUENCE: 27

Met Asp Pro Ile Asp Pro Asp Leu Glu Pro Trp Lys His Pro Gly Ser
1               5                   10                  15

Gln Pro Leu Glu Ala Cys Tyr Asn Lys Cys Tyr Cys Lys Arg Cys Cys
            20                  25                  30

Tyr His Cys Gln His Cys Phe Leu Lys Lys Gly Leu Gly Ile Cys Tyr
        35                  40                  45

Glu Gln Gln Arg Arg Arg Thr Pro Lys Lys Thr Lys Ala Asn Thr Ser
    50                  55                  60

Ser Ala Ser Asp Lys Ser Leu Ser Arg Arg Ala Arg Asn Cys Gln Pro
65                  70                  75                  80

Lys Lys Glu Lys Lys Glu Thr Val Glu Ala Glu Val Ala Thr Asp Leu
                85                  90                  95

Gly Leu Gly Arg
            100

<210> SEQ ID NO 28
<211> LENGTH: 122
<212> TYPE: PRT
<213> ORGANISM: Artificial Sequence
<220> FEATURE:
<223> OTHER INFORMATION: Immunosuppressive Tat derivative polypeptide

<400> SEQUENCE: 28

Met Met Glu Pro Val Asp Pro Asp Leu Pro Lys Glu Gln His Pro Pro
1               5                   10                  15

Ala Thr Pro Arg Cys Glu Ser Cys Lys Leu Gly Arg Gly Arg Cys Arg
            20                  25                  30

Lys Glu Cys Leu Glu Asn Glu Lys Pro Asp Gly Arg Cys Arg Leu Asn
        35                  40                  45

Phe Leu Cys Cys Phe His Cys Gln Val Cys Phe Thr Arg Lys Gly Leu
    50                  55                  60

Gly Ile Ser Tyr Gly Arg Lys Lys Arg Arg Gln Arg Arg Ala Pro
65                  70                  75                  80

Gln Asp Ser Gln Thr His Gln Ala Ser Leu Ser Lys Gln Pro Ala Ser
                85                  90                  95

Gln Ser Arg Gly Asp Pro Thr Gly Pro Thr Glu Ser Lys Lys Val
            100                 105                 110

Glu Arg Glu Thr Glu Thr Asp Pro Phe Asp
        115                 120

<210> SEQ ID NO 29
<211> LENGTH: 121
<212> TYPE: PRT
<213> ORGANISM: Artificial Sequence
<220> FEATURE:
<223> OTHER INFORMATION: Immunosuppressive Tat derivative polypeptide

<400> SEQUENCE: 29

Met Glu Pro Leu Thr Pro His Pro Trp Val Tyr Ser Gly Gly Gln Pro
1               5                   10                  15

Lys Val Pro Cys Glu Ser Cys Lys Leu Gly Arg Gly Arg Cys Arg Lys
            20                  25                  30

Glu Cys Leu Glu Asn Glu Lys Pro Asp Gly Arg Cys Arg Leu Asn Phe
        35                  40                  45

Leu Cys Cys Phe His Cys Gln Val Cys Phe Thr Arg Lys Gly Leu Gly
    50                  55                  60

Ile Ser Tyr Gly Arg Lys Lys Arg Arg Gln Arg Arg Ala Pro Gln
65                  70                  75                  80

Asp Ser Gln Thr His Gln Ala Ser Leu Ser Lys Gln Pro Ala Ser Gln
                85                  90                  95

Ser Arg Gly Asp Pro Thr Gly Pro Thr Glu Ser Lys Lys Lys Val Glu
            100                 105                 110

Arg Glu Thr Glu Thr Asp Pro Phe Asp
        115                 120

<210> SEQ ID NO 30
<211> LENGTH: 120
<212> TYPE: PRT
<213> ORGANISM: Artificial Sequence
<220> FEATURE:
<223> OTHER INFORMATION: Immunosuppressive Tat derivative polypeptide

<400> SEQUENCE: 30

Met Asp Pro Ile Asp Pro Asp Leu Glu Pro Trp Lys His Pro Gly Ser
1               5                   10                  15

Gln Pro Cys Glu Ser Cys Lys Leu Gly Arg Gly Arg Cys Arg Lys Glu
            20                  25                  30

Cys Leu Glu Asn Glu Lys Pro Asp Gly Arg Cys Arg Leu Asn Phe Leu
        35                  40                  45

Cys Cys Phe His Cys Gln Val Cys Phe Thr Arg Lys Gly Leu Gly Ile
    50                  55                  60

Ser Tyr Gly Arg Lys Lys Arg Arg Gln Arg Arg Ala Pro Gln Asp
65                  70                  75                  80

Ser Gln Thr His Gln Ala Ser Leu Ser Lys Gln Pro Ala Ser Gln Ser
                85                  90                  95

Arg Gly Asp Pro Thr Gly Pro Thr Glu Ser Lys Lys Lys Val Glu Arg
            100                 105                 110

Glu Thr Glu Thr Asp Pro Phe Asp
        115                 120

<210> SEQ ID NO 31
<211> LENGTH: 119
<212> TYPE: PRT
<213> ORGANISM: Artificial Sequence

```
<220> FEATURE:
<223> OTHER INFORMATION: Immunosuppressive Tat derivative polypeptide

<400> SEQUENCE: 31

Met Ala Gly Pro His Pro Val Ile Val Ile Thr Gly Pro His Glu Glu
1               5                   10                  15

Pro Cys Glu Ser Cys Lys Leu Gly Arg Gly Arg Cys Arg Lys Glu Cys
                20                  25                  30

Leu Glu Asn Glu Lys Pro Asp Gly Arg Cys Arg Leu Asn Phe Leu Cys
            35                  40                  45

Cys Phe His Cys Gln Val Cys Phe Thr Arg Lys Gly Leu Gly Ile Ser
        50                  55                  60

Tyr Gly Arg Lys Lys Arg Arg Gln Arg Arg Arg Ala Pro Gln Asp Ser
65                  70                  75                  80

Gln Thr His Gln Ala Ser Leu Ser Lys Gln Pro Ala Ser Gln Ser Arg
                85                  90                  95

Gly Asp Pro Thr Gly Pro Thr Glu Ser Lys Lys Lys Val Glu Arg Glu
            100                 105                 110

Thr Glu Thr Asp Pro Phe Asp
        115

<210> SEQ ID NO 32
<211> LENGTH: 126
<212> TYPE: PRT
<213> ORGANISM: Artificial Sequence
<220> FEATURE:
<223> OTHER INFORMATION: Immunosuppressive Tat derivative polypeptide

<400> SEQUENCE: 32

Met Glu Pro Val Asp Pro Arg Leu Glu Pro Trp Lys His Pro Gly Ser
1               5                   10                  15

Gln Pro Pro Glu Pro Val Asp Pro Arg Leu Glu Pro Trp Lys His Pro
                20                  25                  30

Gly Ser Gln Pro Lys Thr Ala Cys Asn Asn Cys His Cys Lys Val Cys
            35                  40                  45

Cys Tyr His Cys Val Tyr Cys Phe Phe His Cys Gln Val Cys Phe Thr
        50                  55                  60

Arg Lys Gly Leu Gly Ile Ser Tyr Gly Arg Lys Lys Arg Gln Arg
65                  70                  75                  80

Arg Arg Ala Pro Gln Asp Ser Gln Thr His Gln Ala Ser Leu Ser Lys
                85                  90                  95

Gln Pro Ala Ser Gln Ser Arg Gly Asp Pro Thr Gly Pro Thr Glu Ser
            100                 105                 110

Lys Lys Lys Val Glu Arg Glu Thr Glu Thr Asp Pro Phe Asp
        115                 120                 125

<210> SEQ ID NO 33
<211> LENGTH: 112
<212> TYPE: PRT
<213> ORGANISM: Artificial Sequence
<220> FEATURE:
<223> OTHER INFORMATION: Immunosuppressive Tat derivative polypeptide

<400> SEQUENCE: 33

Met Glu Pro Leu Thr Pro His Pro Trp Val Tyr Ser Gly Gly Gln Pro
1               5                   10                  15

Lys Val Pro Leu Arg Cys Ile Cys Arg Arg Gly Ile Cys Arg Leu Leu
                20                  25                  30
```

```
Gln Arg Arg Tyr Gly Ser Cys Ala Phe Pro Gly Arg Leu Tyr Arg Ile
        35                  40                  45

Cys Cys Phe Leu Lys Lys Gly Leu Gly Ile Cys Tyr Glu Gln Gln Arg
 50                  55                  60

Arg Arg Thr Pro Lys Lys Thr Lys Ala Asn Thr Ser Ser Ala Ser Asp
 65                  70                  75                  80

Lys Ser Leu Ser Arg Arg Ala Arg Asn Cys Gln Pro Lys Lys Glu Lys
                 85                  90                  95

Lys Glu Thr Val Glu Ala Glu Val Ala Thr Asp Leu Gly Leu Gly Arg
                100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Immunosuppressive Tat derivative polypeptide

<400> SEQUENCE: 34

Met Ala Gly Pro His Pro Val Ile Val Ile Thr Gly Pro His Glu Glu
 1               5                  10                  15

Pro Leu Arg Cys Ile Cys Arg Arg Gly Ile Cys Arg Leu Leu Gln Arg
                 20                  25                  30

Arg Tyr Gly Ser Cys Ala Phe Pro Gly Arg Leu Tyr Arg Ile Cys Cys
             35                  40                  45

Phe Leu Lys Lys Gly Leu Gly Ile Cys Tyr Glu Gln Gln Arg Arg Arg
 50                  55                  60

Thr Pro Lys Lys Thr Lys Ala Asn Th

```
<211> LENGTH: 21
<212> TYPE: PRT
<213> ORGANISM: Simian immunodeficiency virus

<400> SEQUENCE: 36

Met Asp Pro Thr Asp Pro Glu Leu P

<210> SEQ ID NO 41
<211> LENGTH: 30
<212> TYPE: PRT
<213> ORGANISM: homo sapiens

<400> SEQUENCE: 41

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 42
<211> LENGTH: 70
<212> TYPE: PRT
<213> ORGANISM: human immunodeficiency virus

<400> SEQUENCE: 42

Phe His Cys Gln Val Cys Phe Thr Arg Lys Gly Leu Gly Ile Ser Tyr
1               5                   10                  15

Gly Arg Lys Lys Arg Arg Gln Arg Arg Ala Pro Gln Asp Ser Gln
            20                  25                  30

Thr His Gln Ala Ser Leu Ser Lys Gln Pro Ala Ser Gln Ser Arg Gly
            35                  40                  45

Asp Pro Thr Gly Pro Thr Glu Ser Lys Lys Val Glu Arg Glu Thr
    50                  55                  60

Glu Thr Asp Pro Phe Asp
65                  70

<210> SEQ ID NO 43
<211> LENGTH: 41
<212> TYPE: PRT
<213> ORGANISM: homo sapiens

<400> SEQUENCE: 43

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40

<210> SEQ ID NO 44
<211> LENGTH: 18
<212> TYPE: PRT
<213> ORGANISM: human immunodeficiency virus

<400> SEQUENCE: 44

Met Glu Pro Val Asp Pro Arg Leu Glu Pro Trp Lys His Pro Gly Ser
1               5                   10                  15

Gln Pro

<210> SEQ ID NO 45
<211> LENGTH: 20
<212> TYPE: PRT
<213> ORGANISM: Simian immunodeficiency virus

<400> SEQUENCE: 45

Lys Thr Ala Cys Asn Asn Cys His Cys Lys Val Cys Cys Tyr His Cys
1               5                   10                  15

Val Tyr Cys Phe

20

<210> SEQ ID NO 46
<211> LENGTH: 44
<212> TYPE: PRT
<213> ORGANISM: simian immunodeficiency virus

<400> SEQUENCE: 46

Thr Lys Lys Gly Leu Gly Ile Ser Tyr Gly Arg Lys Lys Arg Arg Arg
1               5                   10                  15

Pro Ala Arg Thr Ala Asp Lys Asp Gln Asp Asn Gln Asp Pro Val Ser
                20                  25                  30

Lys Gln Ser Leu Ala Gly Thr Arg Ser Gln Gln Glu
            35                  40

<210> SEQ ID NO 47
<211> LENGTH: 82
<212> TYPE: PRT
<213> ORGANISM: human immunodeficiency virus

<400> SEQUENCE: 47

Thr Thr Ala Cys Ser Lys Cys Tyr Cys Lys Ile Cys Cys Trp His Cys
1               5                   10                  15

Gln Leu Cys Leu Lys Lys Gly Leu Gly Ile Ser Tyr Gly Arg Lys Lys
                20                  25                  30

Arg Lys His Arg Arg Gly Thr Pro Gln Ser Ser Lys Asp His Gln Asn
            35                  40                  45

Pro Ile Pro Glu Gln Pro Leu Pro Ile Ile Arg Gly Asn Pro Thr Asp
50                  55                  60

Pro Lys Glu Ser Lys Lys Glu Val Ala Ser Lys Ala Glu Thr Asp Pro
65                  70                  75                  80

Phe Asp

<210> SEQ ID NO 48
<211> LENGTH: 19
<212> TYPE: PRT
<213> ORGANISM: homo sapiens

<400> SEQUENCE: 48

Met Glu Pro Leu Thr Pro His Pro Trp Val Tyr Ser Gly Gly Gln Pro
1               5                   10                  15

Lys Val Pro

<210> SEQ ID NO 49
<211> LENGTH: 83
<212> TYPE: PRT
<213> ORGANISM: Human immunodeficiency virus

<400> SEQUENCE: 49

Glu Thr Ala Cys Asn Asn Cys Phe Cys Lys Lys Cys Ser Tyr His Cys
1               5                   10                  15

Leu Val Cys Phe Gln Lys Lys Gly Leu Gly Ile Ser His Gly Arg Lys
                20                  25                  30

Lys Arg Arg Gln Arg Arg Ser Ala Pro Pro Ser Ser Glu Asp His Gln
            35                  40                  45

Asn Leu Ile Ser Lys Gln Pro Ile Pro Arg Thr Gln Gly Asp Gln Thr
50                  55                  60

Gly Ser Glu Glu Ser Lys Lys Lys Val Glu Ser Lys Thr Glu Thr Asp
65                  70                  75                  80

Pro Phe Asp

<210> SEQ ID NO 50
<211> LENGTH: 17
<212> TYPE: PRT
<213> ORGANISM: Artificial Sequence
<220> FEATURE:
<223> OTHER INFORMATION: immunosuppressive artificial sequence

<400> SEQUENCE: 50

Met Ala Gly Pro His Pro Val Ile Val Ile Thr Gly Pro His Glu Glu
1               5                   10                  15

Pro

<210> SEQ ID NO 51
<211> LENGTH: 30
<212> TYPE: PRT
<213> ORGANISM: Macaca mulatta

<400> SEQUENCE: 51

Arg Thr Cys His Cys Arg Ser Arg Cys Leu Arg Arg Glu Ser Asn Ser
1               5                   10                  15

Gly Ser Cys Asn Ile Asn Gly Arg Ile Ser Ser Leu Cys Cys
            20                  25                  30

<210> SEQ ID NO 52
<211> LENGTH: 64
<212> TYPE: PRT
<213> ORGANISM: simian immunodeficiency virus

<400> SEQUENCE: 52

Phe Leu Lys Lys Gly Leu Gly Ile Ser Tyr Glu Lys Ser His Arg Arg
1               5                   10                  15

Arg Arg Thr Pro Lys Lys Ala Lys Ala Asn Thr Ser Ser Ala Ser Asn
            20                  25                  30

Glu Pro Ile Pro Asn Arg Ile Arg Leu Cys Gln Pro Lys Lys Ala Lys
        35                  40                  45

Lys Glu Thr Val Glu Ala Ala Val Ala Thr Ala Pro Gly Leu Gly Arg
    50                  55                  60

<210> SEQ ID NO 53
<211> LENGTH: 82
<212> TYPE: PRT
<213> ORGANISM: simian immunodeficiency virus

<400> SEQUENCE: 53

Leu Glu Ala Cys Tyr Asn Lys Cys Tyr Cys Lys Arg Cys Cys Tyr His
1               5                   10                  15

Cys Gln His Cys Phe Leu Lys Lys Gly Leu Gly Ile Cys Tyr Glu Gln
            20                  25                  30

Gln Arg Arg Arg Thr Pro Lys Lys Thr Lys Ala Asn Thr Ser Ser Ala
        35                  40                  45

Ser Asp Lys Ser Leu Ser Arg Arg Ala Arg Asn Cys Gln Pro Lys Lys
    50                  55                  60

Glu Lys Lys Glu Thr Val Glu Ala Glu Val Ala Thr Asp Leu Gly Leu
65                  70                  75                  80

Gly Arg

<210> SEQ ID NO 54

-continued

```
<211> LENGTH: 20
<212> TYPE: PRT
<213> ORGANISM: simian immunodeficiency virus

<400> SEQUENCE: 54

Met Met Glu Pro Val Asp Pro Asp Leu Pro Lys Glu Gln His Pro Pro
1               5                   10                  15

Ala Thr Pro Arg
            20

<210> SEQ ID NO 55
<211> LENGTH: 32
<212> TYPE: PRT
<213> ORGANISM: Chlorocebus aethiops

<400> SEQUENCE: 55

Cys Glu Ser Cys Lys Leu Gly Arg Gly Arg Cys Arg Lys Glu Cys Leu
1               5                   10                  15

Glu Asn Glu Lys Pro Asp Gly Arg Cys Arg Leu Asn Phe Leu Cys Cys
            20                  25                  30

<210> SEQ ID NO 56
<211> LENGTH: 36
<212> TYPE: PRT
<213> ORGANISM: Human immunodeficiency virus

<400> SEQUENCE: 56

Met Glu Pro Val Asp Pro Arg Leu Glu Pro Trp Lys His Pro Gly Ser
1               5                   10                  15

Gln Pro Pro Glu Pro Val Asp Pro Arg Leu Glu Pro Trp Lys His Pro
            20                  25                  30

Gly Ser Gln Pro
        35

<210> SEQ ID NO 57
<211> LENGTH: 20
<212> TYPE: PRT
<213> ORGANISM: simian immunodeficiency virus

<400> SEQUENCE: 57

Lys Thr Ala Cys Asn Asn Cys His Cys Lys Val Cys Cys Tyr His Cys
1               5                   10                  15

Val Tyr Cys Phe
            20

<210> SEQ ID NO 58
<211> LENGTH: 31
<212> TYPE: PRT
<213> ORGANISM: pongo abelli

<400> SEQUENCE: 58

Leu Arg Cys Ile Cys Arg Arg Gly Ile Cys Arg Leu Leu Gln Arg Arg
1               5                   10                  15

Tyr Gly Ser Cys Ala Phe Pro Gly Arg Leu Tyr Arg Ile Cys Cys
            20                  25                  30

<210> SEQ ID NO 59
<211> LENGTH: 18
<212> TYPE: PRT
<213> ORGANISM: Human immunodeficiency virus

<400> SEQUENCE: 59
```

```
Met Glu Pro Val Asp Ala Asn Leu Glu Ala Trp Lys His Ala Gly Ser
1               5                   10                  15

Gln Pro

<210> SEQ ID NO 60
<211> LENGTH: 23
<212> TYPE: PRT
<213> ORGANISM: Simian immunodeficiency virus

<400> SEQUENCE: 60

Met Asp Pro Lys Gly Glu Glu Asp Gln Asp Val Ser His Gln Asp Leu
1               5                   10                  15

Ile Lys Gln Tyr Arg Lys Pro
            20

<210> SEQ ID NO 61
<211> LENGTH: 30
<212> TYPE: PRT
<213> ORGANISM: Simian immunodeficiency virus

<400> SEQUENCE: 61

Met Glu Thr Pro Leu Lys Glu Gln Glu Asn Ser Leu Glu Ser Cys Arg
1               5                   10                  15

Glu His Ser Ser Ser Ile Ser Glu Val Asp Val Pro Thr Pro
            20                  25                  30

<210> SEQ ID NO 62
<211> LENGTH: 31
<212> TYPE: PRT
<213> ORGANISM: Human immunodeficiency virus

<400> SEQUENCE: 62

Arg Lys Thr Ala Cys Thr Thr Cys Tyr Cys Lys Lys Cys Cys Phe His
1               5                   10                  15

Cys Gln Val Cys Phe Thr Arg Lys Gly Leu Gly Ile Ser Tyr Gly
            20                  25                  30

<210> SEQ ID NO 63
<211> LENGTH: 35
<212> TYPE: PRT
<213> ORGANISM: Human immunodeficiency virus

<400> SEQUENCE: 63

Arg Thr Ala Cys Asn Asn Cys Tyr Cys Lys Lys Cys Cys Phe His Cys
1               5                   10                  15

Tyr Ala Cys Phe Leu Arg Lys Gly Leu Gly Ile Thr Tyr His Ala Phe
            20                  25                  30

Arg Thr Arg
        35

<210> SEQ ID NO 64
<211> LENGTH: 47
<212> TYPE: PRT
<213> ORGANISM: Mus musculus

<400> SEQUENCE: 64

Val Ser Cys Leu Arg Lys Gly Gly Arg Cys Trp Asn Arg Cys Ile Gly
1               5                   10                  15

Asn Thr Arg Gln Ile Gly Ser Cys Gly Val Pro Phe Leu Lys Cys Cys
            20                  25                  30

Lys Arg Lys Pro Phe Thr Arg Lys Gly Leu Gly Ile Ser Tyr Gly
```

```
            35                  40                  45

<210> SEQ ID NO 65
<211> LENGTH: 30
<212> TYPE: PRT
<213> ORGANISM: Human immunodeficiency virus

<400> SEQUENCE: 65

Glu Thr Ala Cys Asn Asn Cys Phe Cys Lys Lys Cys Ser Tyr His Cys
1               5                   10                  15

Leu Val Cys Phe Gln Lys Lys Gly Leu Gly Ile Ser His Gly
            20                  25                  30

<210> SEQ ID NO 66
<211> LENGTH: 29
<212> TYPE: PRT
<213> ORGANISM: Human immunodeficiency virus

<400> SEQUENCE: 66

Thr Thr Ala Cys Ser Lys Cys Tyr Cys Lys Ile Cys Cys Trp His Cys
1               5                   10                  15

Gln Leu Cys Leu Lys Lys Gly Leu Gly Ile Ser Tyr Gly
            20                  25

<210> SEQ ID NO 67
<211> LENGTH: 31
<212> TYPE: PRT
<213> ORGANISM: Human immunodeficiency virus

<400> SEQUENCE: 67

Arg Lys Thr Ala Cys Thr Thr Cys Tyr Cys Lys Lys Cys Cys Phe His
1               5                   10                  15

Cys Gln Val Cys Phe Thr Arg Lys Gly Leu Gly Ile Ser Tyr Gly
            20                  25                  30

<210> SEQ ID NO 68
<211> LENGTH: 61
<212> TYPE: PRT
<213> ORGANISM: Simian immunodeficiency virus

<400> SEQUENCE: 68

Arg Lys Lys Ile Ala Ser Ala Asp Arg Ile Pro Val Pro Gln Gln Ser
1               5                   10                  15

Ile Ser Ile Arg Gly Arg Asp Ser Gln Thr Thr Gln Glu Ser Gln Lys
            20                  25                  30

Lys Val Glu Glu Gln Ala Lys Ala Asn Leu Arg Ile Ser Arg Lys Asn
            35                  40                  45

Leu Gly Asp Glu Thr Arg Gly Pro Val Gly Ala Gly Asn
        50                  55                  60

<210> SEQ ID NO 69
<211> LENGTH: 103
<212> TYPE: PRT
<213> ORGANISM: Artificial Sequence
<220> FEATURE:
<223> OTHER INFORMATION: Immunosuppressive Tat derivative polypeptide

<400> SEQUENCE: 69

Met Glu Pro Leu Thr Pro His Pro Trp Val Tyr Ser Gly Gly Gln Pro
1               5                   10                  15

Lys Val Pro Leu Glu Ala Cys Tyr Asn Lys Cys Tyr Cys Lys Arg Cys
            20                  25                  30
```

```
Cys Tyr His Cys Gln His Cys Phe Ser Lys Lys Gly Leu Gly Ile Ser
            35                  40                  45
Tyr Glu Arg Lys Gly Arg Arg Arg Thr Pro Arg Lys Thr Lys Thr
 50                  55                  60
Pro Ser Pro Ser Ala Pro Asp Lys Ser Ile Ser Thr Arg Thr Gly Asp
 65                  70                  75                  80
Ser Gln Pro Thr Lys Glu Gln Lys Lys Thr Ser Glu Ala Thr Val Val
                85                  90                  95
Thr Thr Cys Gly Leu Gly Gln
            100
```

<210> SEQ ID NO 70
<211> LENGTH: 21
<212> TYPE: PRT
<213> ORGANISM: Simian immunodeficiency virus

<400> SEQUENCE: 70

```
Leu Glu Ala Cys Tyr Asn Lys Cys Tyr Cys Lys Arg Cys Cys Tyr His
  1               5                  10                  15
Cys Gln His Cys Phe
            20
```

<210> SEQ ID NO 71
<211> LENGTH: 63
<212> TYPE: PRT
<213> ORGANISM: Human immunodeficiency virus

<400> SEQUENCE: 71

```
Ser Lys Lys Gly Leu Gly Ile Ser Tyr Glu Arg Lys Gly Arg Arg Arg
  1               5                  10                  15
Arg Thr Pro Arg Lys Thr Lys Thr Pro Ser Pro Ser Ala Pro Asp Lys
                20                  25                  30
Ser Ile Ser Thr Arg Thr Gly Asp Ser Gln Pro Thr Lys Glu Gln Lys
            35                  40                  45
Lys Thr Ser Glu Ala Thr Val Val Thr Thr Cys Gly Leu Gly Gln
 50                  55                  60
```

<210> SEQ ID NO 72
<211> LENGTH: 127
<212> TYPE: PRT
<213> ORGANISM: Mus musculus

<400> SEQUENCE: 72

```
Met Asp Pro Thr Asp Pro Glu Leu Pro Pro Trp Gln Gln Pro Gly Ser
  1               5                  10                  15
Gln Pro Pro Thr Pro Arg Lys Thr Ala Cys Thr Thr Cys Tyr Cys Lys
                20                  25                  30
Lys Cys Cys Phe His Cys Gln Val Cys Phe Leu Gln Lys Gly Leu Gly
            35                  40                  45
Ile Thr Tyr Ala Arg Pro Arg Lys Arg Ala Ala Arg Ser Ile Ser Glu
 50                  55                  60
Asp Asp Ser Ala Pro Thr Glu Pro Tyr Pro Gly Pro Glu Gly Pro Arg
 65                  70                  75                  80
Gln Thr Arg Arg Arg Arg Arg Arg Gln Trp Arg Gln Arg Gln Thr Gln
                85                  90                  95
Arg Leu Tyr Leu Gln Gln Arg Ile Phe Glu Ala Ile Phe Gly Ser Arg
            100                 105                 110
```

-continued

```
Thr Ala Ala Leu Glu Asp Ser Leu Gln Gln Leu Gln Ile Ser Asp
        115                 120                 125
```